US009579096B2

(12) United States Patent
Mori et al.

(10) Patent No.: US 9,579,096 B2
(45) Date of Patent: Feb. 28, 2017

(54) SUTURING APPARATUS

(75) Inventors: Hirohito Mori, Kagawa (JP); Tatsurou Sugitani, Tokyo (JP); Yoshihito Momose, Okaya (JP)

(73) Assignee: NATIONAL UNIVERSITY CORPORATION KAGAWA UNIVERSITY, Kagawa (JP)

( * ) Notice: Subject to any disclaimer, the term of this patent is extended or adjusted under 35 U.S.C. 154(b) by 888 days.

(21) Appl. No.: 13/981,479

(22) PCT Filed: Jan. 23, 2012

(86) PCT No.: PCT/JP2012/000371
§ 371 (c)(1),
(2), (4) Date: Dec. 27, 2013

(87) PCT Pub. No.: WO2012/101999
PCT Pub. Date: Aug. 12, 2012

(65) Prior Publication Data
US 2014/0121457 A1 May 1, 2014

(30) Foreign Application Priority Data

Jan. 25, 2011 (JP) .................................. 2011-013025

(51) Int. Cl.
*A61B 17/04* (2006.01)
*A61B 17/06* (2006.01)
(Continued)

(52) U.S. Cl.
CPC ....... *A61B 17/0469* (2013.01); *A61B 1/00087* (2013.01); *A61B 17/0482* (2013.01);
(Continued)

(58) Field of Classification Search
CPC ............ A61B 17/0469; A61B 17/0483; A61B 17/0625; A61B 1/00087; A61B 17/06166; A61B 17/06066; A61B 17/0487; A61B 17/0482; A61B 2017/06042; A61B 17/0485; A61B 2017/0496; A61B 2017/00818; A61B 2017/0472
See application file for complete search history.

(56) References Cited

U.S. PATENT DOCUMENTS 5,507,755 A * 4/1996 Gresl ................. A61B 17/0469
606/139
6,117,144 A * 9/2000 Nobles ............... A61B 17/0057
606/139
(Continued)

*Primary Examiner* — Julian W Woo
(74) *Attorney, Agent, or Firm* — Nixon Peabody LLP; Jeffrey L. Costellia

(57) ABSTRACT

Provided is a suturing apparatus for endoscope capable of suturing an opening of a wound, with an endoscope inserted into cavity of a digestive tract, to the same extent as the surgical operation.

The suturing apparatus includes a front arm 11, a rear arm 12, arm moving means 13 for causing the front arm 11 and the rear arm 12 to move closer to or away from each other, and rocking means for relatively rocking the front arm 11 and the rear arm 12. The rear arm 12 includes a needle-like member 14 provided on a surface on a side of the front arm 11 so that an axial direction thereof becomes parallel with a direction in which the front arm 11 and the rear arm 12 are moved closer to or away from each other. The front arm 11 is provided with a housing space 16 capable of housing a tip of the needle-like member 14 when the front arm 11 and the rear arm 12 are moved closer to each other. Each of the housing spaces houses an engagement member 21 capable of being engaged with the needle-like member 14. The engagement members 21 housed in the respective housing spaces 16 are connected to each other by a suture thread 22.

21 Claims, 32 Drawing Sheets

(51) Int. Cl.
*A61B 1/00* (2006.01)
*A61B 17/062* (2006.01)
*A61B 17/00* (2006.01)

(52) U.S. Cl.
CPC ...... *A61B 17/0483* (2013.01); *A61B 17/0487* (2013.01); *A61B 17/0625* (2013.01); *A61B 17/06066* (2013.01); *A61B 17/06166* (2013.01); *A61B 17/0485* (2013.01); *A61B 2017/00818* (2013.01); *A61B 2017/0472* (2013.01); *A61B 2017/0496* (2013.01); *A61B 2017/06042* (2013.01)

(56) References Cited

U.S. PATENT DOCUMENTS

| | | | | |
|---|---|---|---|---|
| 6,562,052 | B2 * | 5/2003 | Nobles | A61B 17/0057 606/144 |
| 7,029,481 | B1 * | 4/2006 | Burdulis, Jr. | A61B 17/0469 606/144 |
| 7,160,309 | B2 * | 1/2007 | Voss | A61B 17/0057 606/1 |
| 9,398,907 | B2 * | 7/2016 | Nobles | A61B 17/0469 |

* cited by examiner (D)

(A)

(B)

(A)

(B)

(1)

(2)

(3)

(4)

(5)

(6)

(7)

(8)

(1)

(2)

(3)

(4)

(5)

(6)

(7)

(8)

(A)    (B)

(C)    (D)

(A)

(B)

(C)

(A)

(B)

(C)

SUTURING APPARATUS

TECHNICAL FIELD

The present invention relates to a suturing apparatus, and more particularly, to a suturing apparatus used for natural orifice transluminal endoscopic surgery such as surgery for forming a through hole in a digestive tract or surgery on abdominal cavity performed with a flexible endoscope inserted into cavity of a digestive tract such as a mouth, an anus or a vagina.

BACKGROUND ART

In the natural orifice transluminal endoscopic surgery (hereinafter, referred to as NOTES), for example, a focus in cavity of a digestive tract or abdominal cavity is removed by a flexible endoscope inserted into the cavity of digestive tract such as a mouth, an anus or a vagina.

For example, NOTES includes surgery for removing, with a flexible endoscope, a gastric wall in which a through hole is formed, more specifically, removing a tumor lying deeper than a submucosa in the gastric wall, that is, a tumor lying in a muscularis propria.

As shown in FIG. 32, NOTES also includes surgery for removing, with a flexible endoscope S, a tumor or the like formed in a pancreas, liver or the like by inserting the flexible endoscope S from a mouth, forming a hole h in a gastric wall with a tip of the endoscope S, and causing the tip of the endoscope S to enter abdominal cavity from the hole h.

When the tumor in the gastric wall, pancreas or the like is removed by performing such NOTES, a removed region or the hole h in the gastric wall needs to be sutured after the removal. Conventionally, the flexible endoscope S enables the removal of tumor or the like, however, the removed region cannot be sutured at the cavity of the digestive tract.

Because of this, surgery in which a tumor or the like is removed with the flexible endoscope S and suturing is performed with a laparoscope is performed at present. Unfortunately, in such a case, a scar stays on a body surface because a hole for inserting the laparoscope from the body surface into the abdominal cavity needs to be formed in an abdominal wall.

If not only removal but also suturing can be performed with the endoscope S at the cavity of the digestive tract, the surgery can be performed without forming a scar on the body surface. Therefore, a technique for suturing the removed region at the cavity of digestive tract has been developed recently (for example, Patent Literature 1).

As for suturing an incised part in surgery, end faces of both edges are sutured while butting against each other in order that biological tissues easily adhere to each other. However, according to the technique disclosed in Patent Literature 1, outer faces of edges are sutured while facing each other. In other words, the outer faces of both edges in the incised part of a gastric wall are sutured in surface contact with each other. The suturing according to the technique in Patent Literature 1 therefore causes a problem that a wound is not completely closed because it is difficult to promote the adhesion of the biological tissues in the contact area.

Moreover, a part on a tip side with respect to the sutured part protrudes into the stomach in a heaped up manner at the edges of the incised part. The sutured part may cause various problems with respect to food provided to the stomach.

Further more, the part on the tip side with respect to the sutured part is not supplied with blood at the edges of the incised part. The biological tissues may necrose.

As described above, according to the technique that has been developed for suturing the removed part at the abdominal cavity, it is difficult to suture a wound similarly to a surgical operation. Therefore, development of a technique capable of suturing a wound similarly to a surgical operation has been required.

CITATION LIST

Patent Literature

Patent Literature 1: Japanese Patent Laid-Open No. 2004-601

SUMMARY OF INVENTION

Technical Problem

In view of the above circumstances, an object of the present invention is to provide a suturing apparatus for endoscope capable of suturing a wound similarly to a surgical operation by using an endoscope inserted into cavity of a digestive tract.

Solution to Problem (Suturing)

A suturing apparatus attached to an endoscope and inserted into a body for use according to a first feature of the present invention includes: a front arm; a rear arm provided movably closer to or away from the front arm; arm moving means for causing the front arm and the rear arm to move closer to or away from each other; and rocking means for relatively rocking the front arm and the rear arm around a rocker shaft in parallel with a direction in which the front arm and the rear arm are moved closer to or away from each other, wherein the rear arm includes: a needle-like member attached to the rear arm so that a tip of the needle-like member faces to the front arm and a central axis thereof becomes parallel with the direction in which the front arm and the rear arm are moved closer to or away from each other, the front arm includes: a pair of branch portions whose base ends are connected to each other, the pair of branch portions each being provided with a housing space capable of housing the tip of the needle-like member when the front arm and the rear arm are moved closer to each other, each of the housing spaces houses each of a pair of engagement members capable of being engaged with the needle-like member, and the pair of engagement members housed in the housing spaces are connected to each other by a suture thread.

A suturing apparatus according to a third feature of the present invention is the first feature of the present invention further including: a connection mechanism including a front connection member and a rear connection member provided engageably/removably each other, wherein the rear connection member is provided on the rear arm, the front connection member is provided on the front arm, and the connection mechanism is formed so that the front connection member and the rear connection member fix relative rocking of the front arm and the rear arm at a predetermined position, and, in the fixed state at the predetermined position, are engaged with each other relatively movable along the direction in which the front arm and the rear arm are moved closer to or away from each other, the predetermined position being a position where a central axis of each housing space corresponds to a central axis of the needle-like member.

A suturing apparatus according to a fourth feature of the present invention is the third feature of the present invention, wherein the front connection member is provided with a guide groove engaged with the rear connection member and guiding a movement of the rear connection member along an axial direction of the rocker shaft.

A suturing apparatus according to a fifth feature of the present invention is the fourth feature of the present invention, wherein the front arm is provided with a pair of housing spaces, the guide groove formed in the front connection member includes: a pair of intersecting surfaces in parallel with the axial direction of the rocker shaft and intersecting each other, the rear connection member includes: a reference side face in parallel with the axial direction of the rocker shaft; and a pair of positioning side faces in parallel with the axial direction of the rocker shaft and intersecting with the reference side face, the rear connection member is provided so that, when the reference side face is engaged with the guide groove so as to come in surface contact with one intersecting surface, one positioning side face comes in contact with the other intersecting surface, on the other hand, when the reference side face is engaged with the guide groove so as to come in surface contact with the other intersecting surface, the other positioning side face comes in contact with the one intersecting surface, and the pair of housing spaces is formed so that, when the rear connection member is engaged with the guide groove so that the reference side face comes in surface contact with one intersecting surface, a central axis of one housing space corresponds to the central axis of the needle-like member, on the other hand, when the rear connection member is engaged with the guide groove so that the reference side face comes in surface contact with the other intersecting surface, a central axis of the other housing space corresponds to the central axis of the needle-like member.

A suturing apparatus attached to an endoscope and inserted into a body for use according to a sixth feature of the present invention includes: a front arm; a rear arm provided movably closer to or away from the front arm; and arm moving means for causing the front arm and the rear arm to move closer to or away from each other, wherein the rear arm includes: a pair of branch portions whose base ends are connected to each other, the pair of branch portions includes: a pair of needle-like members provided so that tips of the needle-like members face to the front arm and central axes thereof become parallel with a direction in which the front arm and the rear arm are moved closer to or away from each other, the front arm includes: a pair of branch portions whose base ends are connected to each other, the pair of branch portions being provided with a pair of housing spaces capable of respectively housing the tips of the pair of needle-like members when the front arm and the rear arm are moved closer to each other, the pair of housing spaces are provided so that, when a central axis of one housing space becomes coaxial with a central axis of one needle-like member, a central axis of the other housing space becomes coaxial with a central axis of the other needle-like member, each of the housing spaces houses each of a pair of engagement members capable of being engaged with the needle-like member, and the pair of engagement members housed in the housing spaces are connected to each other by a suture thread.

A suturing apparatus according to an eighth feature of the present invention is the sixth feature of the present invention, further including: a connection mechanism including a front connection member and a rear connection member provided engageably/removably each other, wherein the rear connection member is provided on the rear arm, the front connection member is provided on the front arm, and the connection mechanism is formed so that the front connection member and the rear connection member are engaged with each other relatively movable along the direction in which the front arm and the rear arm are moved closer to or away from each other, and, in the engaged state, each central axis of the plurality of needle-like members is coaxial with each central axis of the plurality of housing spaces and rocking of the rear arm is fixed.

A suturing apparatus according to a ninth feature of the present invention is the eighth feature of the present invention, wherein the front connection member is provided with a guide groove engaged with the rear connection member and guiding a movement of the engaged rear connection member along an axial direction of a rocker shaft.

A suturing apparatus attached to an endoscope and inserted into a body for use according to a tenth feature of the present invention includes: a front arm; a rear arm provided movably closer to or away from the front arm; and arm moving means for causing the front arm and the rear arm to move closer to or away from each other, wherein the rear arm includes: a needle-like member attached to the rear arm so that a tip of the needle-like member faces to the front arm and a central axis thereof becomes parallel with a direction in which the front arm and the rear arm are moved closer to or away from each other, the front arm is provided with a housing space capable of housing the tip of the needle-like member when the front arm and the rear arm are moved closer to each other, the front arm houses a suturing instrument including a pair of engagement members connected by a suture thread and capable of being engaged with the needle-like member, and the front arm is provided with a supply mechanism in which, when one engagement member is engaged with the needle-like member, the other engagement member can be housed outside the housing space, and then, the other engagement member can be supplied to the housing space after the one engagement member is engaged with the needle-like member.

A suturing apparatus according to an eleventh feature of the present invention is the tenth feature of the present invention, wherein the engagement member includes: a through hole through which the tip of the needle-like member can be inserted, the supply mechanism includes: a suturing-instrument holding space formed in the front arm, communicating with the housing space and housing the suturing instrument, and the housing space houses the engagement member of the suturing instrument supplied from the suturing-instrument holding space so that an axial direction of the through hole of the engagement member becomes parallel with a direction of movement of the needle-like member.

A suturing apparatus according to a twelfth feature of the present invention is any one of the first to eleventh features of the present invention, wherein the engagement member includes: a through hole through which the tip of the needle-like member is inserted, and the tip of the needle-like member is provided with a falling-off prevention portion preventing the engagement member from coming out of the tip when the tip is inserted through the through hole of the engagement member.

A suturing apparatus according to a thirteenth feature of the present invention is the twelfth feature of the present invention, wherein the falling-off prevention portion is an expanded diameter portion formed on a side face of the needle-like member.

A suturing apparatus according to a fourteenth feature of the present invention is the twelfth or thirteenth feature of the present invention, wherein the engagement member includes: an engagement portion with the through hole; and a connection piece for connection with the suture thread, and an axial direction of the connection piece is in parallel with a central axis of the through hole.

A suturing apparatus according to a fifteenth feature of the present invention is the fourteenth feature of the present invention, wherein a connection-piece housing groove is provided on a side face of the front arm along an axial direction of the housing space.

A suturing apparatus according to a sixteenth feature of the present invention is the twelfth, thirteenth, fourteenth or fifteenth feature of the present invention, wherein an engagement piece engaged with the expanded diameter portion is provided on an inner face of the through hole in the engagement member.

A suturing apparatus according to a seventeenth feature of the present invention is any one of the first to sixteenth features of the present invention, wherein the rear arm includes: a hollow needle provided on a surface on a side of the front arm so that an axial direction of the hollow needle becomes parallel with the direction in which the front arm and the rear arm are moved closer to or away from each other, and the needle-like member is provided in the hollow needle.

A suturing apparatus according to an eighteenth feature of the present invention is any one of the first to seventeenth features of the present invention, wherein the suturing apparatus is attached to an endoscope for use so that both of the front arm and the rear arm are located ahead of a tip face of the endoscope and the rear arm is located on a side of the tip face of the endoscope with respect to the front arm.

(Thread-Fastening)

A suturing apparatus according to a nineteenth feature of the present invention is any one of the first to eighteenth features of the present invention, further including: a thread-fastening member including a hollow tubular member, and a linear member having a loop portion inserted through the tubular member and protruding from one end of the tubular member, wherein the thread-fastening member is provided with the tubular member movably along the linear member, and the front arm and/or the rear arm is inserted through the loop portion.

A suturing apparatus according to a twentieth feature of the present invention is any one of the first to eighteenth features of the present invention, wherein the rear arm is provided with a through hole extending through the rear arm along the direction in which the front arm and the rear arm are moved closer to or away from each other, the needle-like member is attached to the rear arm so as to be located in the through hole, when the through hole is viewed from an axial direction thereof, the suturing apparatus includes: a thread-fastening member fastening the suture thread ahead of the tip of the needle-like member, while the pair of engagement members in the suturing instrument is engaged with the tip of the needle-like member, the thread-fastening member includes: a clamp member having a thread-housing groove through which the suture thread passes, the clamp member capable of holding the suture thread provided in the thread-housing groove when a width of the thread-housing groove becomes narrower, and the clamp member is formed into such a shape as to be able to pass the through hole of the rear arm along the direction in which the front arm and the rear arm are moved closer to or away from each other, and as to allow the needle-like member to pass through the thread-housing groove, when passing the through hole of the rear arm.

A suturing apparatus according to a twenty-first feature of the present invention is the twentieth feature of the present invention, wherein the thread-fastening member includes: the tubular member formed into such a shape as to be able to pass the through hole of the rear arm along the direction in which the front arm and the rear arm are moved closer to or away from each other, a section of the tubular member is formed into such a shape as to allow the needle-like member to be housed thereinside at the time of passing the through hole of the rear arm, the tubular member houses the clamp member provided so that an axial direction of the thread-housing groove corresponds to an axial direction of the tubular member, and a ring-shaped fastening member provided between the clamp member and an inner face of the tubular member, an outside diameter of the clamp member becomes shorter from a base end thereof toward a tip, and an inside diameter of the fastening member is not less than an outside diameter of the tip of the clamp member and not more than an outside diameter of the base end of the clamp member.

A suturing apparatus according to a twenty-second feature of the present invention is the twenty-first feature of the present invention, wherein the tubular member includes: a holding mechanism holding the fastening member at a tip of the tubular member, the holding mechanism holds the fastening member not to move toward the tip of the tubular member, when the clamp member relatively moves toward the tip of the tubular member, until a stress generated between the clamp member and the fastening member reaches a predetermined magnitude, and the fastening member is discharged from the tip of the tubular member when the stress generated between the clamp member and the fastening member reaches the predetermined magnitude or more.

A suturing apparatus according to a twenty-third feature of the present invention is the twentieth, twenty-first or twenty-second feature of the present invention, wherein the clamp member includes: a gripper provided on an inner face of the thread-housing groove, and nipping and holding the suture thread; and a cutting edge provided on the inner face of the thread-housing groove and located on a side of a base end with respect to the gripper, and the cutting edge may cut the suture thread when a width of the thread-housing groove becomes narrower in a state of the gripper holding the suture thread.

Advantageous Effects of Invention (Suturing)

According to the first feature of the present invention, the tip of the needle-like member can be inserted into one housing space, when the front arm and the rear arm are provided so that the needle-like member faces to the one housing space and the arm moving means causes the front arm and the rear arm to move closer to each other. Since the engagement member is provided in the one housing space, the engagement member (one engagement member) can be engaged with the tip of the needle-like member. After the front arm and the rear arm are moved away from each other with the one engagement member engaged with the tip of the needle-like member, by rocking the rear arm, the front arm and the rear arm are provided so that the needle-like member faces the other housing space. When the arm moving means causes the front arm and the rear arm to move closer to each other in such a state, the tip of the needle-like member can be inserted into the other housing space. Therefore, the engagement member (the other engagement member) in the other housing space can be engaged with the tip of the needle-like member. Then, the suture thread connecting the engagement members to each other can be formed into a loop because the plurality of the engagement members are engaged with the needle-like member. Accordingly, the suturing apparatus attached to the endoscope is inserted into a body, one edge is sandwiched between the front arm and the rear arm in an incised part such as a gastric wall, and then the front arm and the rear arm are once moved closer to each other and then moved away from each other. In that case, the suture thread can pass through the one edge. Then, when the other edge is sandwiched between the front arm and the rear arm, and the front arm and the rear arm are once moved closer to each other and then moved away from each other, the suture thread can pass through the other edge. Consequently, the suture thread that has passed through the pair of edges in the incised part and whose both end portions (parts connected to the engagement members) are located on a side of the rear arm can be formed into a loop. When the both end portions of the suture thread having a loop shape are fastened, the incised part can be sutured with end faces (incised surfaces) of the pair of edges butting against each other, similarly to suturing in a normal surgical operation. Moreover, each of the pair of the branch portions is provided with the housing space. The central axis of the housing space in one branch portion corresponds to the central axis of the needle-like member, and the front arm and the rear arm are once moved closer to each other and then moved away from each other. Then, the central axis of the housing space in the other branch portion corresponds to the central axis of the needle-like member, and the front arm and the rear arm are once moved closer to each other and then moved away from each other. In that case, the suture thread that has passed through the pair of edges in the incised part and whose both end portions are located on the side of the rear arm can be formed into a loop.

According to the third feature of the present invention, when the front connection member and the rear connection member of the connection mechanism are engaged with each other, relative rocking of the front arm and the rear arm can be fixed. Moreover, the central axis of the needle-like member can easily correspond to the central axis of the housing space. Consequently, an operation of inserting the tip of the needle-like member into the housing space can be simplified when the arm moving means causes the front arm and the rear arm to move closer to each other.

According to the fourth feature of the present invention, a structure of the connection mechanism can be simplified because the rear connection member is simply required to be engaged with the guide groove.

According to the fifth feature of the present invention, since the rear connection member comes in surface contact with the guide groove at two faces, the rear connection member can be certainly in a predetermined posture and can be moved in such a posture. Therefore, the tip of the needle-like member can be certainly and easily inserted into the housing space.

According to the six feature of the present invention, the tip of each needle-like member can be inserted into each housing space, when the front arm and the rear arm are provided so that one needle-like member faces to one housing space and the arm moving means causes the front arm and the rear arm to move closer to each other. Then, the engagement member in each housing space can be engaged with the tip of each needle-like member. When the front arm and the rear arm are moved away from each other in such a state, the needle-like members can be connected to each other by the suture thread. The suturing apparatus attached to the endoscope is inserted into the body, one edge is provided between the one needle-like member and the one housing space in the incised part such as a gastric wall, and the other edge is provided between the other needle-like member and the other housing space. Then, the front arm and the rear arm are once moved closer to each other and then moved away from each other. Consequently, the suture thread that has passed through the pair of edges in the incised part and whose both end portions (parts connected to the engagement members) are located on the side of the rear arm can be formed into a loop. When the both end portions of the suture thread are fastened in such a state, the incised part can be sutured with end faces (incised surfaces) of the pair of edges butting against each other, similarly to suturing in a normal surgical operation. The loop of the suture thread passing through the pair of edges in the incised part can be formed simply by moving the front arm and the rear arm closer to and away from each other once. Time for the suturing operation can therefore be reduced. Moreover, each of the pair of the branch portions is provided with the housing space. The central axis of the housing space corresponds to the central axis of the needle-like member, and the front arm and the rear arm are once moved closer to each other. In that case, the suture thread that has passed through the pair of edges in the incised part and whose both end portions are located on the side of the rear arm can be formed into a loop.

According to the eighth feature of the present invention, the central axis of the needle-like member can correspond to the central axis of the housing space simply by rocking the rear arm. Consequently, the operation of inserting the tip of the needle-like member into the housing space can be simplified when the arm moving means causes the front arm and the rear arm to move closer to each other.

According to the ninth feature of the present invention, a structure of the connection mechanism can be simplified because the rear connection member is simply required to be engaged with the guide groove.

According to the tenth feature of the present invention, the tip of the needle-like member can be inserted into the housing space, when the front arm and the rear arm are provided so that the needle-like member faces to the housing space and the arm moving means causes the front arm and the rear arm to move closer to each other. Since one engagement member of the suturing instrument is provided in the housing space, the one engagement member can be engaged with the tip of the needle-like member. When the front arm and the rear arm are moved away from each other with the one engagement member of the suturing instrument engaged with the tip of the needle-like member, the supply mechanism supplies the other engagement member of the suturing instrument into the housing space. When the arm moving means causes the front arm and the rear arm to move closer to each other in such a state, the other engagement member of the suturing instrument can be engaged with the tip of the needle-like member. Since both of the pair of engagement members are engaged with the needle-like member, the suture thread connecting the pair of engagement members to each other can be formed into a loop. Accordingly, the suturing apparatus attached to the endoscope is inserted into the body, one edge is sandwiched between the front arm and the rear arm in the incised part such as a gastric wall, and the front arm and the rear arm are once moved closer to each other and then moved away from each other In that case, the suture thread can pass through the one edge. Then, when the other edge is sandwiched between the front arm and the rear arm, and the front arm and the rear arm are once moved closer to each other and then moved away from each other, the suture thread can pass through the other edge. Consequently, the suture thread that has passed through the pair of edges in the incised part and whose both end portions (end portions connected to the pair of engagement members) are located on the side of the rear arm can be formed into a loop by the suturing instrument. When the both end portions of the suture thread are fastened, the incised part can be sutured with end faces (incised surfaces) of the pair of edges butting against each other, similarly to suturing in a normal surgical operation.

According to the eleventh feature of the present invention, when the one engagement member is removed from the housing space, the other engagement member of the suturing instrument is supplied from the suturing-instrument holding space into the housing space. When the engagement member is supplied into the housing space, an axial direction of the through hole of the engagement member in the suturing instrument becomes substantially parallel with a direction of movement of the needle-like member in the housing space. Therefore, the tip of the needle-like member can be certainly inserted through the through hole of the engagement member when the front arm and the rear arm are moved closer to each other.

According to the twelfth feature of the present invention, the falling-off prevention portion prevents the engagement member from falling off from the needle-like member. Therefore, even if the needle-like member having the engagement member engaged therewith is stuck into a gastric wall or the like, or the needle-like member having the engagement member engaged therewith and stuck into the gastric wall or the like is pulled out from the gastric wall or the like, the engagement member can be prevented from falling off from the needle-like member. Consequently, the suture thread that has passed through the pair of edges in the incised part and whose both end portions are located on the side of the rear arm can be certainly formed into a loop.

According to the thirteenth feature of the present invention, a structure of the needle-like member can be simplified because the needle-like member is simply provided with the expanded diameter portion.

According to the fourteenth feature of the present invention, the connection piece is in parallel with the central axis of the through hole. Therefore, when the engagement member is connected to the tip of the needle-like member, the connection piece can be along a side face of the needle-like member. Consequently, a resistance due to the connection piece can be reduced at the time of passing the needle-like member through the gastric wall or the like.

According to the fifteenth feature of the present invention, the engagement member can be stably held in the housing space. This can happen if the engagement member is provided in the housing space so that the connection piece is provided in the connection-piece housing groove.

According to the sixteenth feature of the present invention, a structure of the engagement member can be simplified because the engagement piece is simply provided. Moreover, since a resistance can be reduced at the time of passing the needle-like member through the through hole of the engagement member, the needle-like member can be engaged with the engagement member more certainly.

According to the seventeenth feature of the present invention, the needle-like member is provided in the hollow needle. The hollow needle can therefore protect the needle-like member, thereby reducing a possibility of damaging the needle-like member.

According to the eighteenth feature of the present invention, when the suturing apparatus is attached to the endoscope for use, the incised part formed on a digestive tract such as a stomach can be sutured at the digestive tract such as a stomach. Therefore, surgery for removing a tumor or the like from a digestive tract or various organs, or surgery for incising a digestive tract or the like can be performed without forming a scar on a body surface.

(Thread-Fastening)

According to the nineteenth feature of the present invention, the suture thread can be bundled with the loop portion of the linear member by reducing the loop portion in size. This can happen if the suture thread is provided in the loop portion, followed by pulling the linear member or moving the tubular member toward the loop portion with the plurality of the engagement members engaged with the needle-like member. When the linear member is further pulled or the tubular member is further moved toward the loop portion in such a state, both end portions of the suture thread can be drawn into the tubular member together with the linear member. Since the end portions of the suture thread are fixed by the tubular member in close contact with each other, the suture thread can be fastened.

According to the twentieth feature of the present invention, the both end portions of the suture thread can be provided in the thread-housing groove of the clamp member when the clamp member is provided ahead of the needle-like member through the through hole. When a width of the thread-housing groove of the clamp member is narrowed in such a state, the clamp member can nip and hold the both end portions of the suture thread. Therefore, the both end portions can be in the same state as the case of connecting (fastening) the both end portions of the suture thread. The suture thread is then cut between the clamp member and the engagement member, and thereby the pair of edges in the incised part can be sutured.

According to the twenty-first feature of the present invention, the clamp member can be provided ahead of the needle-like member when the tubular member passes the through hole of the rear arm with the clamp member housed in the tubular member. An outside diameter of the clamp member becomes shorter from the base end toward the tip, and further, an inside diameter of the fastening member is not less than the outside diameter of the tip of the clamp member and not more than the outside diameter of the base end of the clamp member. Therefore, when the clamp member is pushed into the fastening member, the clamp member is deformed so that the width of the thread-housing groove becomes narrower as the clamp member is pushed into the fastening member. Consequently, the suture thread is nipped by the inner face of the thread-housing groove. That is, the clamp member can nip and hold the both end portions of the suture thread. The both end portions can be in the same state as the case of connecting (fastening) the both end portions of the suture thread simply by passing the tubular member through the through hole of the rear arm and pushing the clamp member into the fastening member. The thread-fastening can therefore be performed quickly and easily.

According to the twenty-second feature of the present invention, the holding mechanism holds the fastening member so as not to move toward the tip of the tubular member until a predetermined stress is generated between the clamp member and the fastening member. Then, the clamp member can be certainly deformed until the width of the thread-housing groove becomes narrower so as to be able to nip the suture thread. Therefore, the clamp member can certainly nip and hold the both end portions of the suture thread.

According to the twenty-third feature of the present invention, the gripper of the clamp member can hold the suture thread and the suture thread can be cut simply by pushing the clamp member into the fastening member. The incised part can therefore be sutured more quickly.

DESCRIPTION OF EMBODIMENTS

An embodiment of the present invention will now be described with reference to the drawings.

A suturing apparatus of the preset invention is used for suturing an incised part or the like formed on an organ or a digestive tract in abdominal cavity. In the natural orifice transluminal endoscopic surgery (hereinafter, referred to as NOTES) using a flexible endoscope, the suturing apparatus is attached to the flexible endoscope for suturing the incised part or the like at cavity of the digestive tract.

The suturing apparatus of the present invention can be used not only for flexible endoscopes but also for laparoscopes by attaching the suturing apparatus to tips thereof. In the case where the suturing apparatus of the present invention is attached to the flexible endoscope for use in NOTES, removal of tumor or the like, and also suturing an incised part or the like formed for the removal of tumor can be performed only with the flexible endoscope provided in cavity of the digestive tract. The surgery can be advantageously performed without forming a scar on the body surface.

Hereinafter, a case where a suturing apparatus 10 in the embodiment is attached to a flexible endoscope for use will be described as an example.

In order to simplify a structure of each part of the apparatus, relative sizes among respective parts in the respective drawings do not always correspond to sizes in the actual apparatus.

(Description of Endoscope 1)

Figure 1:
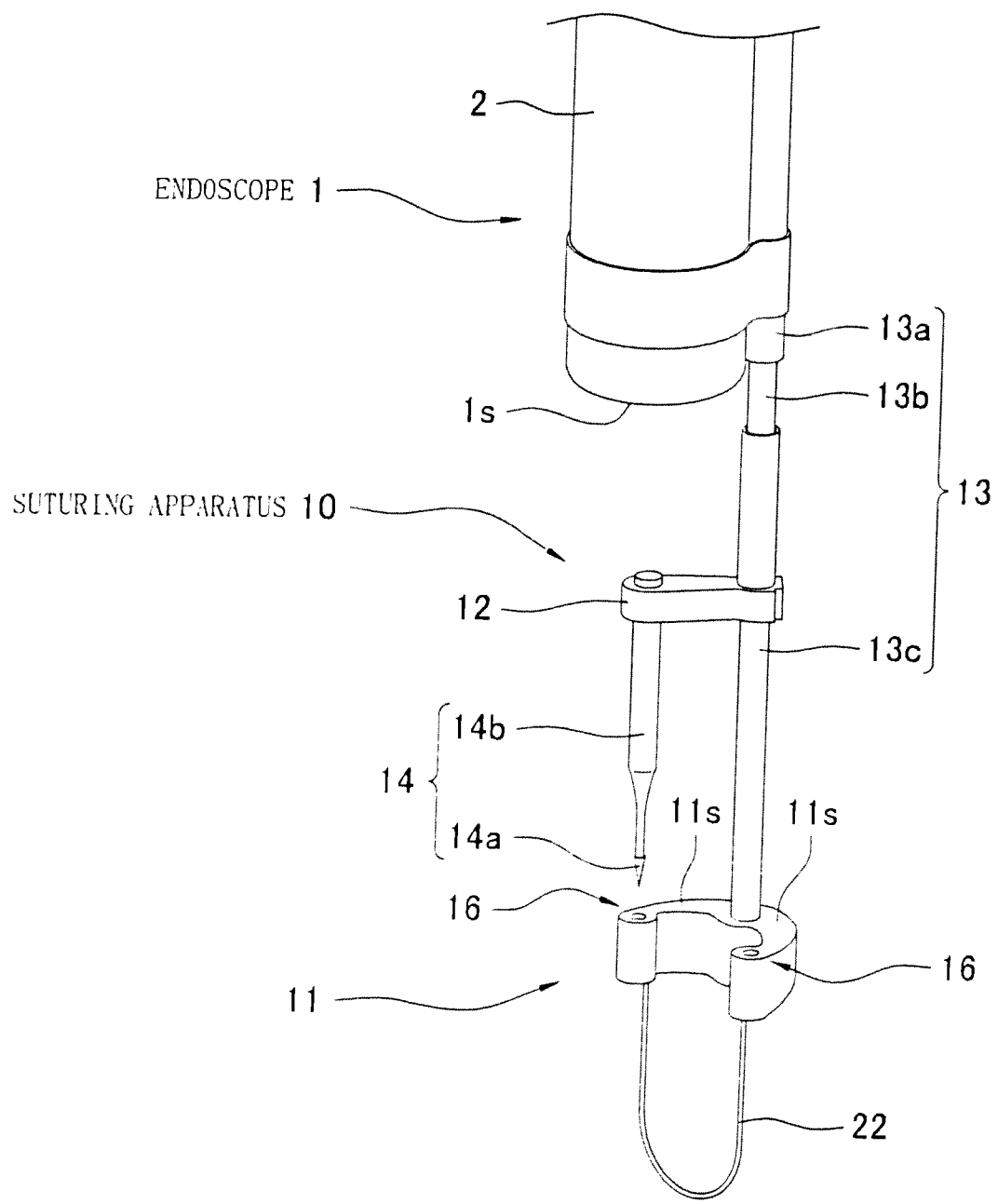
FIG. 1 is a schematic view of an endoscope 1 having a suturing apparatus 10 in an embodiment.

In FIG. 1, reference numeral 1 indicates an endoscope to which the suturing apparatus 10 in the embodiment is attached. The endoscope 1 is a flexible endoscope used for general endoscopic surgery.

As for the endoscope 1, a diameter, a length, a material and the like of a shaft 2 is not particularly limited as long as the endoscope 1 can be inserted into a digestive tract of a living body for use.

For example, the diameter of the shaft 2 may be approximately 5 to 15 mm, whereas a diameter thereof in a general endoscope is approximately 10 mm. The length of the shaft 2 may be approximately 1200 to 3000 mm, whereas a length thereof in a general endoscope is approximately 1200 mm.

It is preferred that the endoscope 1 has functions of narrow band imaging (NBI), water jetting and the like particularly in the case of surgery on an organ in abdominal cavity.

(Description of Suturing Apparatus 10 in the Embodiment)

As shown in FIG. 1, the suturing apparatus 10 in the embodiment includes a front-rear pair of arms 11, 12, and arm moving means 13 for operating the front-rear pair of arms 11, 12.

As shown in FIG. 1, the suturing apparatus 10 in the embodiment is fixed to the endoscope 1 for use by fixing the arm moving means 13 to the shaft 2 of the endoscope 1.

The suturing apparatus 10 in the embodiment is attached to the shaft 2 of the endoscope 1 for use so that the front-rear pair of arms 11, 12 are both located ahead of a tip face 1s of the shaft 2 of the endoscope 1, and the rear arm 12 is located on a side of the tip face 1s of the endoscope 1 with respect to the front arm 11.

Moreover, the suturing apparatus 10 in the embodiment is attached so that axial directions of respective tubes 13a to 13c of the arm moving means 13 described later become substantially parallel with an axial direction of the shaft 2.

Thus, an incised part formed on a digestive tract such as a stomach can be sutured by using the front-rear pair of arms 11, 12, while movement of the front-rear pair of arms 11, 12 is checked by a camera of the endoscope 1.

Further, if the suturing apparatus 10 is attached so that the axial directions of the respective tubes 13a to 13c become substantially parallel with the axial direction of the shaft 2, the arm moving means 13 can smoothly cause the front-rear pair of arms 11, 12 to operate. An operator can also operate the front-rear pair of arms 11, 12 easily. When the shaft 2 is bent or the like, the arm moving means 13 can certainly follow the bend of the shaft 2. This can therefore prevent the arm moving means 13 from obstructing the bend or the like of the shaft 2.

The arm moving means 13 is not necessarily provided along the shaft 2 of the endoscope 1. Only a tip of the arm moving means 13 may be fixed to a tip of the shaft 2. In this case, the operator can also operate the front-rear pair of arms 11, 12 easily if an axial direction of the arm moving means 13 is substantially parallel with an axial direction of the tip of the shaft 2 at the tip of the shaft 2.

Each part of the suturing apparatus 10 in the embodiment will be described now.

The arm moving means 13 is first described.

Figure 2:
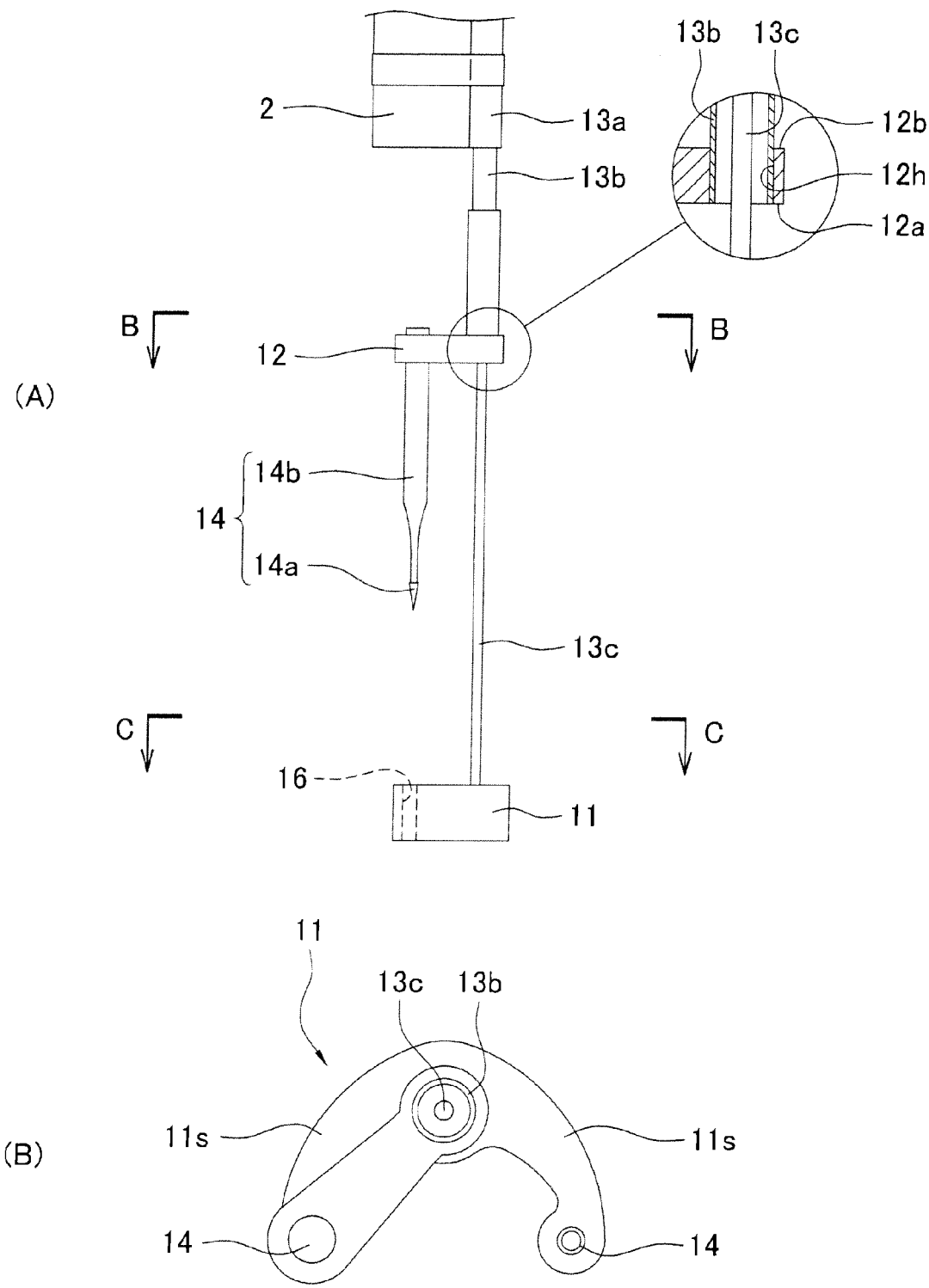
FIG. 2 shows (A): a schematic side view of the suturing apparatus 10 and (B): a fragmentary view taken in the direction of arrows B-B in (A).

As shown in FIGS. 1 and 2, the arm moving means 13 is a long member extending along the axial direction, which is attached to the shaft 2 of the endoscope 1. The arm moving means 13 is simply required to have a length to the same extent as that of the shaft 2 of the endoscope 1, not particularly limited.

The arm moving means 13 is fixed to the shaft 2. For example, as described above, the arm moving means 13 is fixed along the shaft 2, or fixed to the shaft 2 with only the tip of the arm moving means 13 fixed to the tip of the shaft 2.

A method for fixing the arm moving means 13 to the shaft 2 is not particularly limited as long as the arm moving means 13 can be fixed so as not to prevent deformation such as bend of the shaft 2. For example, the arm moving means 13 can be fixed by a belt-like member made of a material such as polyethylene, reinforced vinyl, reinforced plastics or aluminum, or an annular fastener made of a material such as polyethylene, reinforced vinyl or metal, but not particularly limited thereto.

The arm moving means 13 has flexibility to the extent of being able to bend following the bend of the shaft 2, while being fixed to the shaft 2. That is, the arm moving means 13 has strength so as not to prevent an operation of the endoscope 1 even if being attached to the shaft 2 of the endoscope 1.

More specifically, the arm moving means 13 includes three tubes (or two tubes and one wire) having the flexibility to the extent of being able to bend following the bend of the shaft 2. That is, the arm moving means 13 includes the case tube 13a, the rear-arm moving tube 13b and the front-arm moving tube 13c (or a front-arm moving wire).

The case tube 13a is a hollow tubular member fixed to the shaft 2 by a belt-like member or the like. A material of the case tube 13a is not particularly limited, however, the case tube 13a is preferably made of a material such as polyethylene or reinforced vinyl.

The rear-arm moving tube 13b is a hollow tubular member inserted into the case tube 13a. The rear-arm moving tube 13b is provided in the case tube 13a so as to be able to move along an axial direction of the case tube 13a and rotate around the axis. The rear arm 12 is connected to a tip of the rear-arm moving tube 13b. A material of the rear-arm moving tube 13b is not particularly limited. However, the rear-arm moving tube 13b is preferably made of a material such as polyethylene, reinforced vinyl or metal wire. Since the rotation of the rear-arm moving tube 13b causes the rear arm 12 to rock, it is preferred that, when the rear-arm moving tube 13b is rotated on a hand side, the rear-arm moving tube 13b can rock the rear arm 12 by the same amount of the rotation. For example, the rear-arm moving tube 13b is obtained by forming a tubular member with a plurality of metal wires arranged on a circumference of the same circle and whose axial directions are parallel with each other. As a result, the above function can be achieved.

The front-arm moving tube 13c is a tube inserted through the rear-arm moving tube 13b. The front-arm moving tube 13c can move along an axial direction of the rear-arm moving tube 13b and rotate around the axis in the rear-arm moving tube 13b. The front arm 11 is connected to a tip of the front-arm moving tube 13c. A material of the front-arm moving tube 13c is not particularly limited. However, it is preferred that rigidity is high at a part approximately 10 mm from the tip, and a part on the hand side with respect to the tip is flexible but does not expand/contract in an advance or retreat direction. For example, a tube whose tip on the order of 10 mm has a rod-like portion formed with metal or the like and having high rigidity and whose part except for the tip is formed with a wire or the like can be used as the front-arm moving tube 13c. Since a rotation of the front-arm moving tube 13c causes the front arm 11 to rock, it is preferred that, when the front-arm moving tube 13c is rotated on the hand side, the front-arm moving tube 13c can rock the front arm 11 by the same amount of the rotation.

Base ends of the front-arm moving tube 13c and the rear-arm moving tube 13b extend close to an operation portion for operating the shaft 2 of the endoscope 1. Therefore, movement of the tip of each tube (advance/retreat along the axial direction, rotation around the axis) can be operated by operating the base end of each tube.

With the above configuration of the arm moving means 13, the front-rear pair of arms 11, 12 can be moved closer to or away from each other when the front-arm moving tube 13c and the rear-arm moving tube 13b are simultaneously moved, or either of them is moved along the axial direction.

Moreover, when the front-arm moving tube 13c is rotated around an axis of the front-arm moving tube 13c, the front arm 11 can be rotated around the axis thereof. When the rear-arm moving tube 13b is rotated around an axis of the rear-arm moving tube 13b, the rear arm 12 can be rotated around the axis thereof.

The front-arm moving tube 13c is simply required to relatively move along the axial direction with respect to the rear-arm moving tube 13b. It is acceptable that the front-arm moving tube 13c cannot be rotated around the axis with respect to the rear-arm moving tube 13b. In this case, a central axis of a needle-like member 14 of the rear arm 12 described later can advantageously correspond to a central axis of a housing space 16 of the front arm 11 at all times.

The rear-arm moving tube 13b is also simply required to relatively move along the axial direction with respect to the case tube 13a. It is acceptable that the rear-arm moving tube 13b cannot be rotated around the axis with respect to the case tube 13a.

Further, it is preferred that the rear-arm moving tube 13b and front-arm moving tube 13c can independently move in the axial direction. However, either of them may move in the axial direction as long as the front-rear pair of arms 11, 12 can be moved closer to or away from each other.

An outside diameter of the arm moving means 13 (that is, an outside diameter of the case tube 13a) may be any length as long as the endoscope 1 with the suturing apparatus 10 in the embodiment can be inserted into a digestive tract (or into an over tube), not particularly limited. For example, as for the outside diameter of the arm moving means 13, a diameter obtained by adding the outside diameters of the arm moving means 13 and shaft 2 is preferably approximately 11 to 13 mm, and more preferably approximately 11 to 12 mm.
(Description of Front-Rear Pair of Arms 11, 12)

The front-rear pair of arms 11, 12 will be described now.
(Rear Arm 12)

The rear arm 12 is first described.

As shown in FIGS. 1 and 2, the rear arm 12 is a member formed into a rectangle-like shape. A front face 12a and a back face 12b are flat surfaces parallel with each other.

The tip of the rear-arm moving tube 13b is connected to a base end of the rear arm 12. The rear-arm moving tube 13b is connected to the rear arm 12 so that a central axis of the rear-arm moving tube 13b is perpendicular to the front face 12a and the back face 12b of the rear arm 12 at the connection part with the rear arm 12. Hereinafter, the central axis of the rear-arm moving tube 13b at the connection part between the rear-arm moving tube 13b and the rear arm 12 is simply referred to as a central axis of the tip of the rear-arm moving tube 13b.

A through hole 12h extending between the front face 12a and the back face 12b is formed at the base end of the rear arm 12. The central axis of the tip of the rear-arm moving tube 13b is substantially coaxial with a central axis of the through hole 12h. The reason will be described later.

A tip of the rear arm 12 is provided with the needle-like member 14. The needle-like member 14 includes a shaft portion 14b, and a part provided at an end of the shaft portion 14b and having a longer outside diameter than the end does (arrowhead-like portion 14a). In the arrowhead-like portion 14a, an outside diameter of a base end thereof is longer than that of the end of the shaft portion 14b, thereby providing a step at a connection part with the shaft portion 14b. As described later, the arrowhead-like portion 14a becomes resistant when the needle-like member 14 is pulled out from an engagement member 21. The arrowhead-like portion 14a of the needle-like member 14 corresponds to an expanded diameter portion in Claims.

The needle-like member 14 is attached to the rear arm 12 so that a tip of the needle-like member 14 faces to the front arm 11 and an axial direction thereof is perpendicular to the front face 12a. In other words, the needle-like member 14 is attached to the rear arm 12 so that a central axis of the needle-like member 14 becomes parallel with the central axis of the tip of the rear-arm moving tube 13b.

With the above structure, the rear arm 12 can be rocked around the central axis of the rear-arm moving tube 13b when the rear-arm moving tube 13b is rotated around the central axis. The central axis of the needle-like member 14 is in parallel with the central axis of the tip of the rear-arm moving tube 13b. Therefore, the needle-like member 14 can be rotated around the central axis of the tip of the rear-arm moving tube 13b, while the central axis of the needle-like member 14 is maintained in parallel with the central axis of the tip of the rear-arm moving tube 13b.

The central axis of the tip of the rear-arm moving tube 13b corresponds to a rocker shaft in Claims.

When the rear-arm moving tube 13b is rotated around the central axis, the rear arm 12 is simply required to be able to rotate, while the central axis of the needle-like member 14 is maintained in parallel with the central axis of the tip of the rear-arm moving tube 13b. That is, the surface of the rear arm 12 (the front face 12a or the back face 12b) is not necessarily flat. Further, the back face 12b of the rear arm 12 is not necessarily perpendicular to the central axis of the tip of the rear-arm moving tube 13b.

A position at the rear arm 12 on which the needle-like member 14 is provided is not particularly limited. The needle-like member 14 may be provided at any position as long as being provided at a position apart from the central axis of the tip of the rear-arm moving tube 13b. The needle-like member 14 is not necessarily provided at the tip of the rear arm 12.

The needle-like member 14 is simply required to have a length and strength to the extent that the needle-like member 14 can be stuck into and pass through an object to be sutured, and further, the needle-like member 14 can be moved in an opposite direction in the state of having passed through the object to be pulled out from the object. A material, length and shaft diameter of the needle-like member 14 is not particularly limited. In the case of suturing a gastric wall with the suturing apparatus 10 in the embodiment, for example, a length from the front face of the rear arm 12 to the tip of the needle-like member 14 may be long enough to pass through the gastric wall. The material of the needle-like member 14 is preferably metal in terms of strength. In a state of attaching the needle-like member 14 to the rear arm 12, for example, the length of the front face of the rear arm 12 to the tip of the needle-like member 14 is preferably approximately 7 to 20 mm, and more preferably approximately 7 to 10 mm. As for the shaft diameter of the needle-like member 14, a shaft diameter of the base end of the shaft portion 14b is preferably approximately 0.5 to 1 mm, and a shaft diameter of the end of the shaft portion 14b is preferably approximately 0.5 to 1 mm, and a maximum diameter of the arrowhead-like portion 14a is preferably approximately in a range within the shaft diameter of the end of the shaft portion 14b±0.1 to 1 mm.

(Front Arm 11)

The front arm 11 will be described now.

As shown in FIGS. 1 and 2, the front arm 11 is a member having a pair of rectangle-like parts (hereinafter, referred to as a branch portion 11s), and is formed into an almost V shape by connecting base ends of the pair of branch portions 11s. As for the front arm 11, a back face 11b (that is, a surface on a side of the rear arm 12) is formed into a flat surface.

The front arm 11 may be formed into an almost arc or almost rectangle (U shape or the like) not limited to the almost V shape as long as the pair of branch portions 11s is provided.

The tip of the front-arm moving tube 13c is connected to a part where the pair of branch portions 11s are connected to each other in the front arm 11. The front-arm moving tube 13c is connected to the front arm 11 so that a central axis of the front-arm moving tube 13c is perpendicular to the back face 11b of the front arm 11 in the connection part with the front arm 11. Hereinafter, the central axis of the front-arm moving tube 13c at the connection part between the front-arm moving tube 13c and the front arm 11 is simply referred to as a central axis of the tip of the front-arm moving tube 13c.

Figure 3:
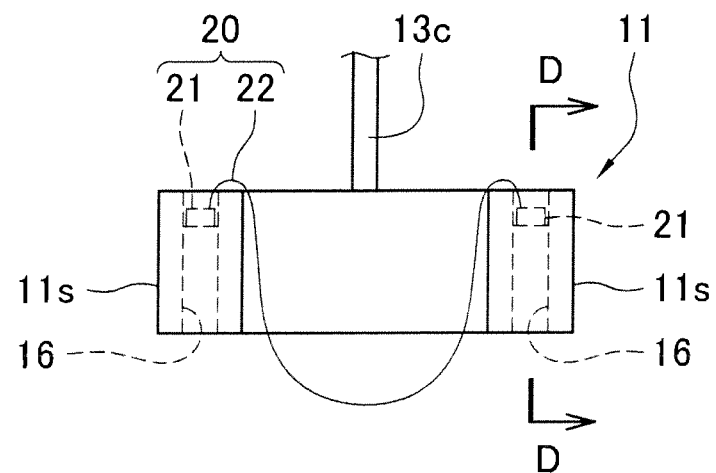
FIG. 3 shows schematic enlarged views of a main part of a front arm 11.
Figure 3:
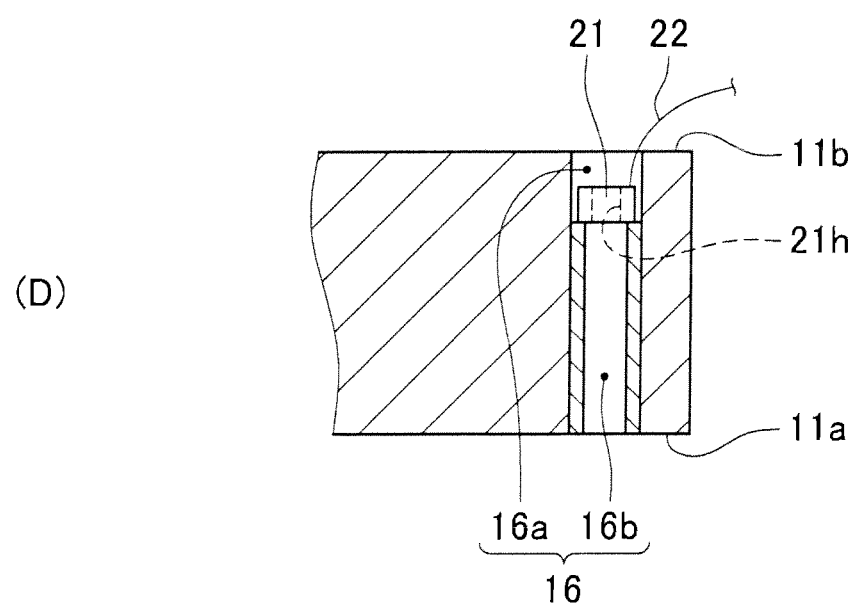

As shown in FIGS. 1 and 3, a pair of housing spaces 16, 16 is formed at tips of the pair of branch portions 11s provided on the front arm 11. Each of the housing spaces 16 is a through hole extending between a front face 11a and the back face 11b of the branch portion 11s. A central axis of the housing space 16 is in parallel with the central axis of the tip of the front-arm moving tube 13c. The housing space 16 is a stepped hole in which an inside diameter of a part on a back face 11b side (major diameter portion 16a) is longer than an inside diameter of a part on a front face 11a side (minor diameter portion 16b). The inside diameter of the minor diameter portion 16b is longer than the outside diameter of the arrowhead-like portion 14a. The reason why the housing space 16 is formed into such a shape will be described later.

In the housing space 16, a distance from the central axis thereof to the central axis of the tip of the front-arm moving tube 13c is equal to a distance from the central axis of the needle-like member 14 to the central axis of the tip of the rear-arm moving tube 13b.

As described above, since the central axis of the tip of the rear-arm moving tube 13b is substantially coaxial with the central axis of the through hole 12h, the central axis of the tip of the front-arm moving tube 13c can be coaxial with the central axis of the tip of the rear-arm moving tube 13b. In other words, the central axis of the tip of the front-arm moving tube 13c can be coaxial with the rocker shaft.

Because of this, when the rear-arm moving tube 13b is rotated around the central axis, the central axis of the needle-like member 14 can be coaxial with the central axis of each of the housing spaces 16. Therefore, in a state where both of the central axes are coaxial with each other, when the front arm 11 and the rear arm 12 are moved closer to each other, the arrowhead-like portion 14a of the needle-like member 14 can be inserted into the housing space 16.

The front arm 11 may be provided in any manner as long as the central axis of each of the housing spaces 16 is in parallel with the central axis of the tip of the front-arm moving tube 13c. That is, the back face 11b of the front arm 11 is not necessarily formed into a flat surface. Further, the back face 12b of the rear arm 12 is not necessarily perpendicular to the central axis of the tip of the front-arm moving tube 13c.

The housing space 16 may be provided at any position as long as the distance from the central axis of the housing space 16 to the central axis of the tip of the front-arm moving tube 13c is equal to the distance from the central axis of the needle-like member 14 to the central axis of the tip of the rear-arm moving tube 13b. The housing space 16 is not necessarily provided at the tip of the front arm 11.

(Suturing Instrument 20)

As shown in FIG. 3, the suturing apparatus 10 in the embodiment includes a suturing instrument 20. The suturing instrument 20 includes a pair of engagement members 21, 21 formed into an annular shape, and a suture thread 22 connecting the pair of engagement members 21, 21.

Each of the pair of engagement members 21, 21 in the suturing instrument 20 is provided in each of the pair of housing spaces 16, 16 in the front arm 11.

The engagement member 21 is formed in a size to the extent that a through hole 21h extending through both sides of the engagement member 21 is provided above a hole extending through the minor diameter portion 16b of the housing space 16 when the engagement member 21 is provided in the housing space 16. More specifically, an outside diameter of the engagement member 21 is shorter than the inside diameter of the major diameter portion 16a of the housing space 16 and longer than the inside diameter of the minor diameter portion 16b. Moreover, when the engagement member 21 is provided in the housing space 16, a distance between an outer edge of the engagement member 21 and an inner face of the major diameter portion 16a is shorter than a radius of the through hole 21h. That is, as for the size of the engagement member 21, only a small gap is formed between the outer edge of the engagement member 21 and the inner face of the major diameter portion 16a when the engagement member 21 is provided in the housing space 16.

The through hole 21h of the engagement member 21 allows the arrowhead-like portion 14a of the needle-like member 14 to be inserted therethrough. However, when the arrowhead-like portion 14a is completely inserted through the through hole 21h, the engagement member 21 does not come out of the needle-like member 14. More specifically, an inside diameter of the engagement member 21 is shorter than the outside diameter of the arrowhead-like portion 14a of the needle-like member 14, but is longer than a shaft diameter of the end of the shaft portion 14b in the needle-like member 14 (that is, a connection part with the arrowhead-like portion 14a).

(Brief Description of Operation of Suturing Apparatus 10 in the Embodiment)

In the suturing apparatus 10 in the embodiment with the above configuration, when the front arm 11 is rocked by operating the arm moving means 13, the needle-like member 14 and one housing space 16 face to each other allowing the needle-like member 14 to become coaxial with the one housing space 16. When the arm moving means 13 causes the front arm 11 and the rear arm 12 to move closer to each other in such a state, the arrowhead-like portion 14a of the needle-like member 14 can be inserted into the one housing space 16.

Since the one housing space 16 is provided with one engagement member 21 of the suturing instrument 20, the arrowhead-like portion 14a of the needle-like member 14 can be inserted through the one engagement member 21. The front arm 11 and the rear arm 12 are then moved closer to each other until the whole arrowhead-like portion 14a of the needle-like member 14 is inserted into the minor diameter portion 16b of the one housing space 16. In that case, the needle-like member 14 can pass through the one engagement member 21 up to the shaft portion 14b.

When the front arm 11 and the rear arm 12 are moved away from each other by operating the arm moving means 13 in such a state, the engagement member 21 can be removed from the housing space 16 together with the needle-like member 14.

The front arm 11 is then rocked by operating the arm moving means 13, and thereby the needle-like member 14 becomes coaxial with the other housing space 16.

The other housing space 16 is provided with the other engagement member 21 of the suturing instrument 20. In such a state, the front arm 11 and the rear arm 12 are moved closer to each other until the whole arrowhead-like portion 14a of the needle-like member 14 is inserted into the minor diameter portion 16b of the other housing space 16. In that case, the needle-like member 14 can pass through the other engagement member 21 up to the shaft portion 14b.

When the front arm 11 and the rear arm 12 are moved away from each other by operating the arm moving means 13, the pair of engagement members 21, 21 is engaged with the needle-like member 14. Therefore, the suture thread 22 connecting the pair of engagement members 21, 21 can be formed into a loop (see FIG. 5 (8)).

In the suturing apparatus 10 in the embodiment, the front arm 11 and the rear arm 12 are moved closer to and away from each other twice and a position of an object through which the needle-like member 14 is inserted for the first time is different from that of for the second time, while the object is provided between the front arm 11 and the rear arm 12. In that case, the suture thread 22 can pass through the object so that both ends of the suture thread 22 are located on the same side of the object. In other words, the suture thread 22 can pass through the object so that a part between the both ends of the suture thread 22 is caught in the object (see FIG. 5(8)).

(Suturing Living Body with Suturing Apparatus 10 in the Embodiment)

According to the above configuration, when the suturing apparatus 10 in the embodiment is attached to the shaft 2 of the endoscope 1, an incised part in the gastric wall or the like can be sutured at the stomach.

Hereinafter, a suturing operation of an incised part with the suturing apparatus 10 in the embodiment will be described with reference to FIGS. 4 and 5.

Hereinafter, suturing of an incised part SH formed in a gastric wall will be described.

The shaft 2 of the endoscope 1 having the suturing apparatus 10 in the embodiment attached thereto is first inserted into a stomach to provide a tip face of the shaft 2 in the vicinity of the incised part SH to be sutured. In such a state, only the front arm 11 is inserted into the incised part SH by operating the front-arm moving tube 13c of the arm moving means 13.

Figure 4:
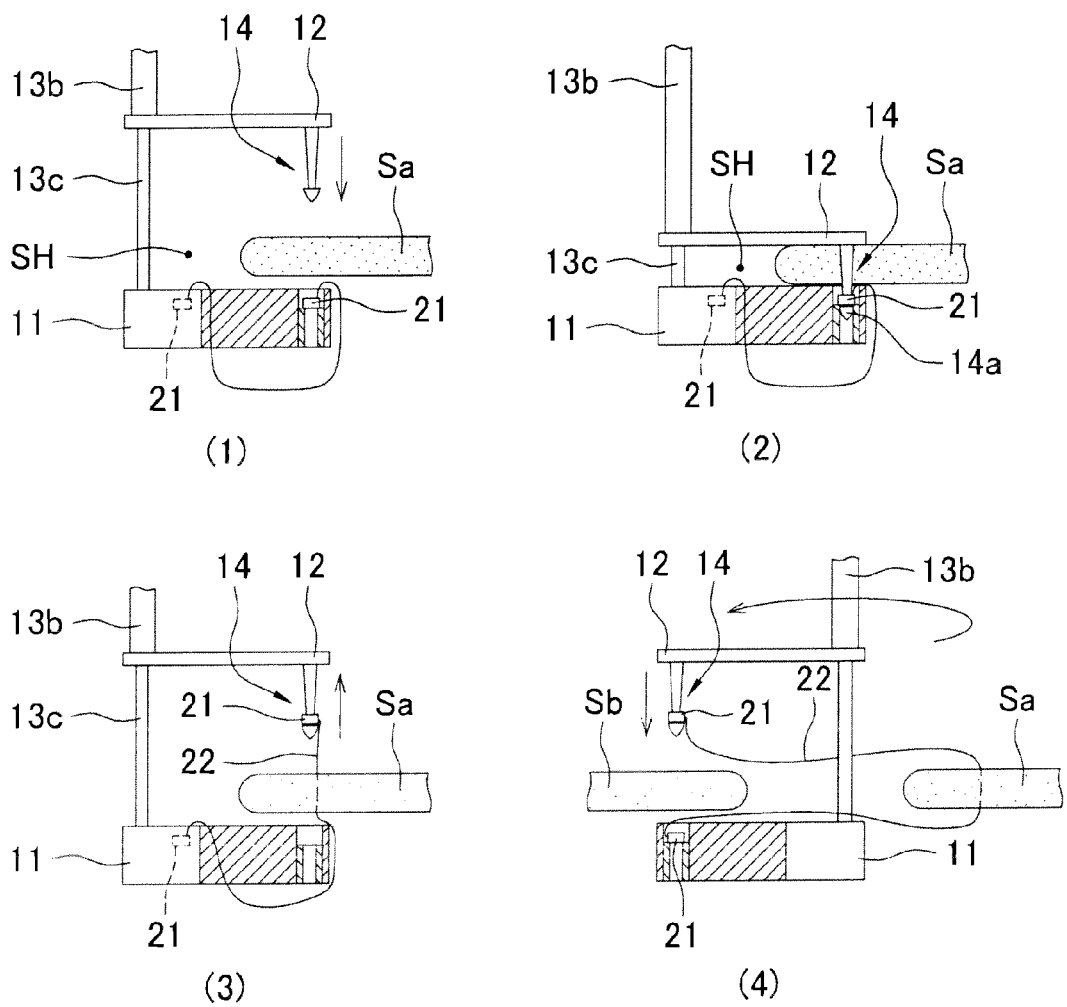
FIG. 4 shows schematic views illustrating a suturing operation with the suturing apparatus 10 in the embodiment.
Figure 5:
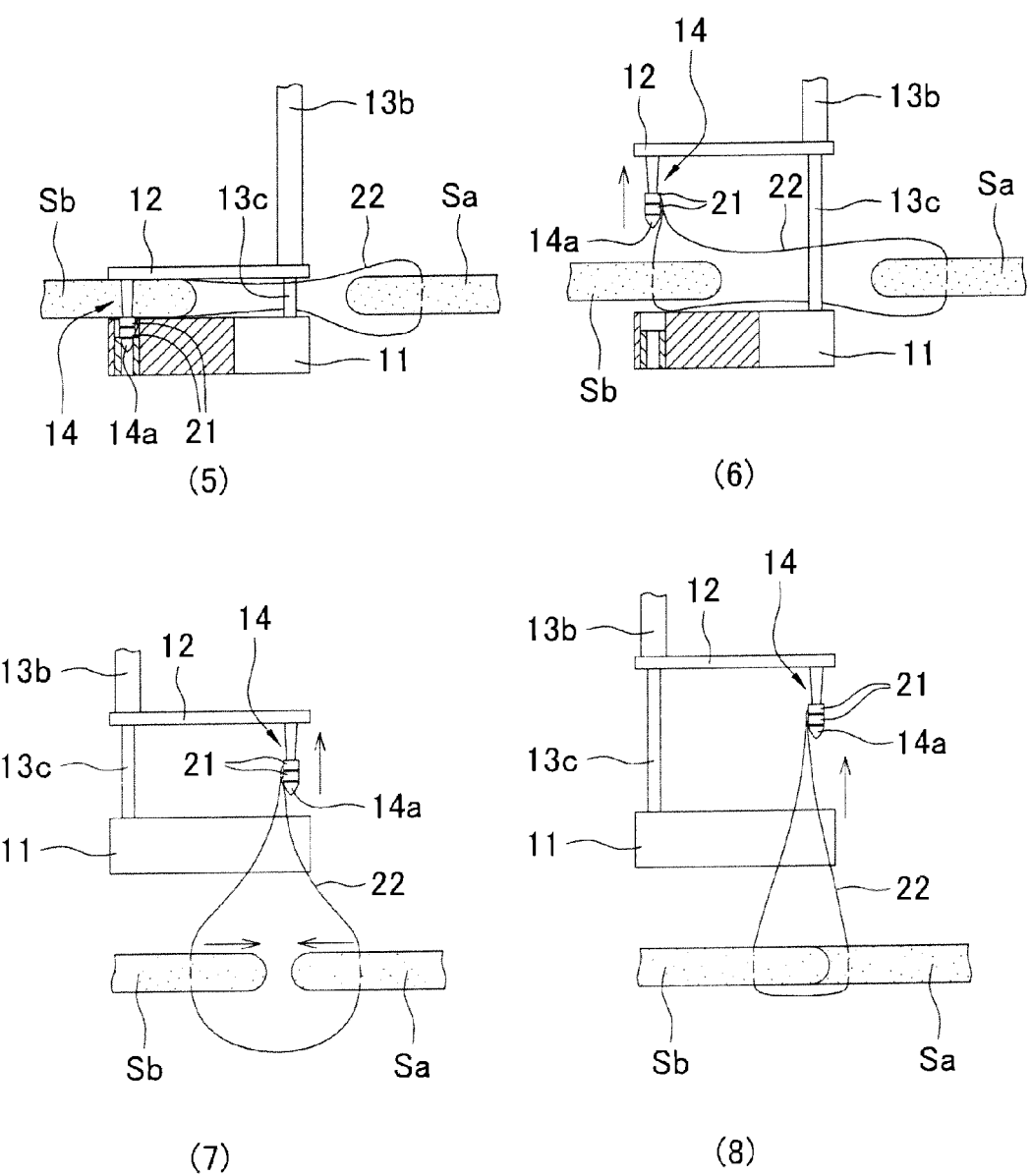
FIG. 5 shows schematic views illustrating the suturing operation with the suturing apparatus 10 in the embodiment.

After that, the front arm 11 and the rear arm 12 are provided by operating the rear-arm moving tube 13b and the front-arm moving tube 13c of the arm moving means 13 so that one edge Sa of the incised part SH is sandwiched between one branch portion 11s of the front arm 11 and the back face 12b of the rear arm 12 (FIG. 4 (1)).

Obviously, the front arm 11 and the rear arm 12 are provided so that the needle-like member 14 becomes coaxial with the housing space 16 (one housing space 16) formed in the one branch portion 11s.

In the state of FIG. 4 (1), the rear arm 12 is moved closer to the front arm 11 by operating the rear-arm moving tube 13b of the arm moving means 13. This allows the needle-like member 14 to be inserted through the one edge Sa, thereby allowing the arrowhead-like portion 14a of the needle-like member 14 to be inserted into the one housing space 16. Since the arrowhead-like portion 14a of the needle-like member 14 can pass through one engagement member 21 of the suturing instrument 20, the one engagement member 21 can be engaged with the needle-like member 14 (FIG. 4 (2)).

In FIG. 4, the description has been made on the case where the rear arm 12 approaches the front arm 11 at the time of moving the rear arm 12 and the front arm 11 closer to each other. However, the front arm 11 may approach the rear arm 12, or both of them may be moved together to come closer to each other. This point is similar to the case where the rear arm 12 and the front arm 11 are moved away from each other in the following description. Accordingly, hereinafter, a description is made only on the case where the rear arm 12 is moved with respect the front arm 11. The description is omitted on the other cases (the case where the front arm 11 is moved with respect to the rear arm 12, and the case where both of them are moved together).

When the one engagement member 21 is engaged with the arrowhead-like portion 14a of the needle-like member 14, the rear arm 12 is moved away from the front arm 11 by operating the rear-arm moving tube 13b of the arm moving means 13. At this time, the needle-like member 14 returns to an inside of stomach through a hole (hereinafter, referred to as a first perforated hole) formed at the time of inserting the needle-like member 14 through the one edge Sa. Then, the one engagement member 21 engaged with the needle-like member 14 also moves to the inside of stomach together with the needle-like member 14.

On the other hand, the other engagement member 21 of the suturing instrument 20 remains in the housing space 16 formed in the other branch portion 11s even if the one engagement member 21 moves. The suture thread 22 connecting both of the engagement members 21 is therefore provided so as to pass through the first perforated hole. That is, one end of the suture thread 22 fixed to the one engagement member 21 is inside the stomach, whereas the other end of the suture thread 22 fixed to the other engagement member 21 is outside the stomach (FIG. 4 (3)).

In the state of FIG. 4 (3), the front arm 11 and the rear arm 12 are provided so that the other edge Sb of the incised part SH is sandwiched between the other branch portion 11s of the front arm 11 and the back face 12b of the rear arm 12 (FIG. 4 (4)). More specifically, the other branch portion 11s is provided on an outer face of the other edge Sb by moving the front arm 11. By rocking the front arm 11 then, the needle-like member 14 becomes coaxial with the housing space 16 (the other housing space 16) formed in the other branch portion 11s.

In the state of FIG. 4 (4), the rear arm 12 is moved closer to the front arm 11 by operating the rear-arm moving tube 13b of the arm moving means 13. This allows the needle-like member 14 to be inserted through the other edge Sb, thereby allowing the arrowhead-like portion 14a of the needle-like member 14 to be inserted into the other housing space 16. Since the arrowhead-like portion 14a of the needle-like member 14 can pass through the other engagement member 21 of the suturing instrument 20, the other engagement member 21 can also be engaged with the needle-like member 14 (FIG. 5 (5)).

When the other engagement member 21 is engaged with the needle-like member 14, the rear arm 12 is moved away from the front arm 11 by operating the rear-arm moving tube 13b of the arm moving means 13. In that case, the needle-like member 14 returns to the inside of stomach through a hole (hereinafter, referred to as a second perforated hole) formed at the time of inserting the needle-like member 14 through the other edge Sb. Then, the other engagement member 21 engaged with the needle-like member 14 also moves to the inside of stomach together with the needle-like member 14, thereby the suture thread 22 passing through the second perforated hole (FIG. 5 (6)).

Each of the pair of engagement members 21 having each end of the suture thread 22 fixed thereto is engaged with the one needle-like member 14. Therefore, the suture thread 22 is formed into a loop extending from the needle-like member 14 (that is, the inside of stomach) to the outside of stomach through the first perforated hole and returning from the outside of stomach to the needle-like member 14 (that is, the inside of stomach) through the second perforated hole (see FIG. 5 (7)).

When the above loop of the suture thread 22 is formed, the front arm 11 is first moved into the stomach through the incised part SH by operating the arm moving means 13. When the front arm 11 enters the stomach, the shat 2 itself or the rear arm 12 is moved so that the needle-like member 14 is moved away from the incised part SH. Since the both ends of the suture thread 22 are moved away from the incised part SH, the pair of edges Sa, Sb of the incised part SH are moved so that a length of a part in the suture thread 22 becomes shorter. The part in the suture thread 22 is located between a part having passed through the first perforated hole and a part having passed through the second perforated hole, and is located outside the stomach. That is, the pair of edges Sa, Sb of the incised part SH is moved so that end faces thereof come close to each other. As a result, the incised part SH is sutured so that the end faces of the edges Sa, Sb come in contact with each other (FIG. 5 (8)).

When the end faces of the pair of edges Sa, Sb in the incised part SH come in contact with each other, the suture thread 22 is fastened in such a state. More specifically, in the suture thread 22, a part extending from the needle-like member 14 (that is, the one engagement member 21) to the first perforated hole and a part extending from the needle-like member 14 (that is, the other engagement member 21) to the second perforated hole are fastened together. A commercially available clip or the like can be used for the thread-fastening. For example, the clip or the like is supplied from a forceps port of the endoscope 1 to be attached to the suture thread 22, thereby enabling the thread-fastening.

Finally, when, in the suture thread 22, a part located on a side of the needle-like member 14 with respect to the fastened part is cut, the incised part SH can be fixed with the end faces of the pair of edges Sa, Sb in the incised part SH in contact with each other.

The description has been made on the case of one needle-like member 14 provided on the rear arm 12 of the suturing apparatus 10 in the above example, however, a plurality of needle-like members 14 may be provided.

For example, a plurality of needle-like members 14 are arranged at intervals along the axial direction of the front arm 11. Each of the branch portions 11s is provided with a plurality of housing spaces 16 at positions corresponding to the plurality of needle-like members 14. That is, each of the branch portions 11s is provided with the plurality of housing spaces 16 in the following manner. When a central axis of one needle-like member 14 becomes coaxial with a central axis of one housing space 16 provided on one branch portion 11s, all of the needle-like members 14 becomes coaxial with all of the housing space 16 provided on the one branch portion 11s. If suturing is performed with the suturing apparatus 10 according to the above procedure, a loop of the suture thread 22 inserted through the pair of edges Sa, Sb of the incised part SH can be formed at a plurality of positions at one time. This therefore enables suturing the incised part SH for a short time.

Although the description has been made on the case of two branch portions 11s in the above example, the number of the branch portions 11s to be provided on the front arm 11 may be three or more.

(Connection Mechanism)

Assuming that, in the suturing apparatus 10 having the above structure, the back face 11b of the front arm 11 and the front face 12a of the rear arm 12 are both flat, the back face 11b of the front arm 11 is perpendicular to the central axis of the tip of the front-arm moving tube 13c, and the front face 12a of the rear arm 12 is perpendicular to the central axis of the tip of the rear-arm moving tube 13b. The needle-like member 14 can be easily inserted into the housing space 16 when the central axis of the needle-like member 14 becomes coaxial with the central axis of the housing space 16. This can happen if the front arm 11 and the rear arm 12 can be moved closer to or away from each other with the back face 11b of the front arm 11 in parallel with the front face 12a of the rear arm 12. This is because, although a length how long the front-arm moving tube 13c protrudes from the tip of the rear-arm moving tube 13b is not limited, approximately 10 to 20 mm at longest thereof is enough to be protruded at the time of suturing a living body (such as a gastric wall). The part protruding in the front-arm moving tube 13c hardly bends due to such amount of the protrusion. Moreover, the front-arm moving tube 13c is inserted through the rear-arm moving tube 13b to be coaxial with each other. Because of this, even if the front arm 11 and the rear arm 12 are moved closer to or away from each other, the back face 11b of the front arm 11 is maintained in parallel with the front face 12a of the rear arm 12. The back face 11b of the front arm 11 can be certainly maintained in parallel with the front face 12a of the rear arm 12, particularly when the above described rod-like portion having high rigidity is provided at the tip of the front-arm moving tube 13c and a length of the rod-like portion is longer than the amount of protrusion by which the front-arm moving tube 13c protrudes.

However, with the following connection mechanism, the needle-like member 14 can be certainly inserted into the housing space 16, preferably.

Figure 6:
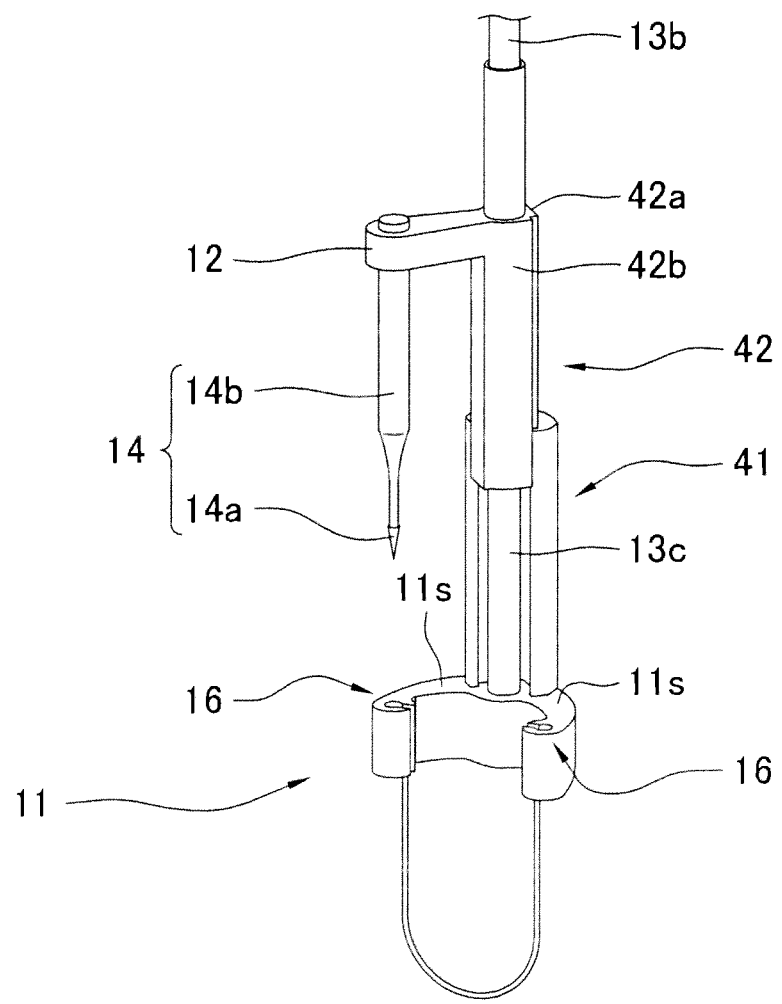
FIG. 6 is a schematic view of the endoscope 1 having the suturing apparatus 10 in another embodiment.
Figure 7:
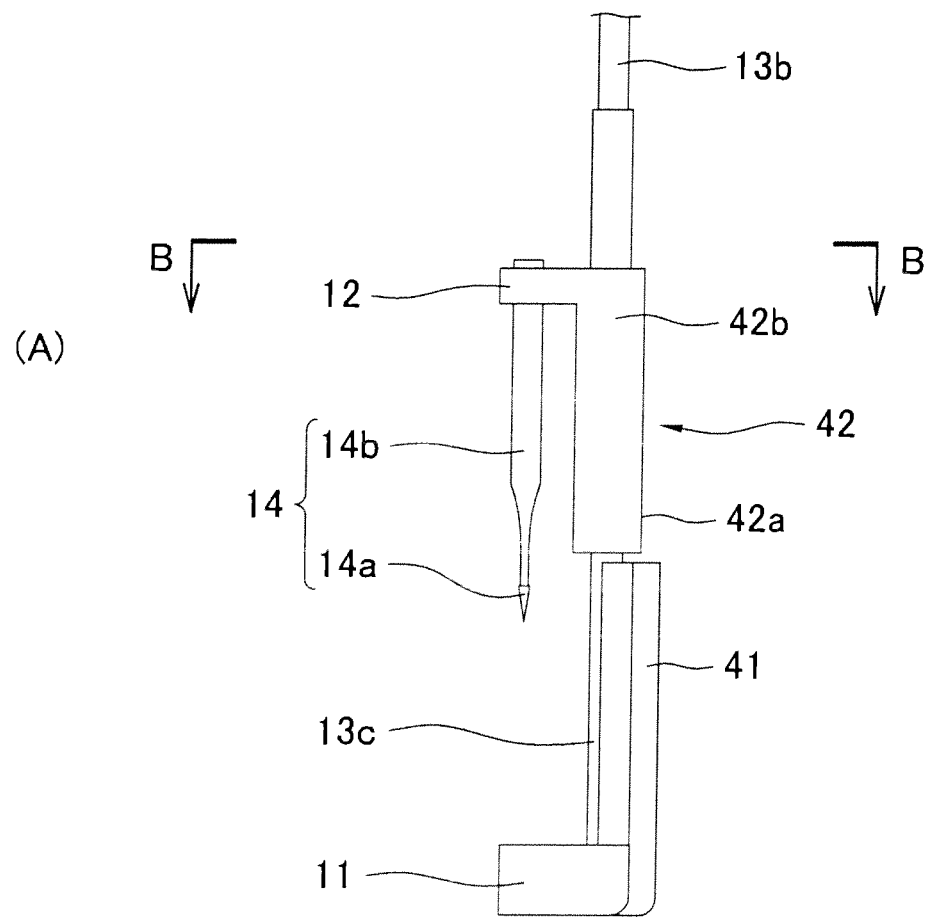
FIG. 7 shows (A): a schematic side view of the suturing apparatus 10 and (B): a fragmentary view taken in the direction of arrows B-B in (A).
Figure 7:
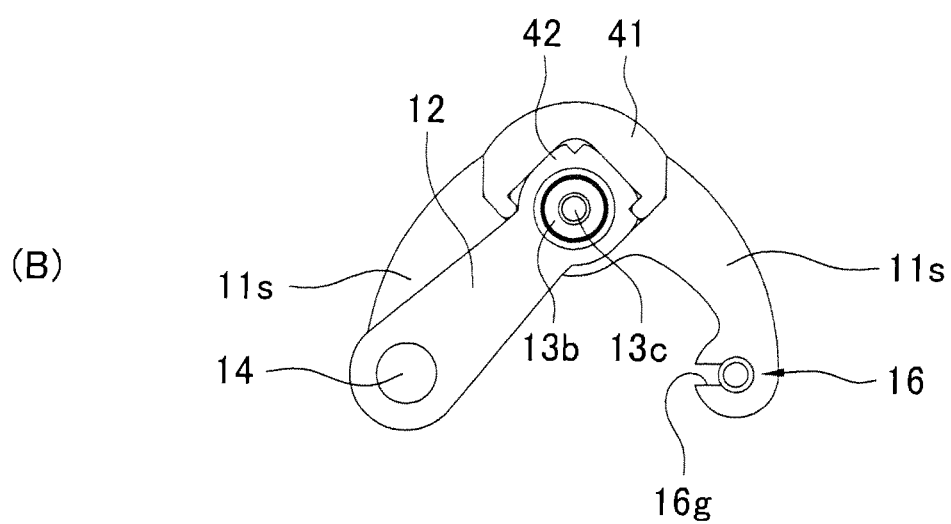
Figure 8:
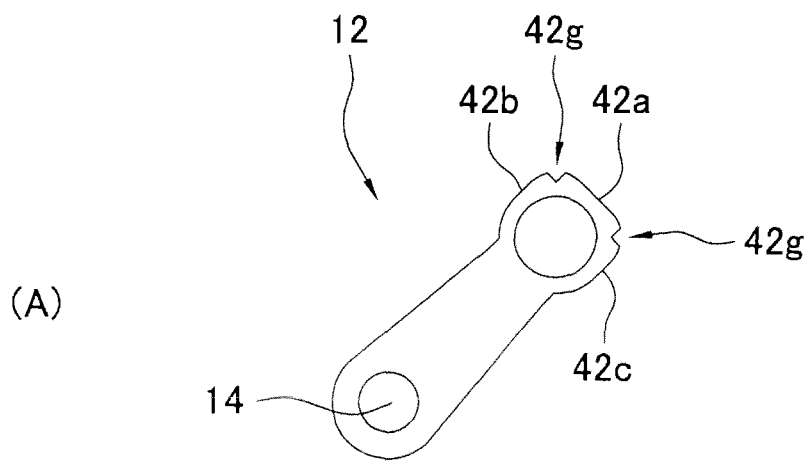
FIG. 8 shows (A): a schematic plan view of a rear arm 12 alone and (B): a schematic plan view of the front arm 11 alone.
Figure 8:
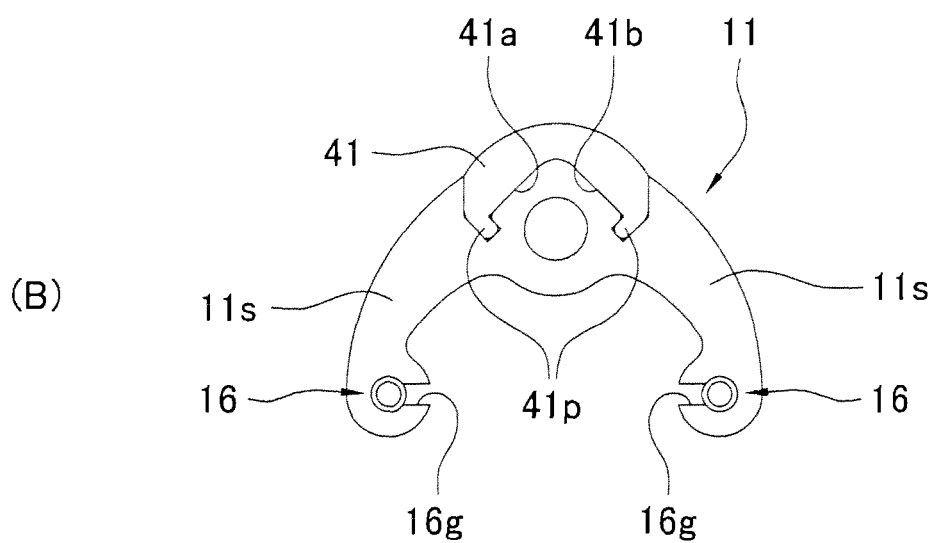
Figure 9:
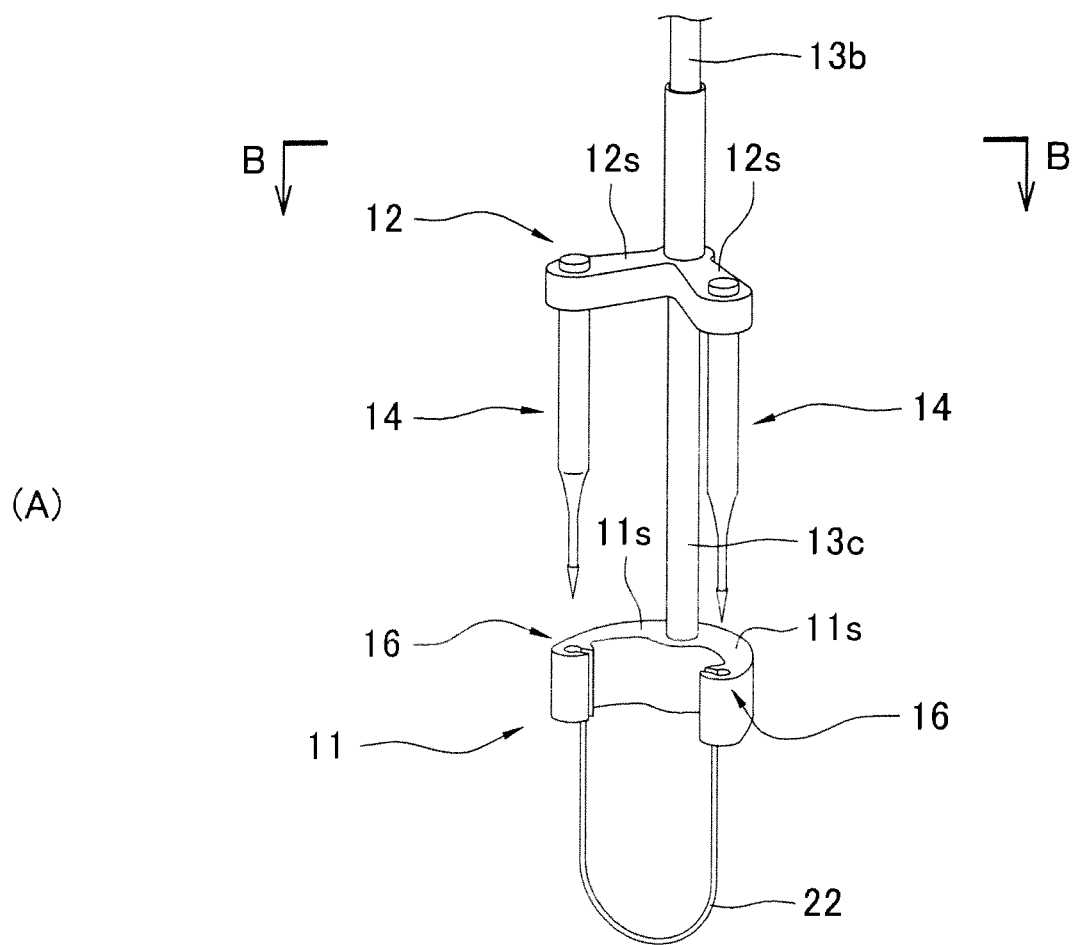
FIG. 9 shows (A): a schematic view of the endoscope 1 having the suturing apparatus 10 in another embodiment and (B): a fragmentary view taken in the direction of arrows B-B in (A).
Figure 9:
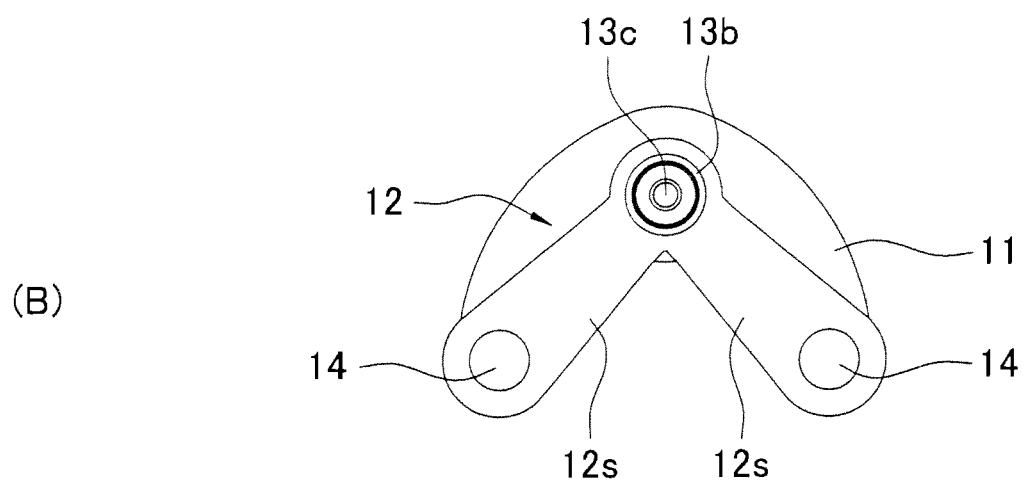

As shown in FIGS. 6 to 8, a connection mechanism 40 includes a rear connection member 42 provided on the rear arm 12 and a front connection member 41 provided on the front arm 11.

The rear connection member 42 is provided on the base end of the rear arm 12. This rear connection member 42 is a shaft-like portion having a section thereof formed into a square. A side face of the rear connection member 42 is formed into a flat surface in parallel with the rocker shaft (in other words, the central axis of the tip of the rear-arm moving tube 13b).

More specifically, the rear connection member 42 includes a reference side face 42a in parallel with the axial direction of the rocker shaft, and a pair of positioning side faces 42b, 42c each of which intersects with the reference side face 42a. The reference side face 42a is located on an opposite side of the needle-like member 14. The pair of positioning side faces 42b, 42c are flat surfaces in parallel with the axial direction of the rocker shaft. Since the section of the rear connection member 42 is a square, the reference side face 42a is perpendicular to the pair of positioning side faces 42b, 42c.

As shown in FIGS. 6 to 8, the front connection member 41 is a shaft-like portion provided on the base end of the front arm 11. The front connection member 41 includes a guide groove 41h formed along an axial direction of the front connection member 41. The guide groove 41h can be engaged with the rear connection member 42, and further, the engaged rear connection member 42 can be moved along the axial direction of the guide groove 41h.

More specifically, the guide groove 41h includes a pair of guide faces 41a, 41b intersecting with each other. The pair of guide faces 41a, 41b are formed into flat surfaces in parallel with the axial direction of the rocker shaft (in other words, the central axis of the tip of the front-arm moving tube 13c). In the pair of guide faces 41a, 41b, an intersection angle thereof is the same as an angle which the reference side face 42a of the rear connection member 42 forms with the pair of positioning side faces 42b, 42c. That is, the pair of guide faces 41a, 41b are perpendicular to each other.

When the rear connection member 42 is engaged with the guide groove 41h so that the reference side face 42a of the rear connection member 42 comes into surface contact with the guide face 41a or 41b, either one of the pair of positioning side faces 42b, 42c comes in surface contact with the guide face 41a or 41b. This causes the central axis of the needle-like member 14 to become coaxial with the central axis of either one of the housing space 16. In FIG. 7, the positioning side face 42b comes in surface contact with the guide face 41a when the reference side face 42a of the rear connection member 42 comes in surface contact with the guide face 41b. Then, the rear connection member 42 is positioned so that the central axis of the needle-like member 14 becomes coaxial with the central axis of one housing space 16 (the housing space 16 on the left side in FIG. 7(B)). On the contrary, the positioning side face 42c comes in surface contact with the guide face 41b when the reference side face 42a of the rear connection member 42 comes in surface contact with the guide face 41a. Then, the central axis of the needle-like member 14 is positioned so as to become coaxial with the central axis of the other housing space 16 (the housing space 16 on the right side in FIG. 7(B)).

With the above configuration, the rear connection member 42 can be moved to the front arm 11 along the guide groove 41h when the rear connection member 42 of the connection mechanism 40 is engaged with an end of the front connection member 41 on the side of the rear arm 12. Then, the rear connection member 42 can come in surface contact with the guide groove 41h at two faces. Therefore, the rear arm 12 and the front arm 11 can be moved closer to or away from each other in a state where a relative rotation of the rear arm 12 and the front arm 11 is fixed, that is, the rear arm 12 and the front arm 11 are positioned. Accordingly, the needle-like member 14 can approach the housing space 16 with the central axis of the needle-like member 14 coaxial with the central axis of the housing space 16. Therefore, the arrowhead-like portion 14a of the needle-like member 14 can be certainly and easily inserted into the housing space 16.

As shown in FIGS. 7 and 8, the pair of guide faces 41a, 41b of the guide groove 41h may be each provided with a rail type protrusion 41p extending along each of the guide faces 41a, 41b. The rear connection member 42 may be provided with grooves 42g capable of being engaged with the protrusions 41p. In this case, the rear connection member 42 and the front connection member 41 can be more certainly positioned. In other words, the rear arm 12 and the front arm 11 can be advantageously and certainly positioned.

FIG. 7 shows a structure in which a normal direction of the reference side face 42a is in parallel with a line connecting the central axis of the needle-like member 14 and the rocker shaft. However, the normal direction of the reference side face 42a may have an angle to some extent with respect to the line connecting the central axis of the needle-like member 14 and the rocker shaft as long as the above described function is achieved.

A structure of the connection mechanism is not limited to the above. The structure may be any as long as rocking of the rear arm 12 with respect to the front arm 11 is fixed, however, the movement in the direction in which the rear arm 12 and the front arm 11 are moved closer to or away from each other is allowed in a state where the central axis of the needle-like member 14 is coaxial with the central axis of the housing space 16.

(Description of Suturing Apparatus in Another Embodiment)

Although the description has been made on the case where the branch portion 11s is provided only on the front arm 11 in the above example, a pair of branch portions 12s, 12s may be provided on the rear arm 12. In this case, each of the branch portions 12s is provided with the needle-like member 14 in the following manner. When a central axis of one needle-like member 14 becomes coaxial with a central axis of one housing space 16, a central axis of the other needle-like member 14 becomes coaxial with a central axis of the other housing space 16. Then, the pair of housing spaces 16, 16 is respectively provided with a pair of engagement members 21, 21. The pair of engagement members 21, 21 can be respectively engaged with the needle-like members 14 provided on the pair of branch portions 12s, 12s by moving the front arm 11 and the rear arm 12 closer to and away from each other only once. Therefore, a loop of the suture thread 22 can be formed so that the needle-like member 14 provided on one branch portion 12s is connected to the needle-like member 14 provided on the other branch portion 12s.

For example, in the case of suturing the pair of edges Sa, Sb of the incised part SH with such a suturing apparatus 10, the pair of edges Sa, Sb is each located between the pair of branch portions 11s, 11s of the front arm 11 and the pair of branch portions 12s, 12s of the rear arm 12. When the front arm 11 and the rear arm 12 are moved closer to and away from each other only once, both end portions of the suture thread 22 respectively pass through the pair of edges Sa, Sb, and further, the both ends of the suture thread 22 can be located on the same side with respect to the gastric wall.

Since the number of processes in the suturing operation can be reduced by using the suturing apparatus 10, the suturing operation can be quickly performed.

The suturing apparatus 10 may also be provided with the above connection mechanism 40. That is, the front arm 11 and the rear arm 12 may be provided with the front connection member 41 and the rear connection member 42, respectively. In this case, the front connection member 41 and the rear connection member 42 are formed in the following manner. When the front connection member 41 is engaged with the rear connection member 42, central axes of the needle-like members 14 of the pair of branch portions 12s, 12s become coaxial with the central axes of the pair of housing spaces 16, 16 provided on the pair of branch portions 11s, 11s. This allows the pair of needle-like members 14, 14 to be certainly inserted into the pair of housing spaces 16, 16 and to be engaged with the pair of engagement members 21, 21.

A plurality of needle-like members 14 may be provided on each branch portion 12s at the rear arm 12 of the suturing apparatus 10. Further, housing space 16 of the same number as the needle-like members 14 provided on each branch portion 12s may be provided on each branch portion 11s at the front arm 11. In this case, when the front arm 11 and the rear arm 12 are moved closer to and away from each other only once, a plurality of the suture threads 22 can be inserted through the pair of edges Sa, Sb. The number of processes in the suturing operation can therefore be reduced, thereby further reducing a suturing time (Engagement Member 21)

The pair of engagement members 21, 21 of the suturing instrument 20 is simply required to have a structure in which, as described above, the pair of engagement members 21, 21 allows the arrowhead-like portion 14a of the needle-like member 14 to be inserted through the through hole 21h, whereas the engagement member 21 does not come out of the needle-like member 14 when the whole arrowhead-like portion 14a is inserted through the through hole 21h.

For example, the following structure can be employed for the engagement member 21.

Figure 10:
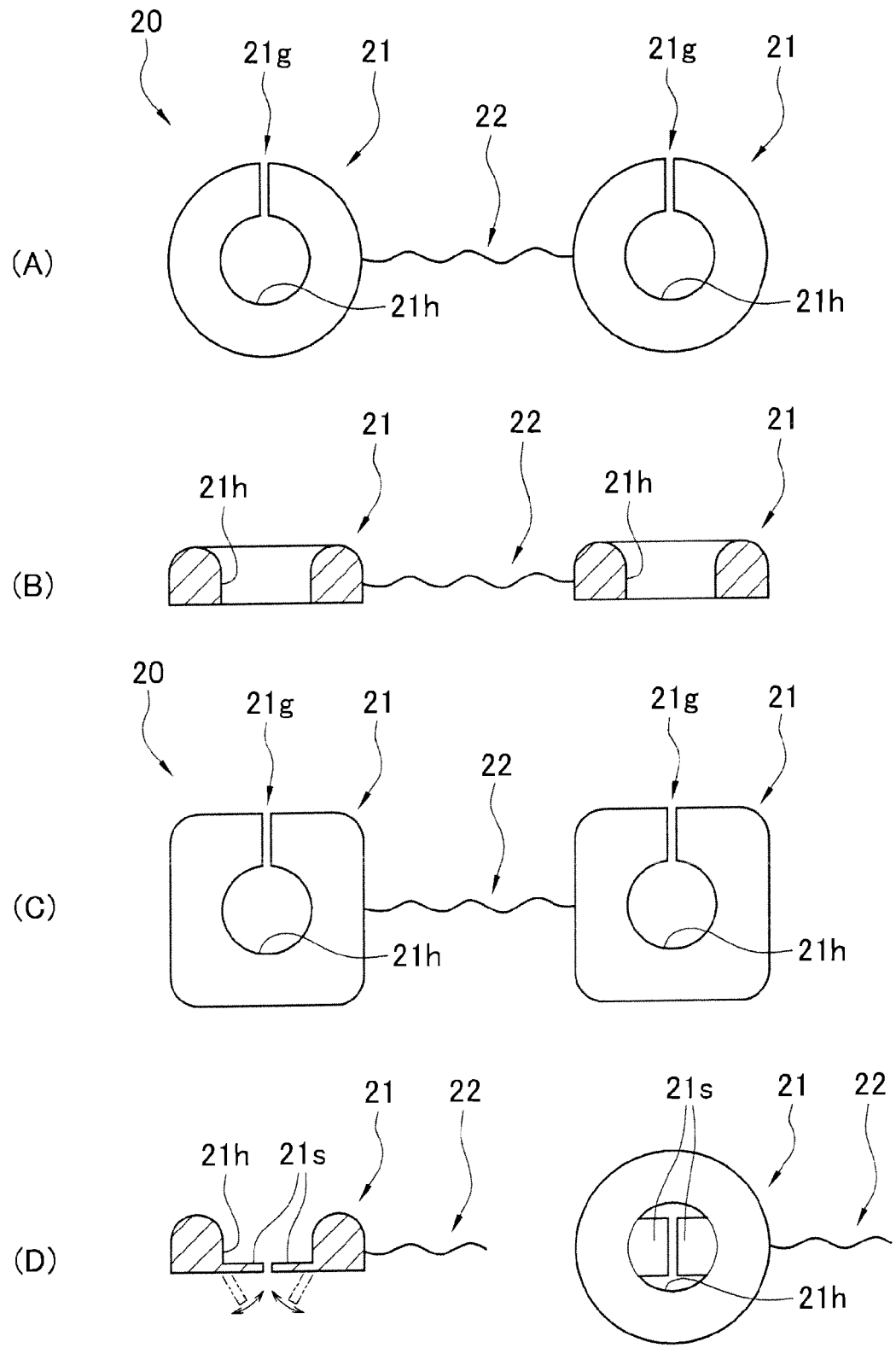
FIG. 10 shows schematic views of a suturing instrument 20 alone.

As shown in FIGS. 10 (a) and (b), an annular member having a partially-cut part 21g can be employed as the engagement member 21. The annular member is made of an elastic material (such as spring steel) having high hardness to some extent and an elastic force. As for such a member, an inside diameter of the through hole 21h of the engagement member 21 becomes shorter from a side from which the needle-like member 14 is inserted (top side in FIG. 10, hereinafter referred to as an insertion side) toward a side from which the needle-like member 14 protrudes (bottom side in FIG. 10, hereinafter referred to as a protrusion side). Further, in the engagement member 21, the inside diameter on the protrusion side in the through hole 21h is shorter than the outside diameter of the arrowhead-like portion 14a of the needle-like member 14, however, is longer than the outside diameter of the end of the shaft portion 14b. When the needle-like member 14 is inserted into the through hole 21h of the engagement member 21, the partially-cut part 21g of the engagement member 21 is widened allowing the arrowhead-like portion 14a of the needle-like member 14 to be inserted therethrough. Then, when the arrowhead-like portion 14a of the needle-like member 14 is completely inserted through the through hole 21h of the engagement member 21, the engagement member 21 is restored to the original state by the elastic force (that is, the partially-cut part 21g of the engagement member 21 returns to be closed). On the other hand, if the needle-like member 14 is intended to be pulled out from the engagement member 21, the needle-like member 14 is not pulled out from the engagement member 21. This is because the inside diameter of the through hole 21h on the protrusion side is shorter than a diameter of a base end of the arrowhead-like portion 14a of the needle-like member 14, and thereby the base end of the arrowhead-like portion 14a of the needle-like member 14 is caught on a surface on the protrusion side of the engagement member 21.

Alternatively, in the engagement member 21 with the inside diameter of the through hole 21h of the engagement member 21 larger than the arrowhead-like portion 14a of the needle-like member 14, a holding portion 21f nipping and holding the needle-like member 14 may be provided on an inner face of the through hole 21h in case the needle-like member 14 comes out of the through hole 21h of the engagement member 21. As shown in FIG. 10 (d), for example, a pair of gripper pieces 21s, 21s is provided on the inner face on the protrusion side in the through hole 21h. The pair of gripper pieces 21s, 21s is made of an elastic material that is hard to bend toward the insertion side but easy to bend toward the opposite side. A distance between tips of the pair of gripper pieces 21s, 21s is shorter than the outside diameter of the arrowhead-like portion 14a of the needle-like member 14 but is longer than the outside diameter of the end of the shaft portion 14b. With such a structure, the pair of gripper pieces 21s, 21s is restored to the original state by the elastic force when the arrowhead-like portion 14a of the needle-like member 14 is completely inserted (that is, the shaft portion 14b is sandwiched by the tips of the pair of gripper pieces 21s, 21s). Since the pair of gripper pieces 21s, 21s becomes resistant to the movement, the needle-like member 14 is not pulled out from the engagement member 21 even if the needle-like member 14 is intended to be pulled out from the engagement member 21.

Figure 11:
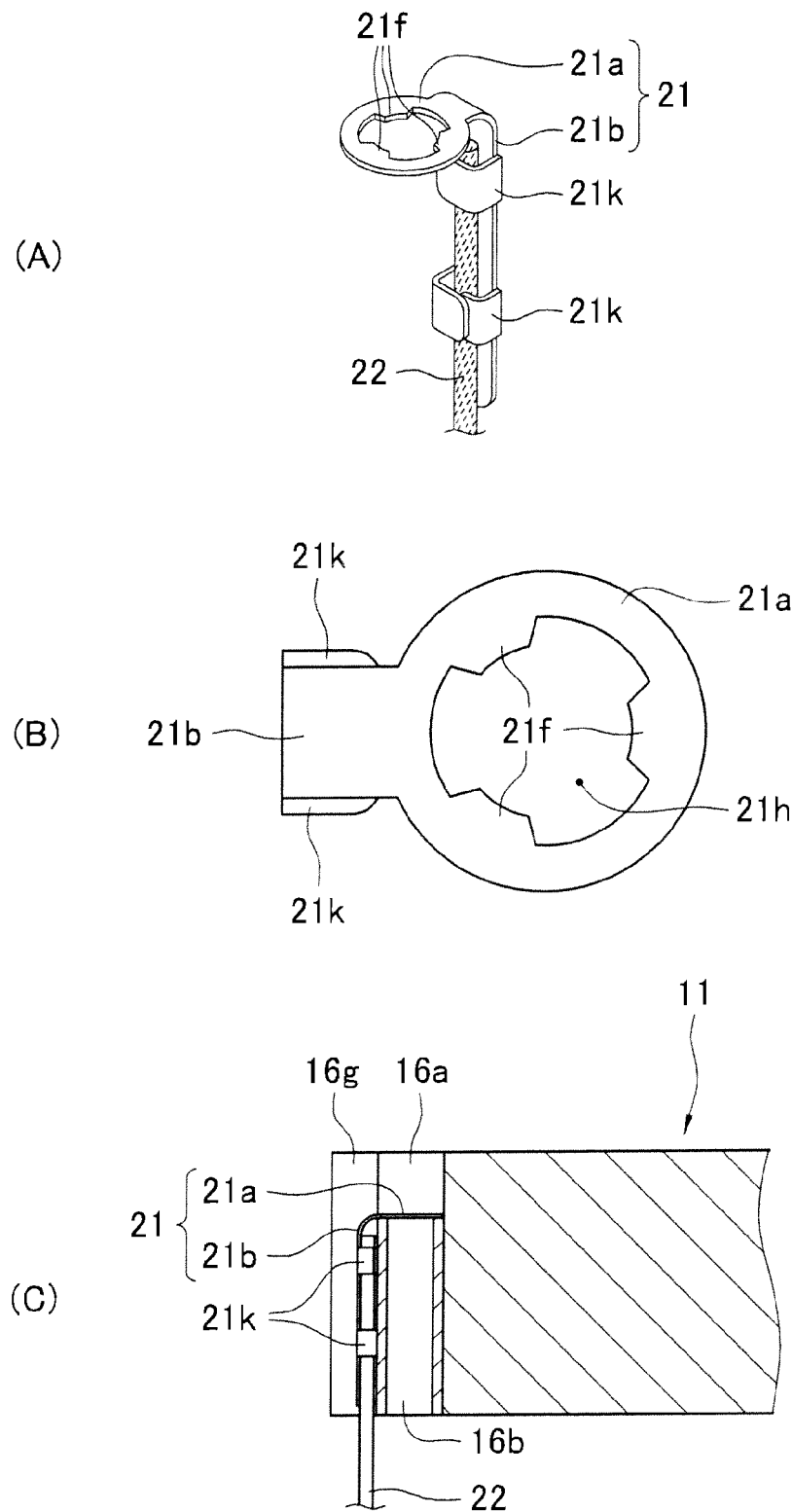
FIG. 11 shows schematic views of an engagement member 21 having a connection piece 21b; and (A): a schematic perspective view, (B): a schematic plan view, and (C): a schematic view illustrating a state where the front arm 11 having a connection-piece housing groove 16g is provided in a housing space 16.

Further, a shape shown in FIG. 11 may be employed for the engagement member 21.

As shown in FIG. 11, the engagement member 21 is a plate-like member formed into an annular shape and has three engagement pieces 21f on an inner end thereof. As for this engagement member 21, an inside diameter thereof is larger than the arrowhead-like portion 14a of the needle-like member 14, however, a diameter of a circle formed with inner ends of the three engagement pieces 21f is smaller than the arrowhead-like portion 14a. With such a shape, the three engagement pieces 21f are caught on the step between the arrowhead-like portion 14a and the shaft portion 14b when the arrowhead-like portion 14a is inserted through the through hole 21h, thereby making it difficult to pull out the needle-like member 14 from the engagement member 21. Moreover, since a resistance at the time of inserting the needle-like member 14 through the through hole 21h of the engagement member 21 can be reduced, the needle-like member 14 can be more certainly engaged with the engagement member 21 at the time of moving the rear arm 12 and the front arm 11 closer to each other.

A method for fixing the suture thread 22 to the engagement member 21 is not particularly limited. As shown in FIG. 10, for example, the engagement member 21 may be tied with the suture thread 22 for fixing. As shown in FIG. 11, the engagement member 21 may be provided with a connection piece 21b that is connected to the suture thread 22.

As shown in FIG. 11, the engagement member 21 with the connection piece 21b includes an engagement portion 21a provided with the through hole 21h and the connection piece 21b integrally formed with the engagement portion 21a. This connection piece 21b is bent at a connection part with the engagement portion 21a and an axial direction of the connection piece 21b is in parallel with the central axis of the through hole 21h. The connection piece 21b is provided with a plurality of gripper pieces 21k along the axial direction.

Accordingly, the suture thread 22 is provided along the axial direction of the connection piece 21b to sandwich the suture thread 22 between the connection piece 21b and the plurality of gripper pieces 21k, thereby allowing the suture thread 22 to be fixed to the engagement member 21.

The axial direction of the connection piece 21b is in parallel with the central axis of the through hole 21h. Therefore, when the arrowhead-like portion 14a of the needle-like member 14 is inserted through the through hole 21h of the engagement member 21, the connection piece 21b can be along a side face of the arrowhead-like portion 14a or the central axis of the needle-like member 14 can become parallel with the axial direction of the connection piece 21b. Then, even if the connection piece 21b is provided, a resistance due to the connection piece 21b can be reduced at the time of the needle-like member 14 passing through a gastric wall or the like. In particular, in the case of integrally forming the connection piece 21b and the engagement portion 21a, the resistance at the time of passing through the gastric wall or the like can be further reduced if a connection part of the two is bent so as to be a curved surface.

A method for fixing the suture thread 22 to the connection piece 21b is not limited to the above method. For example, the connection piece 21b may be a plate-like or rod-like member not having the gripper pieces 21k. Then, the suture thread 22 may be fixed to the connection piece 21b by untwisting the end of the suture thread 22 and wrapping the untwisted thread around the connection piece 21b, followed by gluing them together using an adhesive or the like.

In the case of using one having the above connection piece 21b as the engagement member 21, it is preferred that, when the engagement member 21 is held in the housing space 16 of the front arm 11, a mechanism capable of holding the connection piece 21b is provided on the front arm 11.

For example, a connection-piece housing groove 16g is provided on a side face of the front arm 11 along the axial direction of the housing space 16. The back face 11b of the front arm 11 is provided with a communicating groove 16m for communication between the connection-piece housing groove 16g and the housing space 16. More specifically, the communicating groove 16m is provided so that the major diameter portion 16a of the housing space 16 communicates with the connection-piece housing groove 16g. A width of the communicating groove 16m is slightly wider than that of the connection piece 21b with the suture thread 22 attached thereto.

When the engagement member 21 is provided in the housing space 16, the engagement portion 21a is provided on the major diameter portion 16a of the housing space 16 and the connection piece 21b is provided in the communicating groove 16m. Then, the connection piece 21b is held with the axial direction thereof in parallel with an axial direction of the connection-piece housing groove 16g. Therefore, the engagement member 21 can be certainly held with the central axis of the through hole 21h of the engagement portion 21a corresponding to the central axis of the housing space 16. Moreover, an inclination of the engagement portion 21a in the housing space 16 can be prevented because the connection piece 21b is housed in the connection-piece housing groove 16g. Therefore, the engagement member 21 can be stably held in the housing space 16.

Although the description has been made on the case where the engagement member 21 (engagement portion 21a in the case of providing the connection piece 21b) and the through hole 21h have the annular shape in the above example, the shapes of the engagement member 21 and the through hole 21h are not limited to such a shape. As shown in FIG. 10 (c), for example, the shape of the engagement member 21 may be a quadrilateral, triangle, pentagon or the like, not particularly limited. The shape of the through hole 21h may also be a quadrilateral, triangle, pentagon or the like, not particularly limited. In the case where an external shape of the engagement member 21 is quadrilateral or the like, it is preferred that corners of the engagement member 21 are rounded off or the like in order not to injure a gastric wall or the like.

As the engagement member 21, one obtained by spirally winding a linear member like a coil spring may also be used. Also in this case, the outside diameter of the engagement member 21 is larger than the minor diameter portion 16b of the housing space 16, and the inside diameter of the engagement member 21 is larger than the outside diameter of the end of the shaft portion 14b but is smaller than the arrowhead-like portion 14a. In particular, if the inside diameter becomes smaller from one end of the engagement member 21 toward the other end, the arrowhead-like portion 14a can be easy to inserted through the engagement member 21 but hard to be pulled out from the engagement member 21. As a method for making the inside diameter smaller from the one end of the engagement member 21 toward the other end, a method for forming the engagement member 21 into an almost cone may be employed.

(Description of Suturing Apparatus in Another Embodiment)

The suturing apparatus 10 in another embodiment will be described now.

The suturing apparatus 10 in another embodiment has the substantially same structure as the above suturing apparatus 10 except for the structure of the front-rear pair of arms 11, 12. Therefore, description concerning the arm moving means 13 or the suturing instrument 20 having the substantially same structure is properly omitted.

(Description of Front-Rear Pair of Arms 11, 12)

The front-rear pair of arms 11, 12 of the suturing apparatus 10 in another embodiment will be described now.

A common shape or the like of the front-rear pair of arms 11, 12 is first described.

Figure 12:
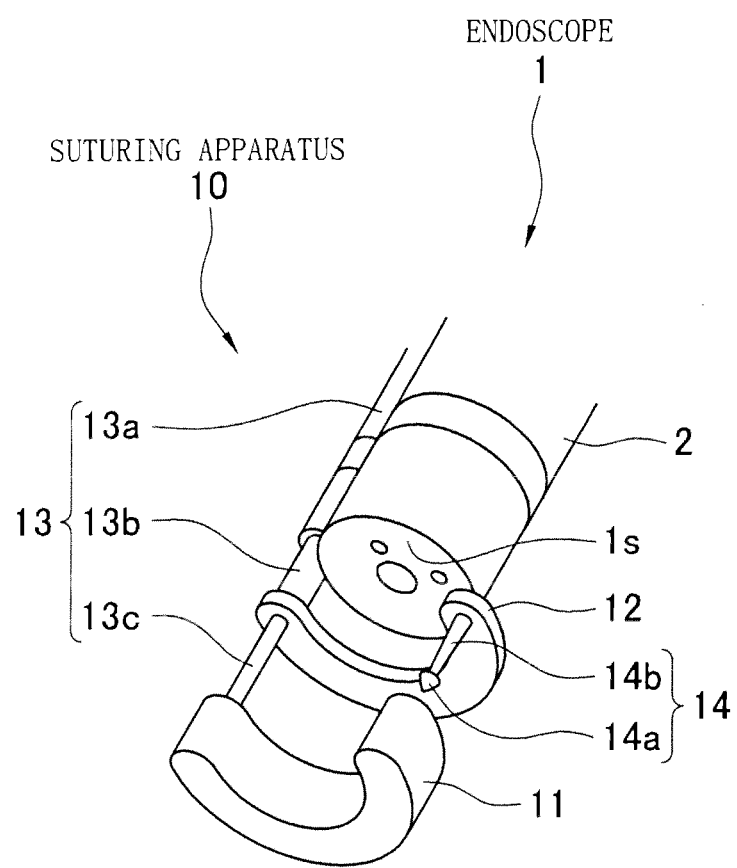
FIG. 12 is a schematic view of the endoscope 1 having the suturing apparatus 10 in another embodiment.
Figure 13:
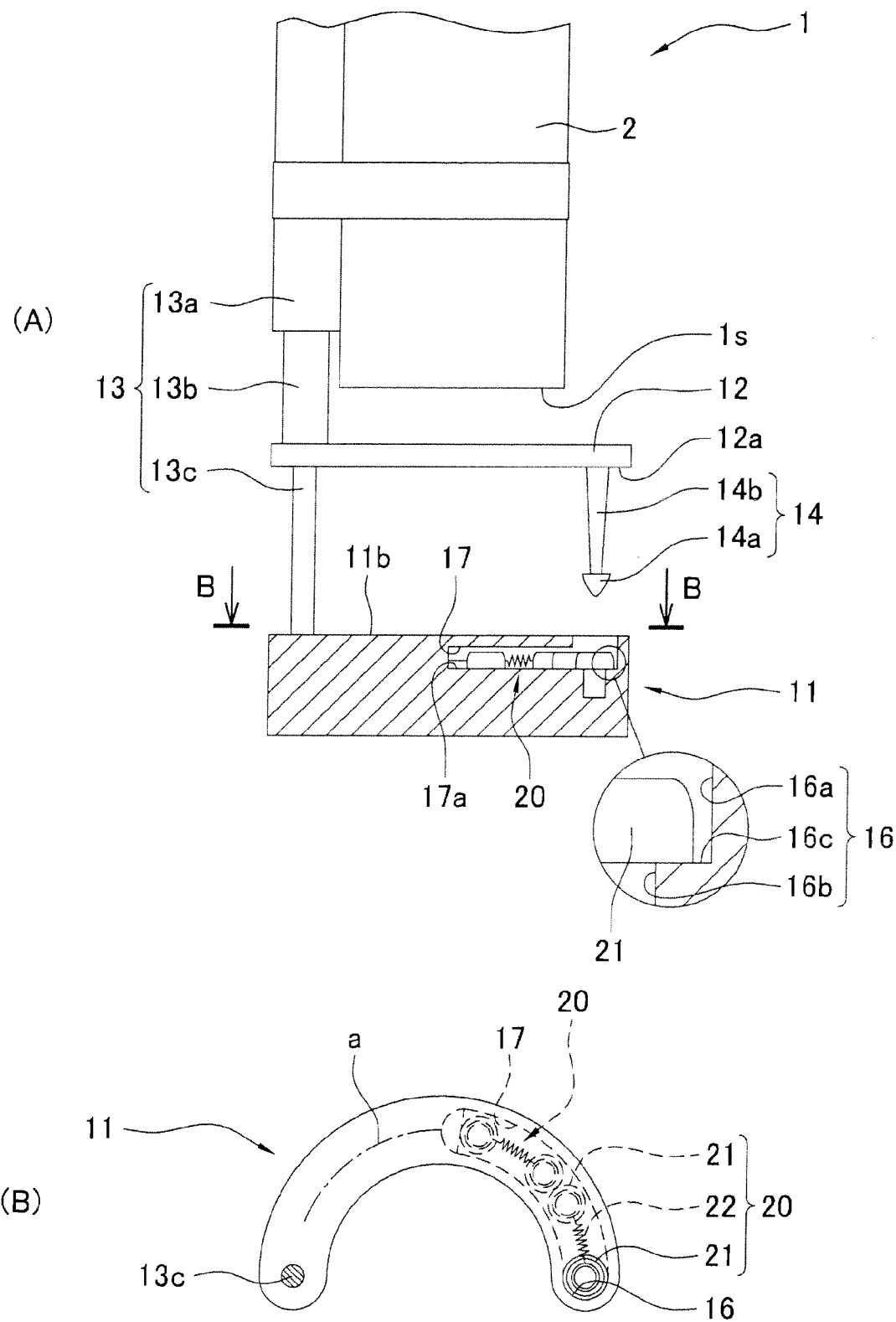
FIG. 13 shows (A): a schematic side view of the suturing apparatus 10 and (B): a fragmentary view taken in the direction of arrows B-B in (A).

As shown in FIGS. 12 and 13, base ends of the front-rear pair of arms 11, 12 are attached to the front-arm moving tube 13c and the rear-arm moving tube 13b of the arm moving means 13, respectively.

The arms 11, 12 are plate-like members formed into an almost arc, when viewed (see FIG. 13 (B), hereinafter referred to as a planar view) from axial directions of the moving tubes 13c, 13b at connection parts with the arms 11, 12 (hereinafter, simply referred to as an axial direction of a tip of each of the moving tubes 13c, 13b). Both of the arms 11, 12 are formed into substantially similar figures in shapes from the planar view. Although sizes of the arms 11, 12 are not particularly limited, such size is preferred that the arms 11, 12 do not interrupt illumination and a visual field of a CCD camera provided on a front face of a tip of the endoscope 1. For example, it is preferred that a radius of curvature of a central axis a in the rear arm 12 has a length to the same extent of a diameter of the shaft 2 in the endoscope.

The shape of the arms 11, 12 is not necessarily an arc and may have a rod-like shape or a rectangular shape from the planer view. In the case of the arms 11, 12 in the rod-like shape or the rectangular shape, it is preferred that each of the arms 11, 12 has a length in the axial direction to the same extent of an outside diameter of the shaft 2 of the endoscope 1.

Although a material of the arms 11, 12 is not particularly limited, the material preferably has strength not to be deformed at the time of suturing. For example, metal, reinforced plastic or the like is preferable.

Each of the front-rear pair of arms 11, 12 will now be described in detail.

The rear arm 12 is first described.

As shown in FIGS. 12 and 13, the rear arm 12 is formed into the above shape and the base end is attached to the tip of the rear-arm moving tube 13b. In the rear arm 12, a surface on a side of the front arm 11 (hereinafter, referred to as a front face 12a) is formed into a flat surface perpendicular to the axial direction of the tip of the rear-arm moving tube 13b.

As shown in FIG. 13, the above needle-like member 14 is provided at a tip of the front face 12a of the rear arm 12. A base end of the needle-like member 14 is fixed to the front face 12a so that an axial direction of the needle-like member 14 is perpendicular to the front face 12a (in other words, the axial direction becomes parallel with the axial direction of the tip of the rear-arm moving tube 13b).

The rear arm 12 may not have a plate-like shape and a surface thereof (front face 12a or a back face) may not be perpendicular to the axial direction of the tip of the rear-arm moving tube 13b. The surface of the rear arm 12 is not necessarily flat.

Further, a position of the rear arm 12 on which the needle-like member 14 is provided is not particularly limited and is not necessarily the tip of the rear arm 12.

The front arm 11 will be described now.

As shown in FIG. 13, the base end of the front arm 11 is attached to the tip of the front-arm moving tube 13c. The front arm 11 is formed with a plate-like member having a thickness to some extent. More specifically, the front arm 11 has such a size as to form space capable of housing the suturing instrument 20 described later thereinside, namely, a thickness and a width as to form space capable of housing the suturing instrument 20.

In the front arm 11, a surface on a side of the rear arm 12 (top face in FIG. 13 (A), hereinafter referred to as a back face 11b) is formed into a flat surface perpendicular to the axial direction of the tip of the front-arm moving tube 13c. That is, the back face 11b of the front arm 11 becomes parallel with the front face 12a of the rear arm 12.

The back face 11b of the front arm 11 is not necessarily flat, similarly to the front face 12a of the rear arm 12. Further, the back face 11b of the front arm 11 is not necessarily parallel with the front face 12a of the rear arm 12. However, if the back face 11b of the front arm 11 and the front face 12a of the rear arm 12 are both flat and in parallel with each other, it is preferable in that the suturing can be safely and certainly performed.

(Description of Housing Space 16)

Figure 14:
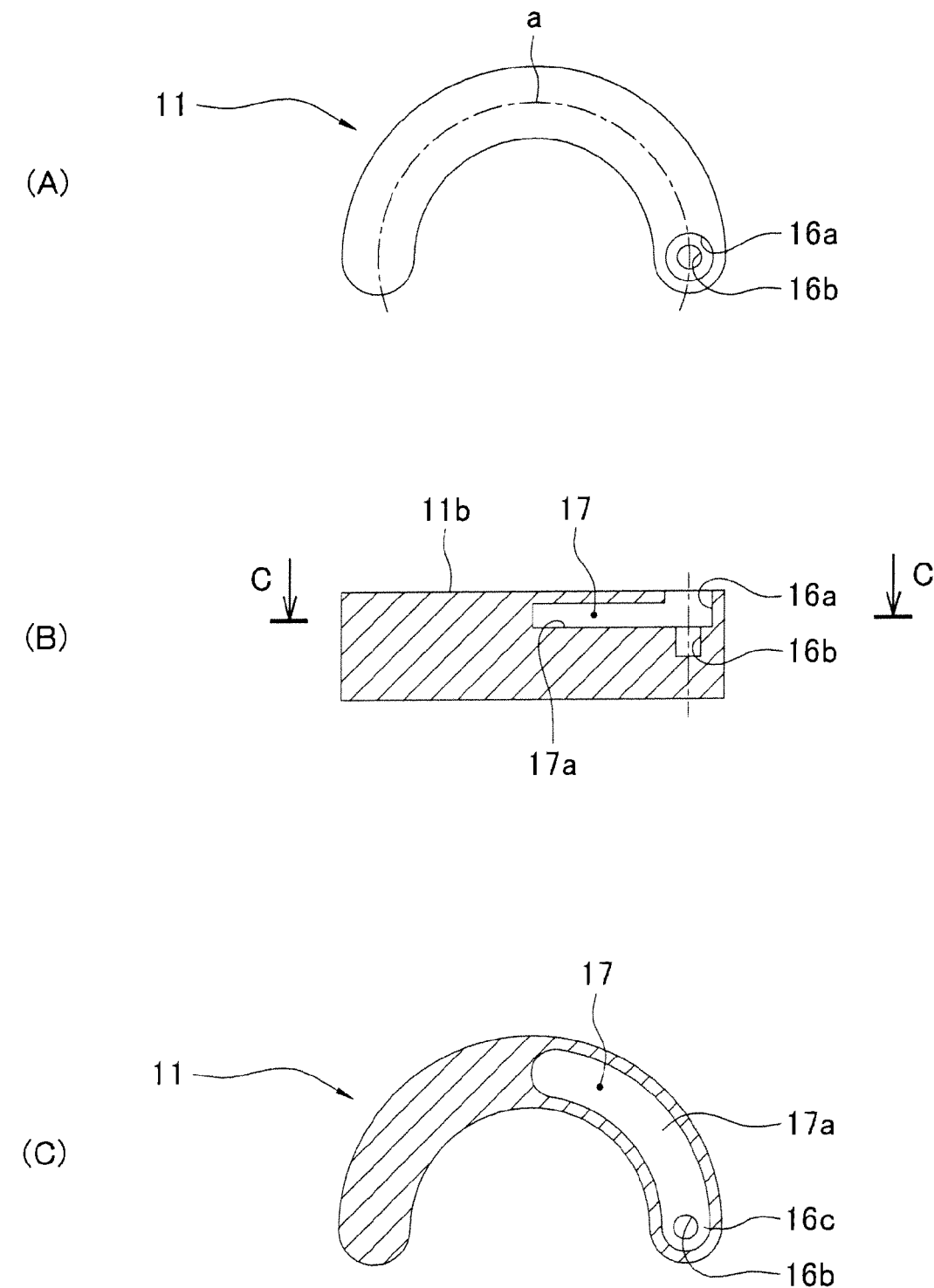
FIG. 14 shows explanatory diagrams of the front arm 11 alone; and (A): a plan view, (B): a sectional view taken along the a-line in (A), and (C): a fragmentary view taken in the direction of arrows C-C in (B).

As shown in FIGS. 13 and 14, the front arm 11 is provided with a housing space 16. The housing space 16 is a hole obtained by denting the back face 11b and does not extend through the front arm 11. In the housing space 16, a central axis thereof is in parallel with the axial direction of the tip of the rear-arm moving tube 13b.

The housing space 16 is formed at a position corresponding to the needle-like member 14 of the rear arm 12. More specifically, in the housing space 16, a distance from the central axis thereof to the central axis of the tip of the front-arm moving tube 13c is equal to a distance from the central axis of the tip of the rear-arm moving tube 13b to the central axis of the needle-like member 14. That is, in the housing space 16, when the front arm 11 and the rear arm 12 are rocked with their base ends as a pivot, a position where the central axis of the needle-like member 14 becomes coaxial with the central axis of the housing space 16 exists.

In the case where a relative rotation of the front-arm moving tube 13c and the rear-arm moving tube 13b around the axis is fixed, the central axis of the housing space 16 preferably becomes coaxial with the central axis of the needle-like member 14.

An inside diameter of the housing space 16 is longer than the outside diameter of the needle-like member 14. Moreover, the housing space 16 is a stepped hole, and has a part with a major inside diameter (an engagement-member housing portion 16a) on an upper side and a part with a minor inside diameter (a needle-like member tip housing portion 16b) on a lower side.

A connection surface 16c between the engagement-member housing portion 16a and the needle-like member tip housing portion 16b is perpendicular to the central axis of the housing space 16. The reason will be described later.

The front arm 11 is provided with a suturing-instrument holding space 17 communicating with the housing space 16. A bottom face 17a of the suturing-instrument holding space 17 is the same plane as the connection surface 16c of the housing space 16. The reason will be described later.

(Suturing Instrument 20)

As shown in FIG. 13, the suturing instrument 20 is housed in the suturing-instrument holding space 17. The suturing instrument 20 includes the pair of engagement members 21, 21 formed into an annular shape and the suture thread 22 connecting the pair of engagement members 21, 21.

The engagement member 21 is formed in a size to the extent that the engagement member 21 does not fall into the needle-like member tip housing portion 16b when being housed in the housing space 16. More specifically, an outside diameter of the engagement member 21 is shorter than an inside diameter of the engagement-member housing portion 16a and is longer than an inside diameter of the needle-like member tip housing portion 16b of the housing space 16.

(Brief Description of Operation of Suturing Apparatus 10 in the Embodiment)

According to the above configuration, in the suturing apparatus 10 in the embodiment, the arrowhead-like portion 14a of the needle-like member 14 can be inserted into the housing space 16 by operating the arm moving means 13, providing the front arm 11 and the rear arm 12 so that the needle-like member 14 faces to the housing space 16 (providing so that the needle-like member 14 becomes coaxial with the housing space 16), and by the arm moving means 13 causing the front arm 11 and the rear arm 12 to be moved closer to each other.

When one engagement member 21 of the suturing instrument 20 is provided in the housing space 16, the one engagement member 21 is provided on the connection surface 16c and the through hole 21h of the engagement member 21 is provided above the needle-like member tip housing portion 16b.

The arrowhead-like portion 14a of the needle-like member 14 is then inserted into the housing space 16 with the one engagement member 21 of the suturing instrument 20 provided in the housing space 16. Consequently, the arrowhead-like portion 14a of the needle-like member 14 can be inserted into the through hole 21h of the engagement member 21. The front arm 11 and the rear arm 12 are then moved closer to each other until the whole arrowhead-like portion 14a of the needle-like member 14 is inserted into the needle-like member tip housing portion 16b. Consequently, the needle-like member 14 can be inserted through the through hole 21h of the engagement member 21 up to the shaft portion 14b.

When the front arm 11 and the rear arm 12 are moved away from each other by operating the arm moving means 13 in such a state, the engagement member 21 can be removed from the housing space 16 together with the needle-like member 14.

When the one engagement member 21 is removed from the housing space 16, the other engagement member 21 connected to the one engagement member 21 via the suture thread 22 is pulled by the suture thread 22 to move from the suturing-instrument holding space 17 into the housing space 16.

When the other engagement member 21 moves into the housing space 16, the other engagement member 21 is provided on the connection surface 16c and the through hole 21h of the engagement member 21 is provided above the needle-like member tip housing portion 16b.

When the front arm 11 and the rear arm 12 are moved closer to each other by operating the arm moving means 13 in such a state, the arrowhead-like portion 14a of the needle-like member 14 can be inserted into the through hole 21h of the other engagement member 21.

Figure 15:
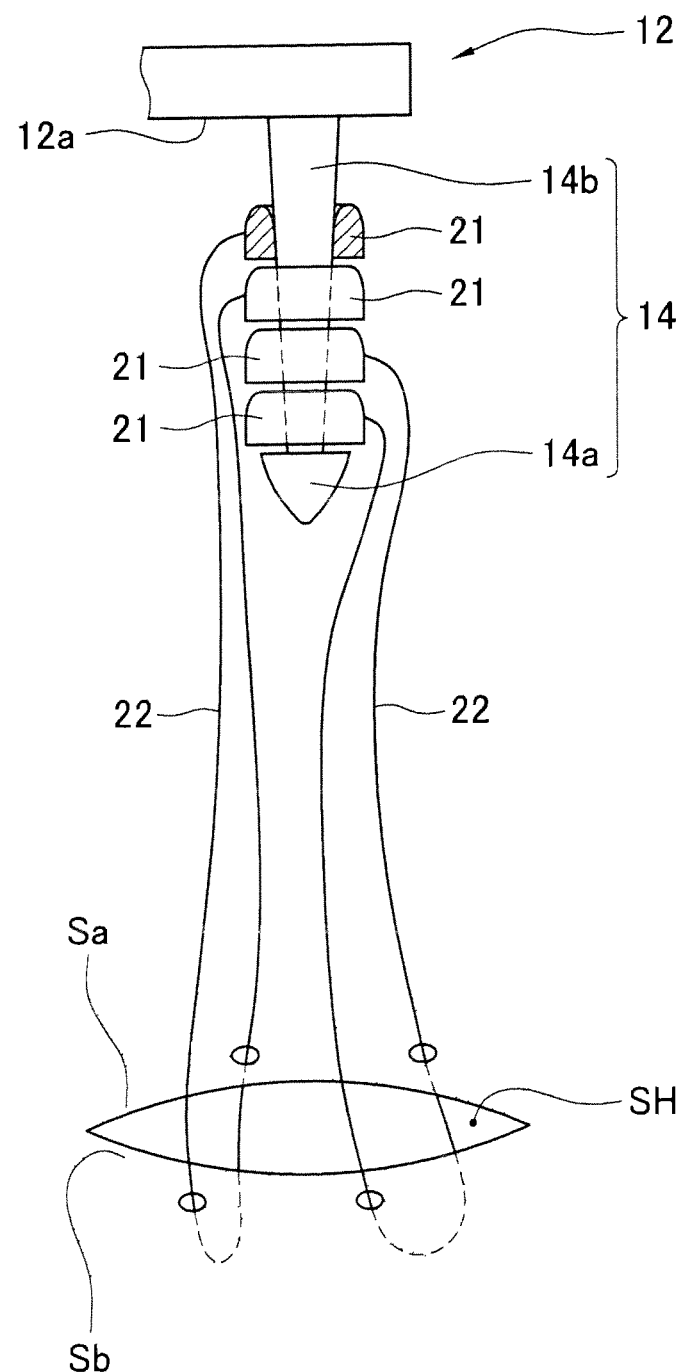
FIG. 15 is a schematic view illustrating an incised part SH sutured by the suturing apparatus 10 in the embodiment.

Then, the pair of engagement members 21, 21 is engaged with the needle-like member 14, and thereby the suture thread 22 connecting the pair of engagement members 21, 21 can be formed into a loop (see FIG. 15).

Accordingly, in the suturing apparatus 10 in the embodiment, the front arm 11 and the rear arm 12 are moved closer to and away from each other twice and a position of an object through which the needle-like member 14 is inserted for the first time is different from that of for the second time, while the object is provided between the front arm 11 and the rear arm 12. In that case, the suture thread 22 can pass through the object so that both ends of the suture thread 22 are located on the same side of the object. In other words, the suture thread 22 can pass through the object so that a part between the both ends of the suture thread 22 is caught in the object (see FIG. 15).

(Suturing Living Body with Suturing Apparatus 10 in the Embodiment)

According to the above configuration, when the suturing apparatus 10 in the embodiment is attached to the shaft 2 of the endoscope 1, an incised part in the gastric wall or the like can be sutured at the stomach.

Hereinafter, a suturing operation of an incised part with the suturing apparatus 10 in the embodiment will be described with reference to FIGS. 16 and 17.

Hereinafter, suturing of an incised part SH formed in the gastric wall will be described.

The shaft 2 of the endoscope 1 having the suturing apparatus 10 in the embodiment attached thereto is first inserted into a stomach to provide a tip face of the shaft 2 in the vicinity of the incised part SH to be sutured. In such a state, only the front arm 11 is inserted into the incised part SH by operating the front-arm moving tube 13c of the arm moving means 13.

Figure 16:
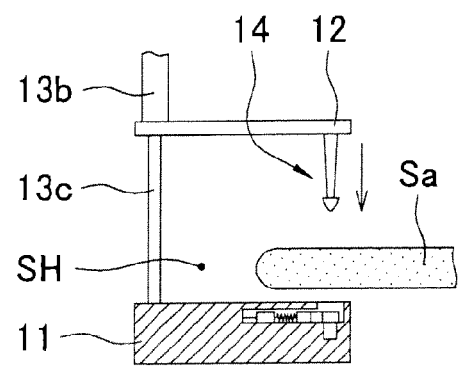
FIG. 16 shows schematic views illustrating a suturing operation with the suturing apparatus 10 in the embodiment.
Figure 16:
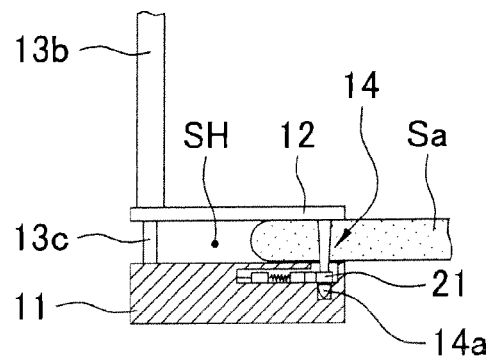
Figure 16:
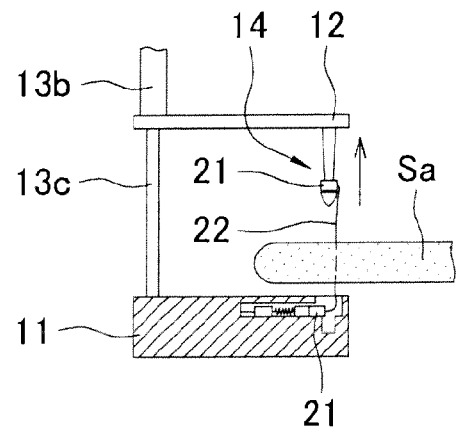
Figure 16:
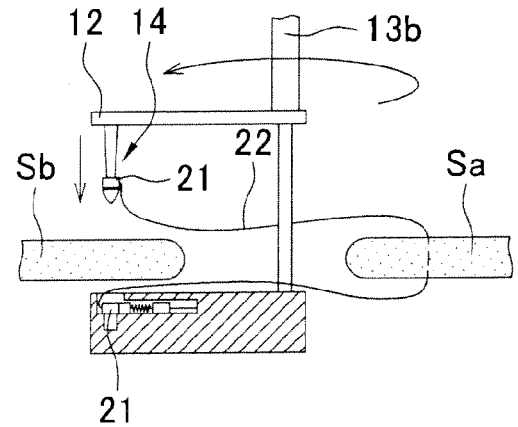
Figure 17:
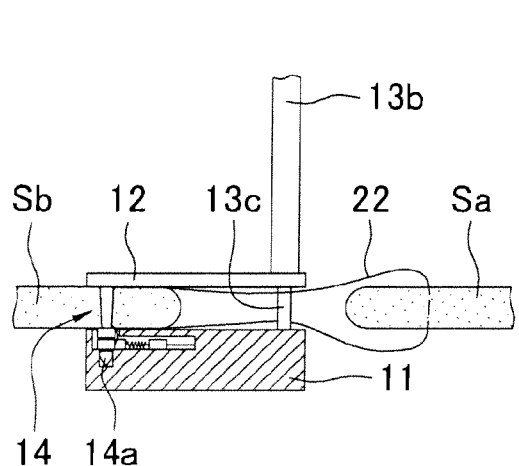
FIG. 17 shows schematic views illustrating the suturing operation with the suturing apparatus 10 in the embodiment.
Figure 17:
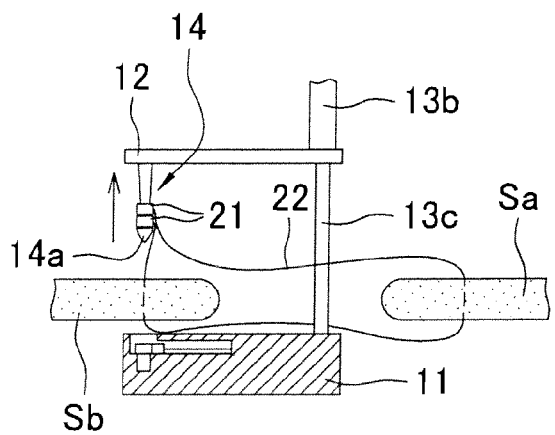
Figure 17:
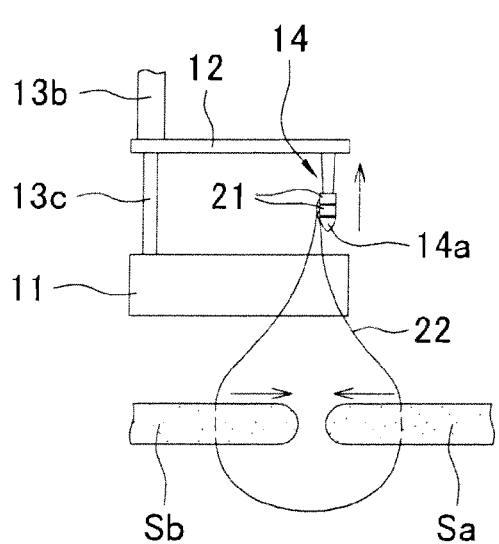
Figure 17:
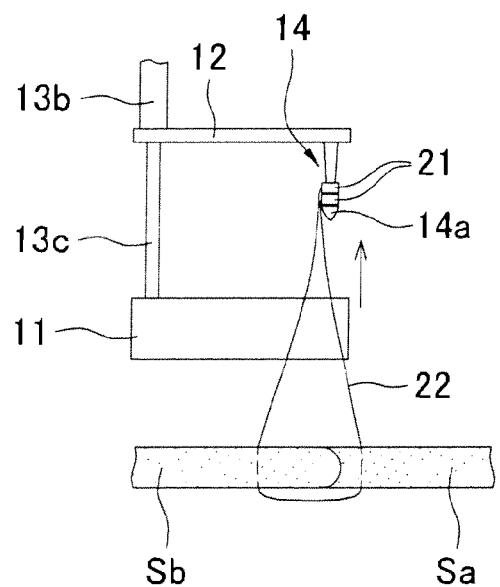

After that, the front arm 11 and the rear arm 12 are provided by operating the rear-arm moving tube 13b and the front-arm moving tube 13c of the arm moving means 13 so that one edge Sa of the incised part SH is sandwiched between the back face 11b of the front arm 11 and the front face 12a of the rear arm 12 (see FIG. 16 (1)).

Obviously, the front arm 11 and the rear arm 12 are provided so that the needle-like member 14 becomes coaxial with the housing space 16.

In the state of FIG. 16 (1), the rear arm 12 approaches the front arm 11 by operating the rear-arm moving tube 13b of the arm moving means 13. This allows the needle-like member 14 to be inserted through the one edge Sa, allowing the arrowhead-like portion 14a of the needle-like member 14 to pass through the through hole 21h of one engagement member 21 of the suturing instrument 20. The one engagement member 21 can therefore be engaged with the needle-like member 14 (FIG. 16 (2)).

The description has been made on the case where the rear arm 12 approaches the front arm 11 at the time of moving the rear arm 12 and the front arm 11 closer to each other in FIG. 16. However, the front arm 11 may approach the rear arm 12, or both of them are moved together to come closer to each other. This point is similar to the case where the rear arm 12 and the front arm 11 are moved away from each other in the following description. Accordingly, hereinafter, a description is made only on the case where the rear arm 12 is moved with respect to the front arm 11. The description is omitted on the other cases (the case where the front arm 11 is moved with respect to the rear arm 12, and the case where both of them are moved together).

When the one engagement member 21 is engaged with the needle-like member 14, the rear arm 12 is moved away from the front arm 11 by operating the rear-arm moving tube 13b of the arm moving means 13. At this time, the needle-like member 14 returns to an inside of stomach through a hole (hereinafter, referred to as a first perforated hole) formed at the time of inserting the needle-like member 14 through the one edge Sa. Then, the one engagement member 21 engaged with the needle-like member 14 also moves to the inside of stomach together with the needle-like member 14.

On the other hand, the other engagement member 21 of the suturing instrument 20 remains in the suturing-instrument holding space 17 of the front arm 11 even if the one engagement member 21 moves. The suture thread 22 connecting both of the engagement members 21 is therefore provided so as to pass through the first perforated hole. That is, one end of the suture thread 22 fixed to the one engagement member 21 is inside the stomach, whereas the other end of the suture thread 22 fixed to the other engagement member 21 is outside the stomach (FIG. 16 (3)).

In the state of FIG. 16 (3), the other edge Sb of the incised part SH is sandwiched between the back face 11b of the front arm 11 and the front face 12a of the rear arm 12 by changing directions and positions of the rear arm 12 and the front arm 11 (FIG. 16 (4)).

When the directions of the rear arm 12 and the front arm 11 are changed, the suture thread 22 is pulled to some extent, causing the other engagement member 21 to move from the suturing-instrument holding space 17 into the housing space 16. Since the bottom face 17a of the suturing-instrument holding space 17 is the same plane as the connection surface 16c of the housing space 16, as described above, the other engagement member 21 smoothly moves into the housing space 16. The engagement member 21 moved in the housing space 16 is then located at a position to be engaged with the needle-like member 14 (that is, a position where the arrowhead-like portion 14a of the needle-like member 14 can pass through the through hole 21h) when the rear arm 12 and the front arm 11 are moved closer to each other.

Obviously, the front arm 11 and the rear arm 12 are also provided so that the needle-like member 14 becomes coaxial with the housing space 16 in this case.

In the state of FIG. 16 (4), the rear arm 12 is moved closer to the front arm 11 by operating the rear-arm moving tube 13b of the arm moving means 13. This allows the needle-like member 14 to be inserted through the other edge Sb, thereby allowing the needle-like member 14 to be engaged with the other engagement member 21 (FIG. 17 (5)).

When the other engagement member 21 is engaged with the needle-like member 14, the rear arm 12 is moved away from the front arm 11 by operating the rear-arm moving tube 13b of the arm moving means 13. In that case, the needle-like member 14 returns to the inside of stomach through a hole (hereinafter, referred to as a second perforated hole)

formed at the time of inserting the needle-like member 14 through the other edge Sb. Then, the other engagement member 21 engaged with the needle-like member 14 also moves to the inside of stomach together with the needle-like member 14, thereby the suture thread 22 passing through the second perforated hole (FIG. 17 (6)).

Each of the pair of engagement members 21 having each end of the suture thread 22 fixed thereto is engaged with the one needle-like member 14. Therefore, the suture thread 22 is formed into a loop extending from needle-like member 14 (that is, the inside of stomach) to an outside of stomach through the first perforated hole and returning from the outside of stomach to the needle-like member 14 (that is, the inside of stomach) through the second perforated hole (see FIG. 17 (7) and FIG. 15).

When the above loop of the suture thread 22 is formed, the front arm 11 is first moved into the stomach through the incised part SH by operating the arm moving means 13. When the front arm 11 enters the stomach, the shaft 2 itself or the rear arm 12 is moved so that the needle-like member 14 is moved away from the incised part SH. Since the both ends of the suture thread 22 are moved away from the incised part SH, the pair of edges Sa, Sb of the incised part SH are moved so that a length of a part in the suture thread 22 becomes shorter. The part in the suture thread 22 is located between a part having passed through the first perforated hole and a part having passed through the second perforated hole. That is, the pair of edges Sa, Sb of the incised part SH are moved so that end faces thereof come close to each other. As a result, the incised part SH is sutured so that the end faces of the edges Sa, Sb come in contact with each other (FIG. 17 (8)).

When the end faces of the pair of edges Sa, Sb in the incised part SH come in contact with each other, the suture thread 22 is fastened in such a state. More specifically, in the suture thread 22, a part extending from the needle-like member 14 (that is, the one engagement member 21) to the first perforated hole and a part extending from the needle-like member 14 (that is, the other engagement member 21) to the second perforated hole are fastened together. A commercially available clip or the like can be used for the thread-fastening. For example, the clip or the like is supplied from a forceps port of the endoscope 1 to be attached to the suture thread 22, thereby enabling the thread-fastening.

Finally, when, in the suture thread 22, a part located on a side of the needle-like member 14 with respect to the fastened part is cut, the incised part SH can be fixed with the end faces of the pair of edges Sa, Sb in the incised part SH in contact with each other.

Figure 18:
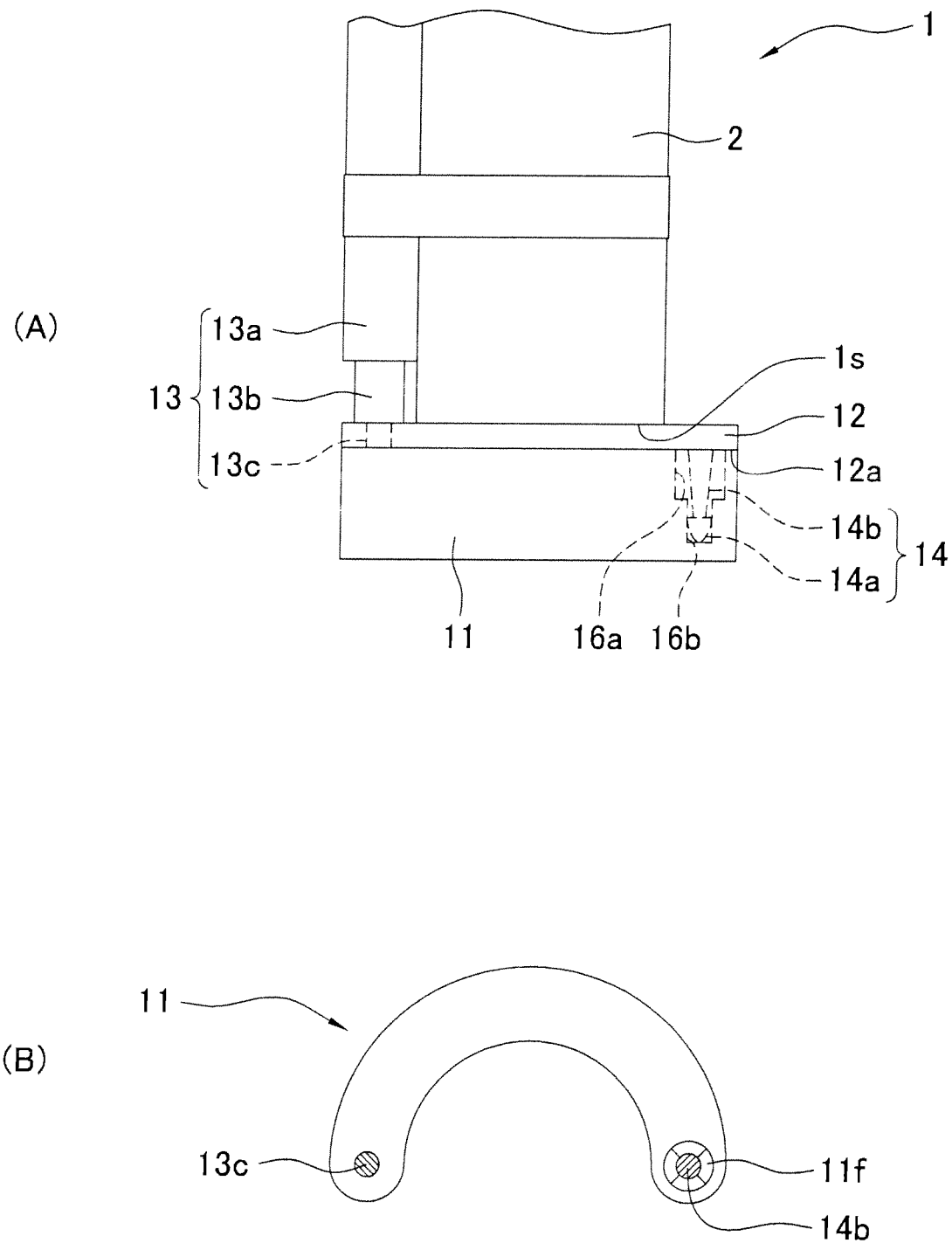
FIG. 18 shows schematic views when the front arm 11 and the rear arm 12 are moved closer to each other.

As shown in FIG. 18, when the shaft 2 having the suturing apparatus 10 in the embodiment attached thereto is inserted in the stomach, the needle-like member 14 is preferably inserted in the housing space 16 by moving the front arm 11 and the rear arm 12 closer to each other. Then, the shaft 2 with the suturing apparatus 10 can easily pass through an over tube or the like, and an injury of the stomach or the like due to the needle-like member 14 can be prevented.

In particular, a length of the needle-like member 14 and a depth of the housing space 16 are adjusted to the extent that the back face 11b of the front arm 11 can come in contact with the front face 12a of the rear arm 12. In that case, a resistance applied to the suturing apparatus 10 from the over tube or the like can be further reduced when the shaft 2 with the suturing apparatus 10 passes through the over tube or the like. Moreover, the resistance applied to the suturing apparatus 10 can be further reduced if the back face of the rear arm 12 approaches the tip face 1s of the shaft 2 so as to come in contact with each other.

A fin 11f may also be provided on an inner face of an opening of the housing space 16. The fin 11f includes a plurality of sheet-like members that cover a gap between an inner end of the opening and a circumference surface of the needle-like member 14 with the needle-like member 14 inserted in the housing space 16. Then, biological tissue or the like can be prevented from entering the housing space 16 from the gap between the inner end of the opening and the circumference surface of the needle-like member 14 until the suturing apparatus 10 is provided on a predetermined position.

(Structure of Front Arm 11)

In the above embodiment, the description has been made on the case where the other engagement member 21 of the suturing instrument 20 moves from the suturing-instrument holding space 17 into the housing space 16 according to the movement of the front-rear pair of arms 11, 12. That is, the description has been made on the case where the rear arm 12, the needle-like member 14 and the suturing-instrument holding space 17 of the front arm 11 correspond to a supply mechanism in Claims.

A mechanism may be provided in which the front arm 11 pushes the engagement member 21 from the suturing-instrument holding space 17 to the housing space 16.

For example, in the suturing-instrument holding space 17, provided are a moving member that moves along an axial direction of the suturing-instrument holding space 17, and a biasing member (such as a spring) that biases the moving member toward the housing space 16. With such a configuration, when one engagement member 21 is in the housing space 16, the one engagement member 21 becomes resistant causing the other engagement member 21 to be held in the suturing-instrument holding space 17. Then, when the one engagement member 21 is removed from the housing space 16 together with the needle-like member 14, the other engagement member 21 can move. The other engagement member 21 can therefore be moved into the housing space 16 by being pushed with the moving member.

Moreover, in the case of providing the above supply mechanism, the one engagement member 21 in the housing space 16 is held between the other engagement member 21 and the inner face of the housing space 16 by a biasing force of the biasing member. Therefore, the one engagement member 21 can be prevented from falling off from the housing space 16 at the time of inserting the endoscope 1 into the stomach or the like.

In the case of moving the other engagement member 21 into the housing space 16, the other engagement member 21 is held between the moving member and the inner face of the housing space 16 by the biasing force of the biasing member. Therefore, the other engagement member 21 can be prevented from falling off from the housing space 16 even if the direction of the front arm 11 is changed (see FIG. 16 (4)) or the other engagement member 21 is pulled by the suture thread 22.

In the case of providing the above supply mechanism, suturing can be continuously performed for a plurality of times if the suturing-instrument holding space 17 can house a plurality of suturing instruments 20. For example, two suturing instruments 20 enable thread-fastening at two parts at the same time after suturing the two parts (see FIG. 15). Time for the suturing operation can therefore be reduced.

(Fall-Preventing Film)

The opening of the housing space 16 may be provided with a film through which the tip of the needle-like member 14 or the like can pass, for example, a resin film. Then, the suturing instrument 20 can be prevented from falling off from the housing space 16 until the front arm 11 is located at the incised part SH to start the suturing. For example, the suturing instrument 20 can be prevented from falling even if the tip face 1s of the shaft 2 of the endoscope 1 is turned upward.

A material of the film on the opening of the housing space 16 is not particularly limited. With a resin film or the like, the tip of the needle-like member 14 can pass through the film simply by inserting the needle-like member 14 into the housing space 16. Then, suturing with the suturing instrument 20 can be performed without an operation such as removing the film before the suturing. If the film has strength to some extent, some area of the opening of the housing space 16 can be covered with the film having the through hole formed by the needle-like member 14 even after the tip of the needle-like member 14 passes therethrough. Then, the film with the through hole can function as a fall-preventing film that prevents the engagement member 21 of the suturing instrument 20 from falling off from the housing space 16.

(Liquid Discharge Port)

The housing space 16 is provided not to extend through the front arm 11 in the above example, while there is a possibility that liquid such as blood in the stomach remains in the housing space 16 in that case. A discharge port from which liquid or the like in the housing space 16 is discharged outside may therefore be provided.

Figure 19:
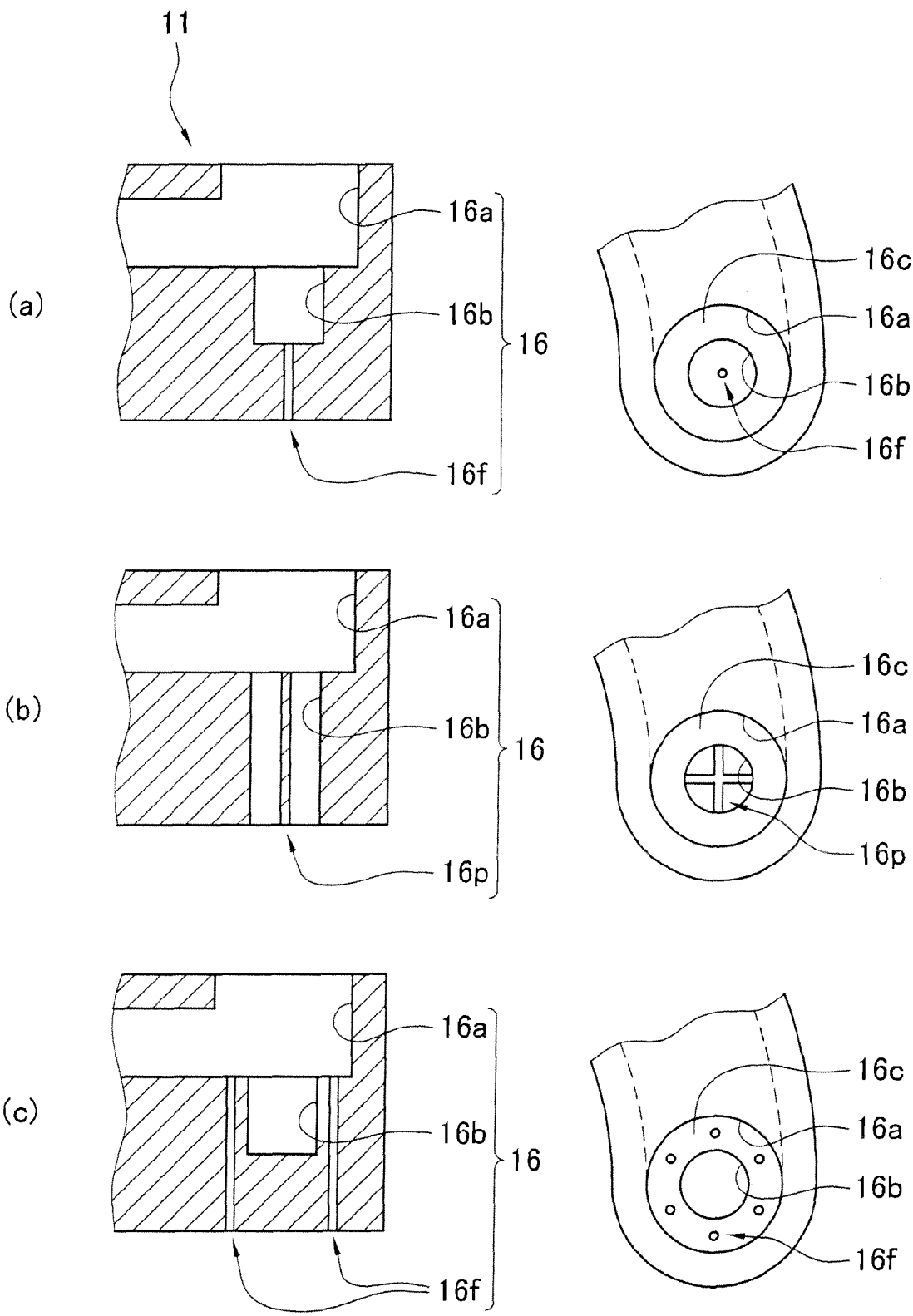
FIG. 19 shows schematic views of the front arm 11 provided with a liquid discharge port.

For example, as shown in FIG. 19 (a), a through hole 16f is provided between an inner bottom face of the needle-like member tip housing portion 16b of the housing space 16 and the front face of the front arm 11. The through hole 16f has a shorter diameter than does the needle-like member tip housing portion 16b. Then, the liquid in the housing space 16 can be discharged outside through the through hole 16f, while the tip of the needle-like member 14 is prevented from protruding from the front face of the front arm 11.

Moreover, the needle-like member tip housing portion 16b itself of the housing space 16 is formed into a through hole extending to the front face of the front arm 11. Then, a member preventing the tip of the needle-like member 14 from protruding from the front face of the front arm 11 may be provided in the needle-like member tip housing portion 16b. As shown in FIG. 19 (b), for example, if a grid-like plate 16p is provided in the needle-like member tip housing portion 16b, the liquid in the housing space 16 can be discharged outside while the tip of the needle-like member 14 is prevented from protruding from the front face of the front arm 11. A similar effect can be obtained if a net or the like is provided in the needle-like member tip housing portion 16b.

Further, as shown in FIG. 19 (c), the through hole 16f is provided between the connection surface 16c of the housing space 16 and the front face of the front arm 11. Although the liquid in the needle-like member tip housing portion 16b cannot be completely discharged outside in this case, some liquid can be discharged outside through the through hole 16f.

(Suturing Apparatus 10 in Another Embodiment)

As for the suturing apparatus 10 in the above embodiment, the description has been made on the case where the needle-like member 14 is exposed. A protector protecting the needle-like member 14 so as to surround the needle-like member 14 may be provided on the front arm 11. When the needle-like member 14 is stuck into an object such as a gastric wall, a force applied to the needle-like member 14 can be reduced, thereby suppressing damage of the needle-like member 14.

A suturing apparatus 10B provided with the protector has a substantially similar configuration to the suturing apparatus 10 in the above embodiment except for the configuration required due to providing the protector, and operates similarly to the suturing apparatus 10 at the time of suturing. Therefore, points only different from the suturing apparatus 10 in the above embodiment will be described as follows.

Figure 20:
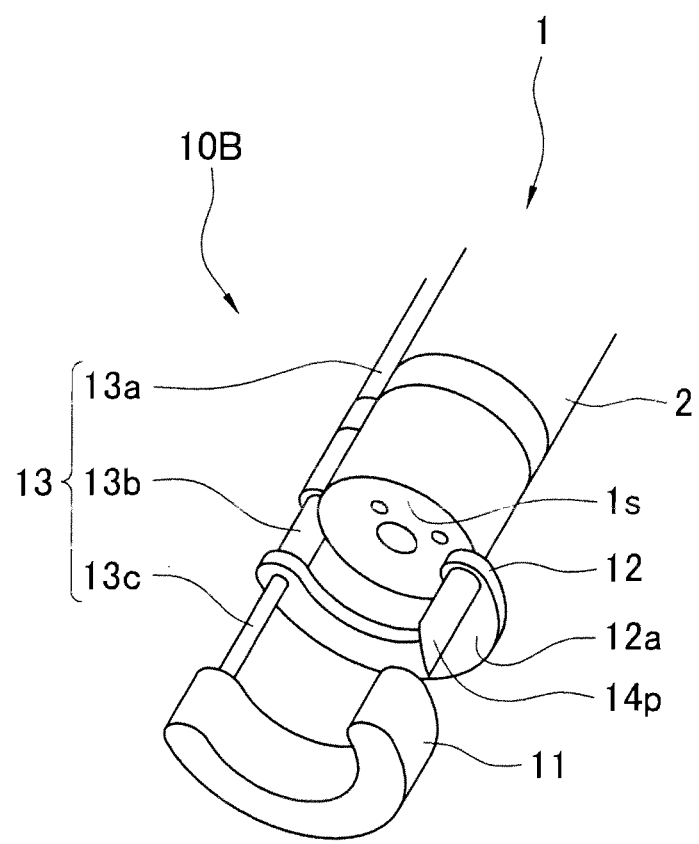
FIG. 20 is a schematic view of the endoscope 1 having a suturing apparatus 10B in another embodiment.
Figure 21:
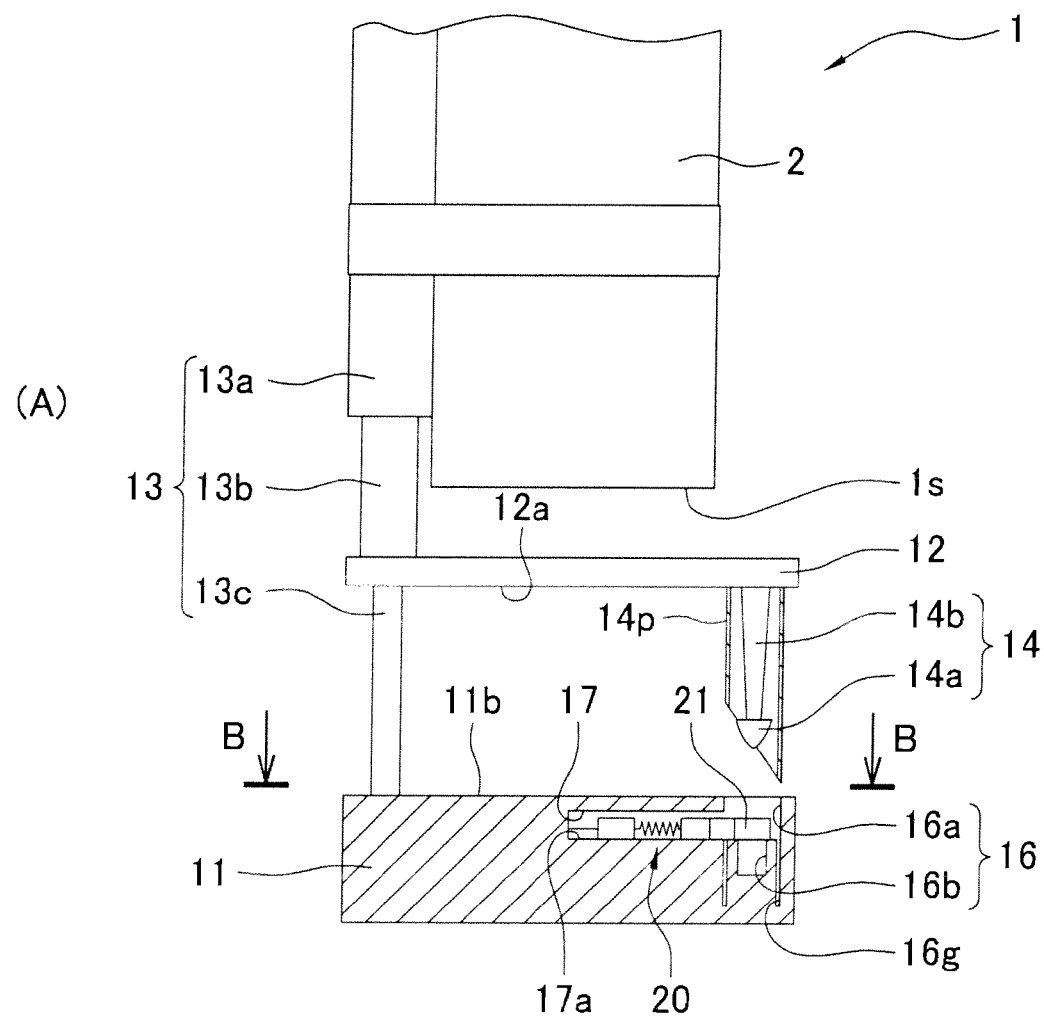
FIG. 21 shows (A): a schematic side view of the suturing apparatus 10B and (B): a fragmentary view taken in the direction of arrows B-B in (A).
Figure 21:
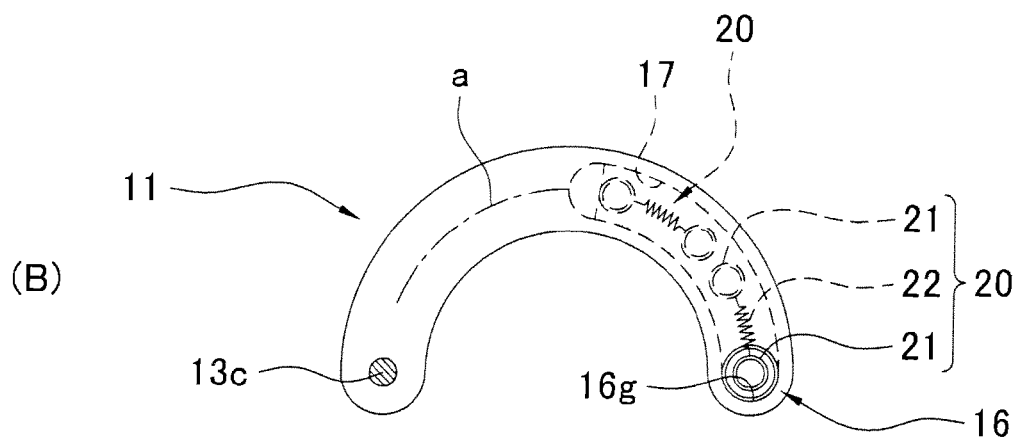
Figure 22:
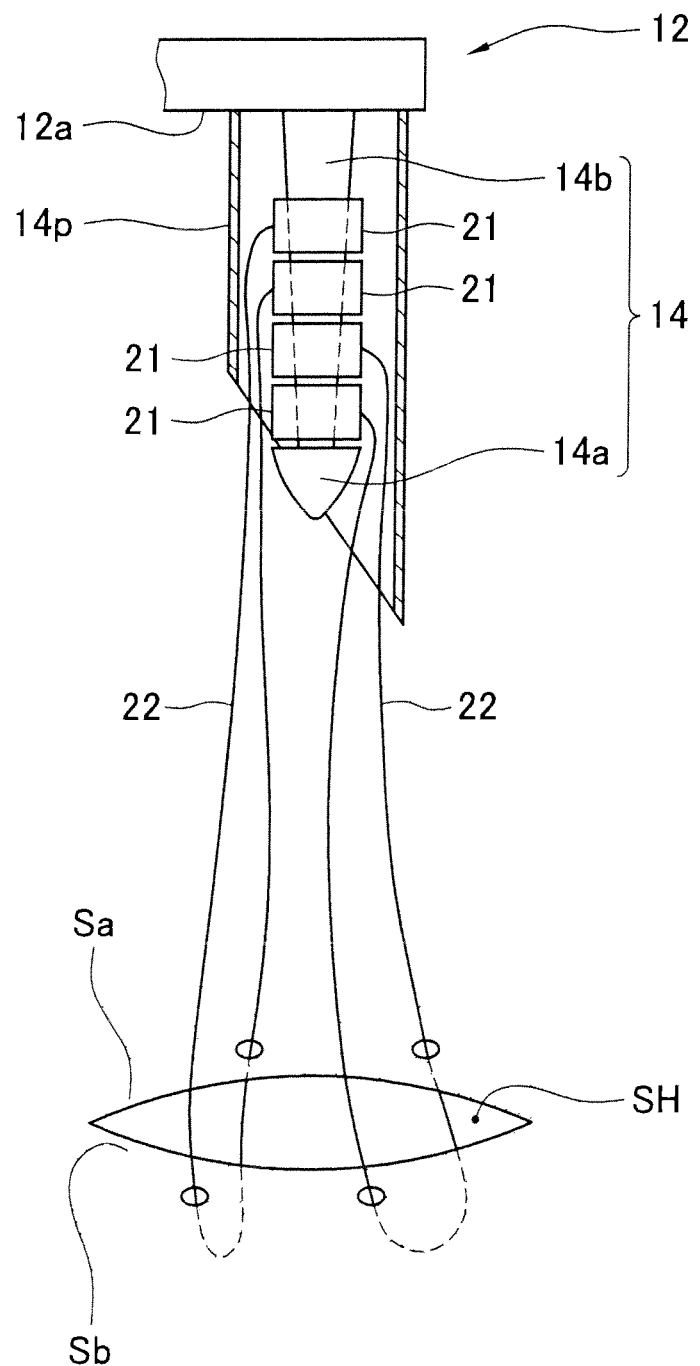
FIG. 22 is a schematic view illustrating the incised part SH sutured by the suturing apparatus 10B in the embodiment.

Although a structure of the protector is not particularly limited, a structure shown in FIGS. 20 to 22 may be employed, for example.

As shown in FIGS. 20 to 22, a hollow needle 14p is provided on the front face 12a of the rear arm 12 in the suturing apparatus 10B. A base end of the hollow needle 14p is fixed to the front face 12a so that an axial direction of the hollow needle 14p is perpendicular to the front face 12a (the axial direction becomes parallel with the axial direction of the tip of the rear-arm moving tube 13b). The needle-like member 14 is attached inside the hollow needle 14p so as to be coaxial with a central axis of the hollow needle 14p.

With such a configuration, when the needle-like member 14 is stuck into an object to be sutured such a gastric wall, a force is not applied to the needle-like member 14 from a radial direction of the needle-like member 14. The needle-like member 14 can therefore be prevented from being bent or broken.

Figure 23:
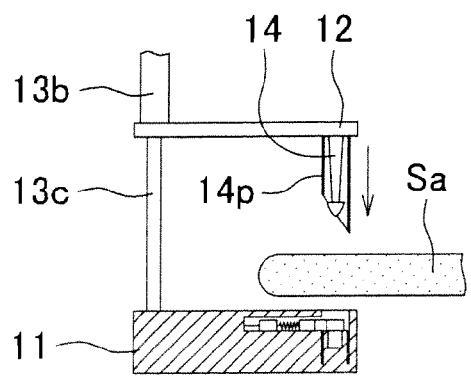
FIG. 23 shows schematic views illustrating a suturing operation with the suturing apparatus 10B in the embodiment.
Figure 23:
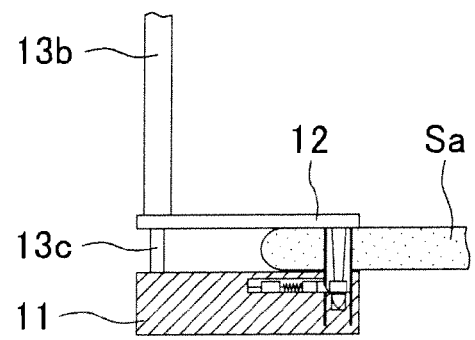
Figure 23:
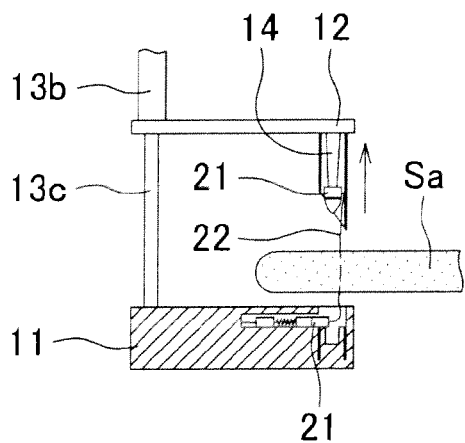
Figure 23:
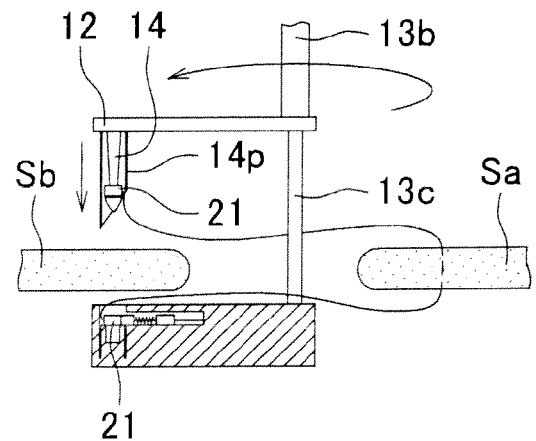
Figure 24:
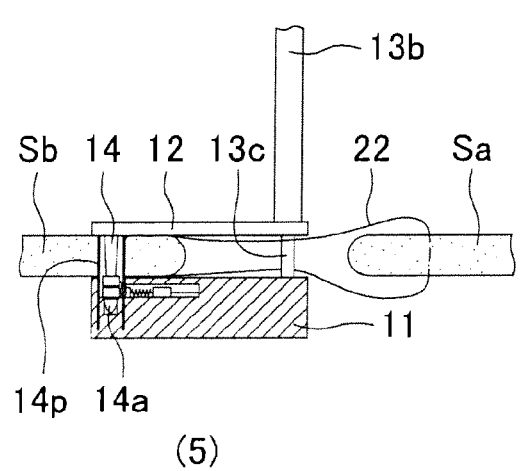
FIG. 24 shows schematic views illustrating the suturing operation with the suturing apparatus 10B in the embodiment.
Figure 24:
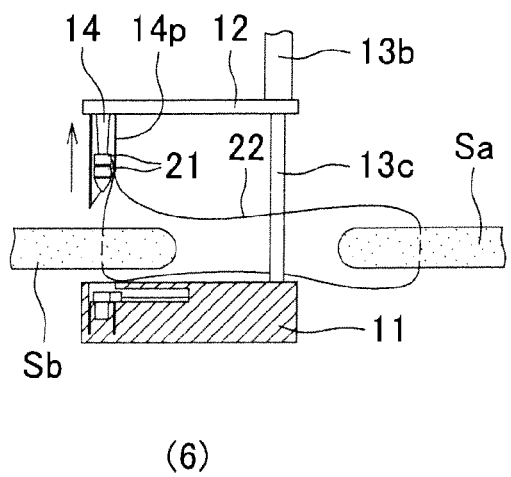
Figure 24:
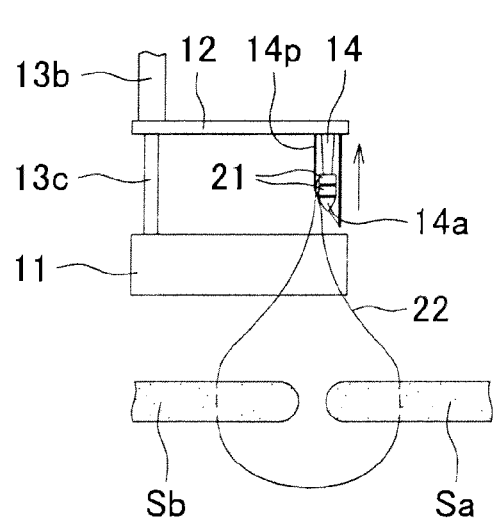
Figure 24:
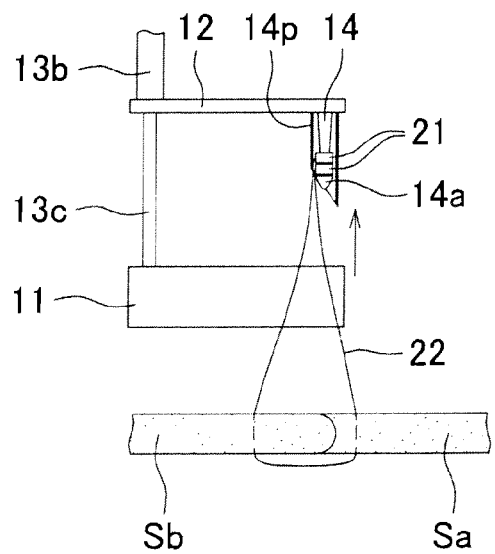

Since even the suturing apparatus 10B having the above configuration has a substantially similar configuration to the suturing apparatus 10 in FIGS. 12 to 19 except that the hollow needle 14p is provided, the incised part SH can be sutured by operating the suturing apparatus 10B similarly to the suturing apparatus 10. That is, operating the suturing apparatus 10B as shown in FIGS. 23 and 24 allows the suture thread 22 of the suturing instrument 20 in the suturing apparatus 10B to suture the incised part SH.

In the case of providing the hollow needle 14p, an annular groove 16g for housing the hollow needle 14p is preferably provided in the housing space 16 of the front arm 11, as shown in FIG. 21. More specifically, the annular groove 16g is formed around the needle-like member tip housing portion 16b so as to have the same diameter as the hollow needle 14p. The annular groove 16g has a depth to the extent that a tip of the hollow needle 14p does not come in contact with an inner bottom of the annular groove 16g when the whole arrowhead-like portion 14a of the needle-like member 14 is inserted into the needle-like member tip housing portion 16b. Then, the hollow needle 14p does not obstruct the insertion of the arrowhead-like portion 14a of the needle-like member 14 through the through hole 21h of the engagement member 21 when the front arm 11 and the rear arm 12 are moved closer to each other.

(Thread-Fastening)

As described above, the incised part SH can be sutured at the stomach with the suturing apparatuses 10 and 10B in the embodiments, and the suture thread 22 can also be fastened through a forceps port of the endoscope 1.

Figure 25:
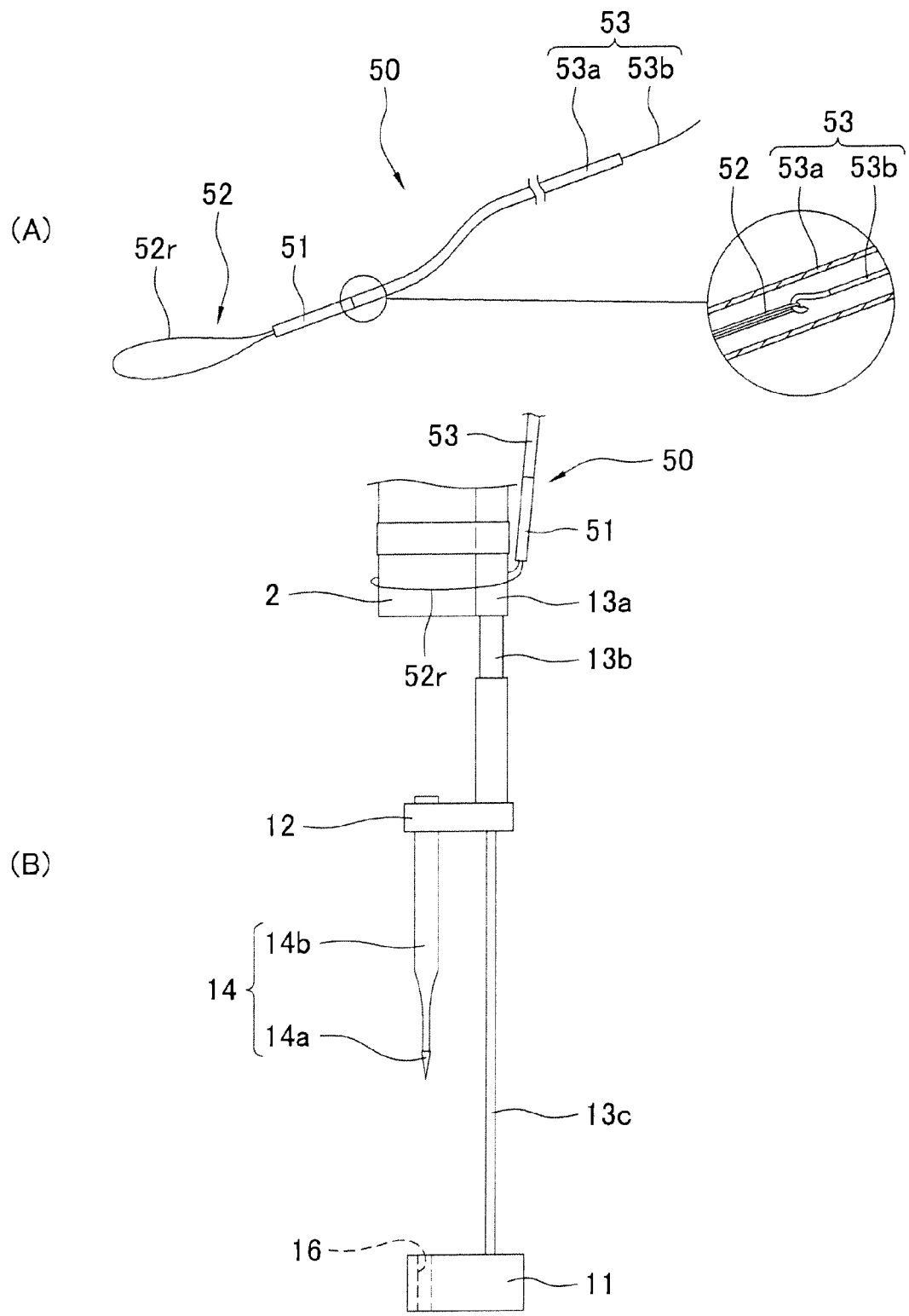
FIG. 25 shows (A): a schematic view of a thread-fastening member 50 alone and (B): a schematic view of a shaft 2 of the endoscope 1 having the thread-fastening member 50 attached thereto.

In the case of providing a thread-fastening member 50 shown in FIG. 25 on the suturing apparatus 10, the suture thread 22 can be fastened more easily.

As shown in FIG. 25, the thread-fastening member 50 includes a hollow tubular member 51, a linear member 52 inserted through the tubular member, and a moving portion 53 moving the tubular member 51 or the linear member 52.

In the linear member 52, one end 52a and the other end 52b are both inserted through the tubular member 51 to be provided on a side of the other end of the tubular member 51. A part between the one end 52a and the other end 52b of the linear member 52 protrudes from one end of the tubular member 51 to form a loop portion 52r on a side of the one end of the tubular member 51.

The tubular member 51 has such an inside diameter as to be able to smoothly move along the linear member 52 even when two of the linear members 52 are inserted therethrough. For example, when a diameter of the linear member 52 is approximately 0.3 to 1.0 mm, the inside diameter of the tubular member 51 is approximately 1.5 to 2.5 mm.

The moving portion 53 relatively moving the tubular member 51 and the linear member 52 is connected to a base end of the linear member 52. In the moving portion 53, a wire 53b is housed in a tubular member 53a. The wire 53b is movably provided along an axial direction of the tubular member 53a. A tip of the wire 53b is provided with a connection mechanism 53c connectably/removably holding the base end of the linear member 52.

According to the above structure, the connection mechanism 53c of the moving portion 53 holds the base end of the linear member 52, and the wire 53b is pulled in a direction away from the tubular member 51. Then, the loop portion 52r protruding from the tubular member 51 is drawn into the tubular member 51. This is because the tubular member 51 cannot move due to the tubular member 53a, and thereby only the linear member 52 moves. Then, the loop portion 52r can be reduced in size.

On the contrary, when the tubular member 53a is pushed toward the loop portion 52r of the linear member 52, only the tubular member 51 moves. Since the loop portion 52r protruding from the tubular member 51 can be housed in the tubular member 51, the loop portion 52r can be reduced in size.

The thread-fastening member 50 is provided so that the loop portion 52r of the linear member 52 surrounds the suturing apparatus 10. In other words, both of or either of the front arm 11 and the rear arm 12 of the suturing apparatus 10 is inserted through the loop portion 52r.

Figure 26:
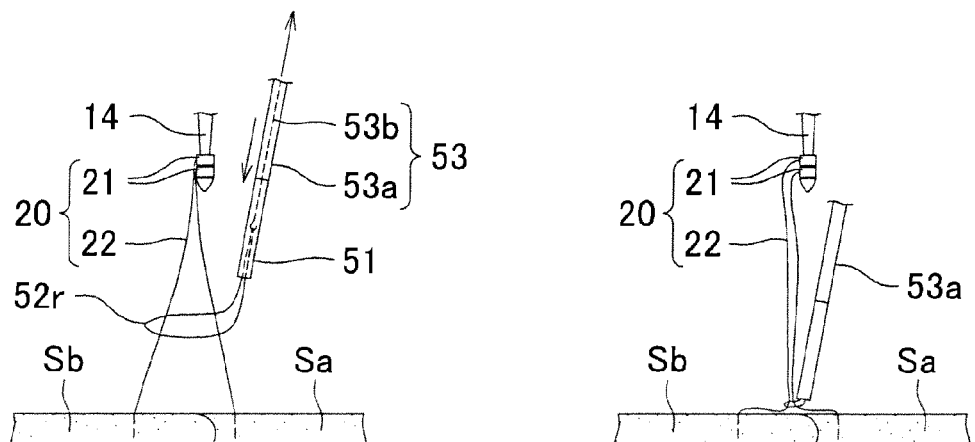
FIG. 26 shows schematic views illustrating a thread-fastening operation with the thread-fastening member 50.
Figure 26:
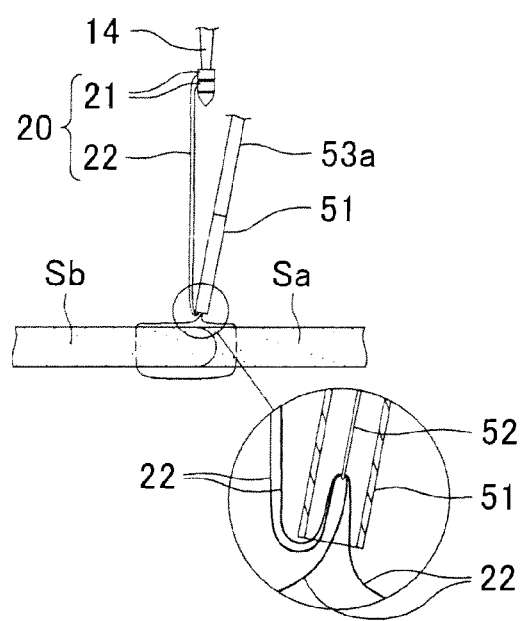
Figure 26:
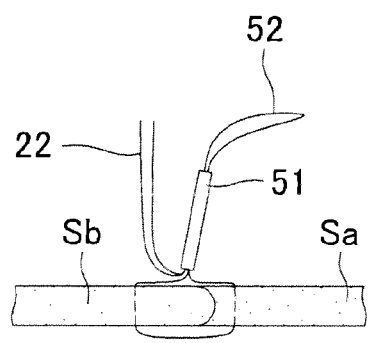

According to the above structure, the suture thread 22 can be fastened as shown in FIG. 26.

The suturing apparatus 10 having the thread-fastening member 50 is first attached to the shaft 2 of the endoscope 1. At this time, the thread-fastening member 50 is provided so that the suturing apparatus 10 is inserted through the loop portion 52s up to a part provided with the rear arm 12.

In such a state, a pair of edges Sa, Sb of the incised part SH is sutured with the suturing apparatus 10 according to the above described method. That is, both ends of the suture thread 22 of the suturing instrument 20 are located on the same side with respect to the incised part SH.

In such a state, when the both ends of the suture thread 22 is pulled by the suturing instrument 20, end faces of the pair of edges Sa, Sb in the incised part SH can come in contact with each other.

In the above state, the loop portion 52r of the linear member 52 of the thread-fastening member 50 is moved to be located between the both ends of the suture thread 22 (that is, the tip of the needle-like member 14) and the pair of edges Sa, Sb.

When the loop portion 52r is provided at a position suitable for thread-fastening, the wire 53b is pulled in the direction away from the tubular member 51. The loop portion 52r is then reduced in size, and both end portions of the suture thread 22 are bundled by the loop portion 52r.

When the wire 53b is further pulled in the state where the both end portions of the suture thread 22 are bundled by the loop portion 52r, the suture thread 22 is also drawn into the tubular member 51 together with the loop portion 52r. Since the tubular member 51 has the inside diameter to the extent that two linear members 52 can be inserted therethrough, the linear member 52 and the suture thread 22 are housed in the tubular member 51 in a close contact with each other and in a compressed manner. Since the suture thread 22 and the linear member 52 are housed in the tubular member 51 in a tight fitted manner, the suture thread 22 and the linear member 52 are fixed not to come out of the tubular member 51. As a result, the both end portions of the suture thread 22 are fastened.

As described above, the thread-fastening member 50 allows the loop portion 52r to bundle and fasten the suture thread 22 simply by providing the loop portion 52r of the linear member 52 so as to surround the both end portions of the suture thread 22 and by pulling the linear member 52. The suture thread 22 can therefore be fastened quickly and easily.

(Another Thread-Fastening Member 30)

The suture thread 22 may also be fastened by a thread-fastening member 30 as follows.

Figure 27:
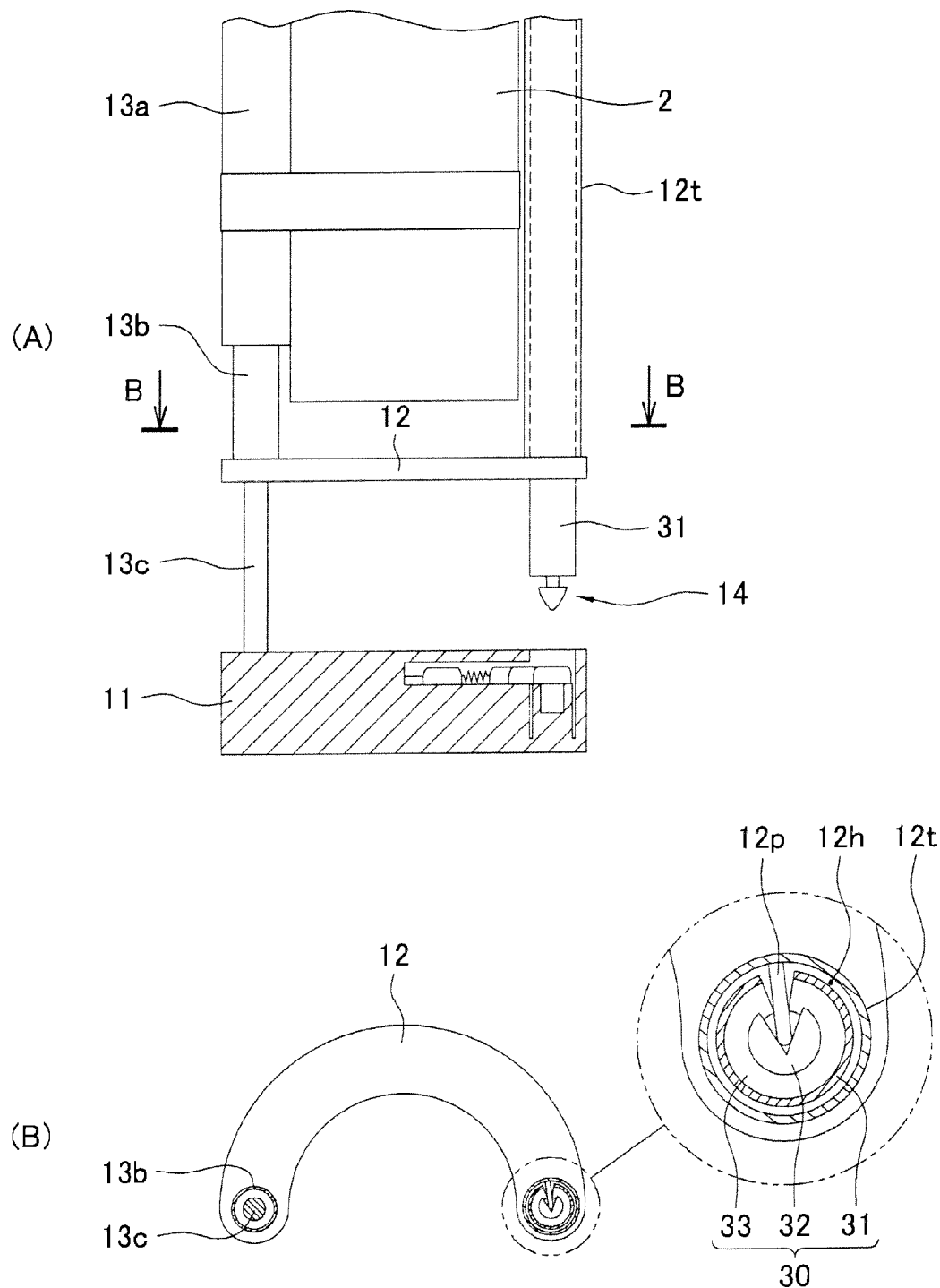
FIG. 27 shows schematic views of the suturing apparatus 10 having a thread-fastening member 30; and (A) a schematic side view, and (B): a sectional view taken in the direction of arrows B-B in (A).

As shown in FIG. 27, the thread-fastening member 30 includes a tubular member 31 of a hollow tube, and a clamp member 32 and a fastening member 33 provided in the tubular member 31. The clamp member 32 can fasten the suture thread 22.

(Description of Structure of Rear Arm 12)

In the case of using the thread-fastening member 30 shown in FIG. 27, it is necessary for the rear arms 12 of the suturing apparatuses 10 and 10B to have a structure in which the thread-fastening member 30 can be provided at the tip of the needle-like member 14. The structure of the rear arm 12 is first described.

As shown in FIG. 27, the rear arm 12 is provided with a through hole 12h extending between both sides of the rear arm 12 (the top and the bottom in FIG. 27) along a direction in which the front arm 11 and the rear arm 12 are moved closer to or away from each other.

An inside diameter of the through hole 12h is longer than the outside diameter of the needle-like member 14. A needle-supporting protrusion 12p extending from an inner face of the through hole 12h in a radial direction of the through hole 12h is provided in the through hole 12h. The base end of the needle-like member 14 is attached to a surface of the needle-supporting protrusion 12p on a side of the front arm 11. Obviously, the axial direction of the needle-like member 14 becomes parallel with the direction in which the front arm 11 and the rear arm 12 are moved closer to or away from each other.

A tip of an introduction tube 12t is attached to the back face 12b of the rear arm 12. The introduction tube 12t is a long member extending along an axial direction and has a length to the same extent as that of the shaft 2 of the endoscope 1. The introduction tube 12t is made of a tube having flexibility (for example, a tube made of polyethylene, reinforced vinyl or reinforced plastics) to the extent of being able to bend following the bend of the shaft 2, and is fixed to the shaft 2 so as to be provided along the shaft 2.

An inside diameter of the introduction tube 12t is equal to or slightly longer than the inside diameter of the through hole 12h. The tip of the introduction tube 12t is attached to the back face 12b of the rear arm 12 so that the through hole 12h is located inside the introduction tube 12t when viewed from the axial direction of the through hole 12h (see FIG. 27 (B)).

Because of this, an object can be supplied ahead of the front face 12a of the rear arm 12 through one end of the introduction tube 12t and the through hole 12h when the object (for example, the thread-fastening member 30) is inserted through the introduction tube 12t from the other end of the introduction tube 12t. In other words, the object can be moved ahead of the needle-like member 14.

A method for fixing the introduction tube 12t to the shaft 2 is not particularly limited. A method may be any as long as the introduction tube 12t can be fixed without preventing a deformation such as the bend of the shaft 2. For example, the introduction tube 12t can be fixed by a belt-like member made of a material such as polyethylene, reinforced vinyl, reinforced plastics or aluminum, or an annular fastener made of a material such as polyethylene, reinforced vinyl or metal, but not particularly limited thereto.

(Description of Thread-Fastening Member 30)

The thread-fastening member 30 will be described in detail now.

Figure 28:
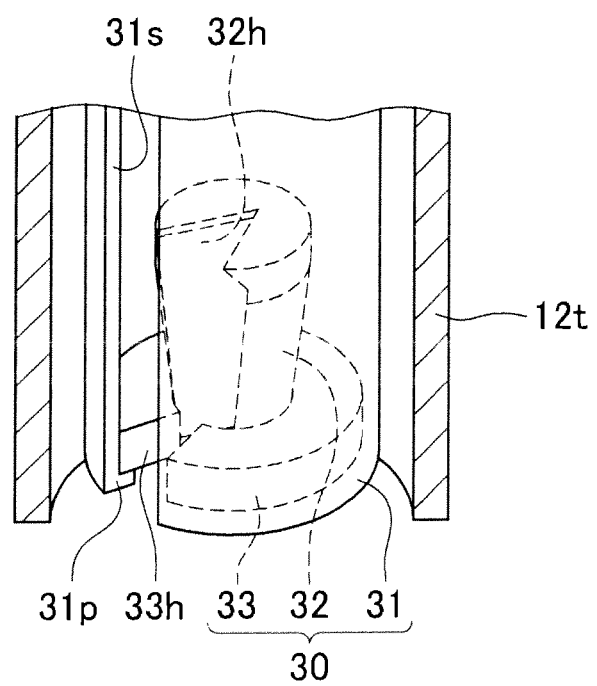
FIG. 28 is a schematic view of the thread-fastening member 30.

As described above, the thread-fastening member 30 includes the tubular member 31 of a hollow tube, and the clamp member 32 and the fastening member 33 provided in the tubular member 31 (FIG. 28).

(Description of Tubular Member 31)

The tubular member 31 is a long member extending along an axial direction and has a length to the same extent as that of the shaft 2 of the endoscope 1. An outside diameter of the tubular member 31 is shorter than the inside diameter of the through hole 12h of the rear arm 12.

A slit 31s is provided on a side face of the tubular member 31. The slit 31s is formed along an axial direction of the tubular member 31. A width of the slit 31s is wider than that of the above needle-supporting protrusion 12p. The tubular member 31 is made of a tube having flexibility (for example, a tube made of polyethylene, reinforced vinyl or reinforced plastics).

A protrusion 31p protruding inward is provided on an inner face of an opening at a tip of the tubular member 31. The fastening member 33 described later is placed on the protrusion 31p. The protrusion 31p can hold the fastening member 33 described later not to come out of the tip of the tubular member 31. However, the protrusion 31p has strength to the extent that the protrusion 31p is deformed or the like to let the fastening member 33 out from the tip of the tubular member 31 when a force along the axial direction of the tubular member 31 is applied to some extent. The reason will be described later.

(Description of Fastening Member 33)

Figure 29:
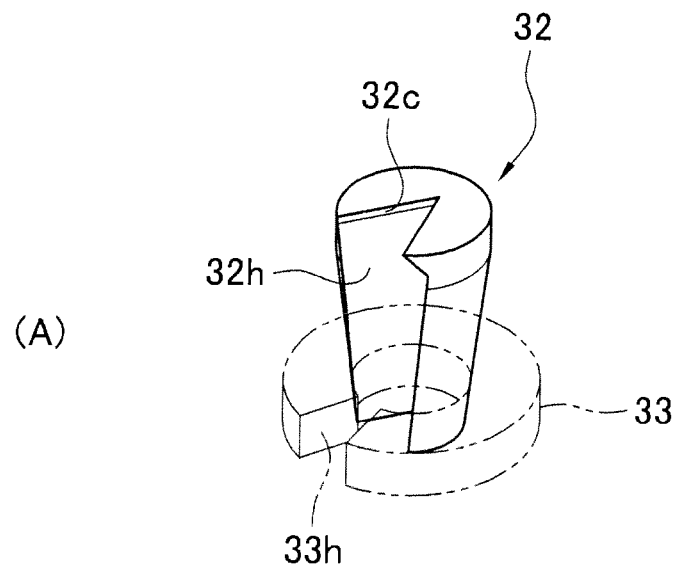
FIG. 29 shows schematic views of a clamp member 32 alone.
Figure 29:
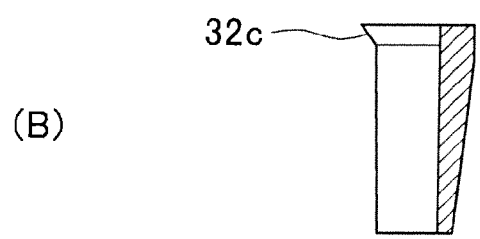
Figure 29:
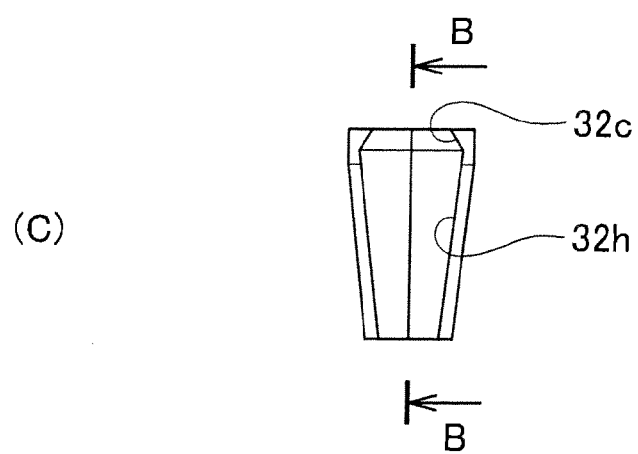

As shown in FIGS. 27 to 29, the fastening member 33 is housed inside the tubular member 31. The fastening member 33 is placed on the protrusion 31p provided on the inner face of the tip of the tubular member 31.

The fastening member 33 is an annular (ring) member having a notch 33h. An outside diameter of the fastening member 33 is substantially equal to an inside diameter of the tubular member 31. That is, the fastening member 33 is a substantially C-shaped member. A width of the notch 33h of the fastening member 33 is wider than that of the above needle-supporting protrusion 12p.

(Description of Clamp Member 32)

As shown in FIGS. 27 and 28, the clamp member 32 is housed inside the tubular member 31. The tip of the clamp member 32 is inserted into the fastening member 33.

As shown in FIGS. 28 and 29, the clamp member 32 is a member whose outside diameter becomes shorter from a base end (an upper part in FIGS. 28 and 29) toward the tip (a bottom part in FIGS. 28 and 29). More specifically, an outside diameter of the base end of the clamp member 32 is not less than an inside diameter of the fastening member 33 and not more than the inside diameter of the tubular member 31. Moreover, the outside diameter of the tip of the clamp member 32 is not more than the inside diameter of the fastening member 33.

The clamp member 32 has a thread-housing groove 32h extending from a top end to a bottom end thereof in a continuous manner. When a force is applied inward, along a radial direction, so as to nip the thread-housing groove 31h on an outer face of the clamp member 32, inner faces of the thread-housing groove 32h are moved closer to each other. The clamp member 32 having the shape shown in FIGS. 28 and 29 is formed with a material, for example, gold, tin (Sn), indium (In), or an alloy including these. The material is easily deformed, and once the material is deformed, a shape thereof can be maintained unless a force is applied. If the above force is applied, the clamp member 32 is deformed allowing the inner faces of the thread-housing groove 32h to come in contact with each other. The material of the clamp member 32 is not particularly limited as long as the material has the above function.

In the thread-housing groove 32h of the clamp member 32, a width of the groove becomes smaller from a base end toward a tip. A cutting edge 32c is provided at the top end of the inner faces facing each other in the thread-housing groove 32h. That is, when the clamp member 32 is deformed so that the inner faces of the thread-housing groove 32h are moved closer to each other, the base ends (cutting edge 32c) of the thread-housing groove 32h come in contact with each other after the tips of the thread-housing groove 32h come in contact with each other. The reason will be described later.

The above shape allows the tubular member 31 to be inserted into the introduction tube 12t. Moreover, even if the introduction tube 12t is bent, the tubular member 31 can be moved along the axial direction of the introduction tube 12t, while changing in shape following the bend. Therefore, if the clamp member 32 and the fastening member 33 are housed inside the tubular member 31, the clamp member 32 and the fastening member 33 can be moved along the axial direction of the introduction tube 12t together with the tubular member 31.

When a position of the slit 31s of the tubular member 31 matches with a position of the needle-supporting protrusion 12p in the through hole 12h of the rear arm 12 in a circumferential direction of the through hole 12h of the rear arm 12 (see FIG. 27 (B)), the tubular member 31 can pass through the through hole 12h with the needle-like member 14 housed therein. That is, when the tubular member 31 passes through the through hole 12h with the needle-supporting protrusion 12p housed in the slit 31s, the tip of the tubular member 31 can be moved ahead of the front face 12a of the rear arm 12 or the needle-like member 14.

Similarly, in the tubular member 31, positions of the thread-housing groove 32h of the clamp member 32 and the notch 33h of the fastening member 33 match with the position of the needle-supporting protrusion 12p in the through hole 12h of the rear arm 12 (see FIG. 27 (B)). In that case, the clamp member 32 and the fastening member 33 can pass through the through hole 12h so that the needle-like member 14 passes inside the thread-housing groove 32h. That is, when the tubular member 31 passes through the through hole 12h with the needle-supporting protrusion 12p housed in the slit 31s, the clamp member 32 and the fastening member 33 can also be moved ahead of the front face 12a of the rear arm 12 or the needle-like member 14.

(Thread-Fastening Operation)

A thread-fastening operation using the above thread-fastening member 30 will be described with reference to FIGS. 30 and 31.

First, when the end faces of the pair of edges Sa, Sb in the incised part SH come in contact with each other, the tubular member 31 of the thread-fastening member 30 is inserted from the other end of the introduction tube 12t. At this time, the position of the slit 31s of the tubular member 31 matches with positions of an opening of the thread-housing groove 32h of the clamp member 32 and the notch 33h of the fastening member 33. When the tip of the tubular member 31 reaches a position of the rear arm 12, the tubular member 31 is rotated around the axis. Then, the position of the slit 31s matches with the position of the needle-supporting protrusion 12p in the circumferential direction of the through hole 12h of the rear arm 12. Thus, the tip of the tubular member 31, clamp member 32 and the fastening member 33 can pass through the through hole 12h of the rear arm 12. This allows the tip of the tubular member 31, clamp member 32 and the fastening member 33 to be provided ahead of the needle-like member 14.

Figure 30:
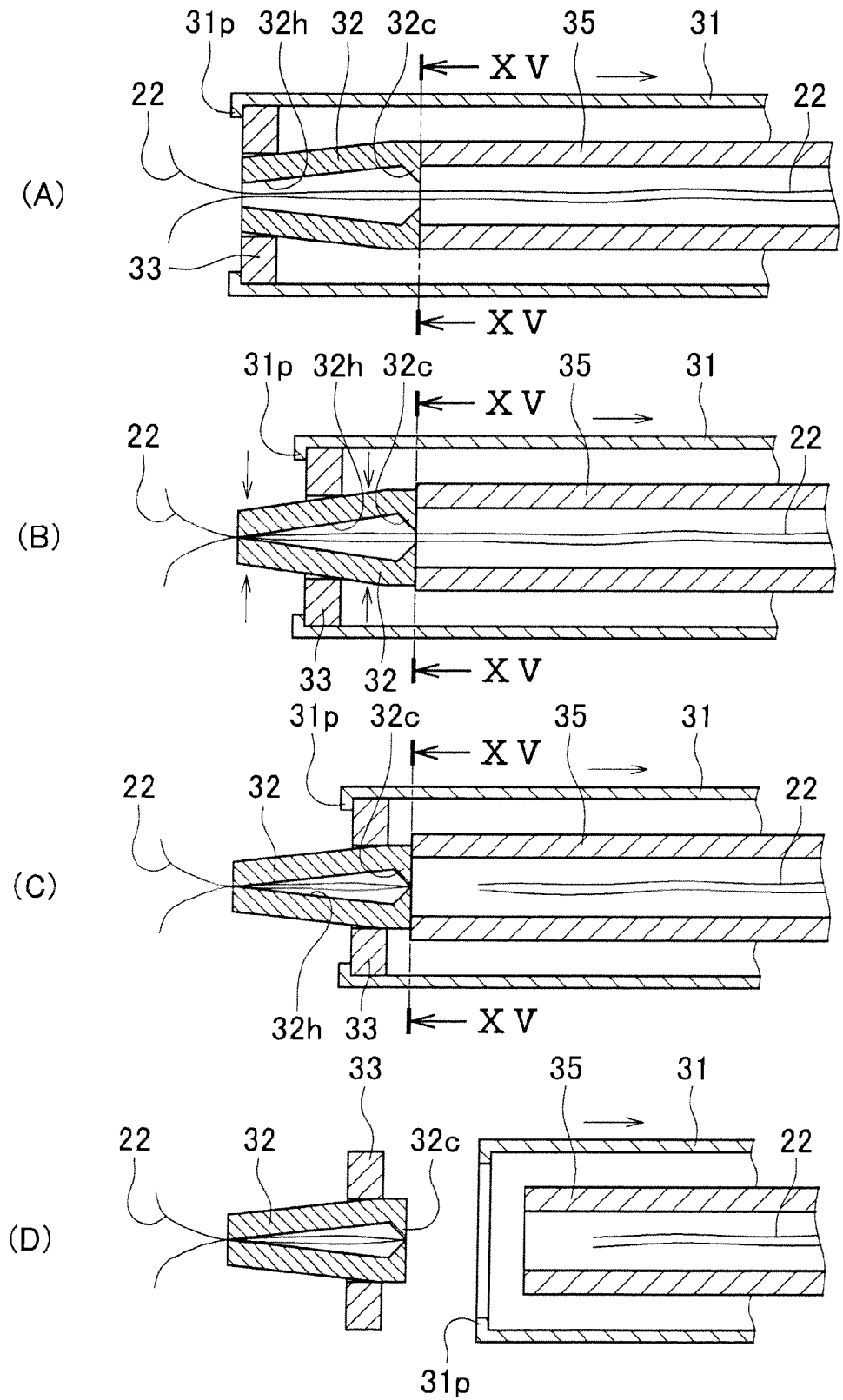
FIG. 30 shows schematic views illustrating a thread-fastening operation with the thread-fastening member 30.
Figure 31:
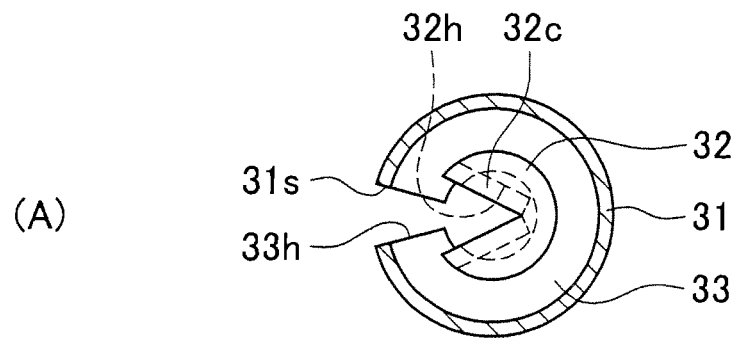
FIG. 31 shows sectional views taken in the direction of arrows XV-XV in (A) to (C) in FIG. 30.
Figure 31:
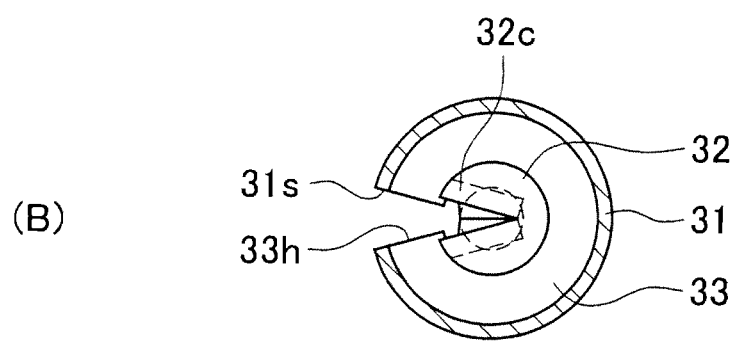
Figure 31:
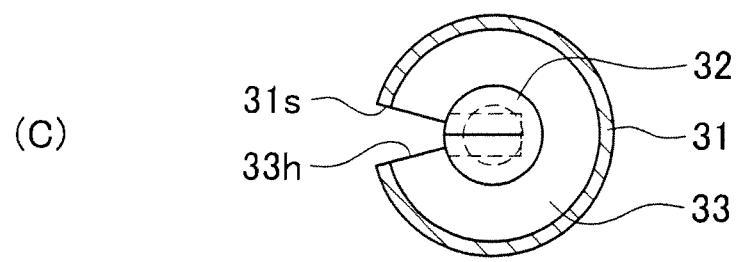
Figure 32:
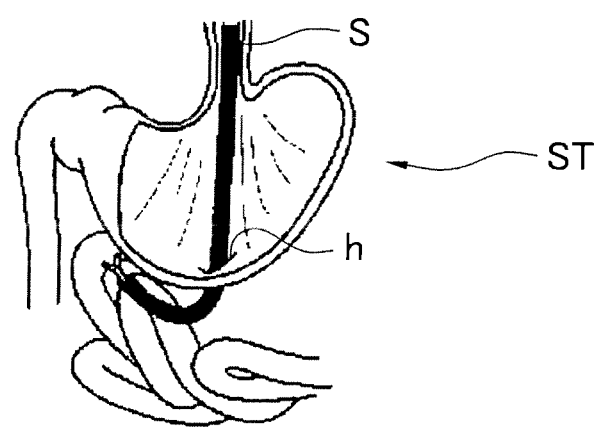
FIG. 32 is a diagram illustrating one example of surgery according to NOTES.

At this time, the suture thread 22 located ahead of the needle-like member 14 is provided in the thread-housing groove 32h because the needle-like member 14 passes inside the thread-housing groove 32h of the clamp member 32 (see FIG. 30 (A)).

The tip of the tubular member 31 or the like passing through the through hole 12h of the rear arm 12 further proceeds, and the tip of the tubular member 31, that is, the tip of the clamp member 32 is provided at a position where the suture thread 22 is fastened (hereinafter, referred to as a thread-fastening position). The thread-fastening position refers to a position where a length of the suture thread 22, that is, a length of the suture thread 22 located on a side of the incised part SH with respect to the tip of the clamp member 32 is long enough to keep the end faces of the edges Sa, Sb of the incised part SH in contact with each other.

When the tip of the clamp member 32 is provided at the thread-fastening position, a tubular supporting member 35 is inserted into the tubular member 31. The supporting member 35 is a tubular member having a section formed into a substantially similar figure to that of the tubular member 31 and can pass through the through hole 12h of the rear arm 12.

Then, an end face of a tip of the supporting member 35 is provided so as to come in surface contact with an end face of the base end of the clamp member 32. After that, the supporting member 35 is fixed relatively movable with respect to the tubular member 31 but not relatively movable with respect to the thread-fastening position.

A method for fixing in such a manner is not particularly limited. For example, a method may be employed in which a base end of the supporting member 35 is fixed to the shaft 2 of the endoscope 1. If a slight movement with respect to the thread-fastening position is accepted, a doctor to perform an operation may hold the supporting member 35.

The supporting member 35 may also be provided in the tubular member 31 at the beginning.

When the movement of the supporting member 35 is fixed, the tubular member 31 is moved toward the base end (FIG. 30 (B)). That is, the tubular member 31 is moved toward the rear arm 12. At this time, the fastening member 33 is also moved toward the rear arm 12 together with the tubular member 31 because the fastening member 33 is placed on the protrusion 31p of the tubular member 31.

Then, a force is applied to the clamp member 32 inserted into the fastening member 33 along a direction from the fastening member 33 toward the rear arm 12. However, since the supporting member 35 is fixed not relatively movable with respect to the thread-fastening position, the clamp member 32 cannot relatively move with respect to the thread-fastening position, similarly to the supporting member 35. Because of this, not only a stress in a direction of movement of the tubular member 31 but also a stress in a radial direction of the tubular member 31 (in other words, a force applied inward along a radial direction at a position nipping the thread-housing groove 32h) are generated between the clamp member 32 and the fastening member 33. When the stress along the radial direction of the tubular member 31 is applied, the clamp member 32 is deformed so that the inner faces of the thread-housing groove 32h are moved closer to each other. Then, the outside diameter of the clamp member 32 is reduced in size, and the tip of the clamp member 32 is inserted through the fastening member 33 (FIG. 30 (B)).

When the outside diameter of the clamp member 32 is reduced in size to some extent, the inner faces of the tip of the thread-housing groove 32h come in contact with each other. A movement of the suture thread 22 is therefore fixed by being sandwiched between the inner faces of the tip. That is, the movement of the suture thread 22 is fixed by the tip of the clamp member 32 to the same extent as the case of thread-fastening (FIG. 30 (B) and FIG. 31 (B)). The tip of the clamp member 32 corresponds to a gripper in Claims.

When the tubular member 31 is further moved toward the base end, the clamp member 32 is further deformed to reduce the outside diameter, causing the inner faces of the base end of the thread-housing groove 32h to come in contact with each other. That is, the cutting edge 32c provided on the base end of the thread-housing groove 32h comes in contact with the suture thread 22 (FIG. 30 (C) and FIG. 31 (C)). Then, the suture thread 22 is cut by the cutting edge 32c. That is, in the suture thread 22, a part having sutured the edges Sa, Sb of the incised part SH is cut off from the engagement member 21 engaged with the needle-like member 14.

However, in the suture thread 22, a part located on a side of the edges Sa, Sb of the incised part SH with respect to the part cut by the cutting edge 32c is held by the tip of the clamp member 32. Therefore, the incised part SH is maintained in a sutured state with the suture thread 22.

When the tubular member 31 is furthermore moved toward the base end after the inner faces of the base end of the thread-housing groove 32h come in contact with each other, the stress generated between the clamp member 32 and the fastening member 33 in the direction of movement of the tubular member 31 abruptly increases. This is because the clamp member 32 cannot be deformed so as to reduce the outside diameter. Then, the protrusion 31p of the tubular member 31 cannot hold the fastening member 33. Therefore, the protrusion 31p or the tubular member 31 itself is deformed, causing the fastening member 33 to be removed from the tip of the tubular member 31 (FIG. 30 (D)). Because of this, the suture thread 22 having sutured the incised part SH is cut off from the suturing apparatus 10, while being fastened by the clamp member 32. That is, the incised part SH can be sutured with the suture thread 22.

As described above, with the thread-fastening member 30, the suture thread 22 can be fastened simply by housing the clamp member 32 and the fastening member 33 in the tubular member 31 and pulling the tubular member 31 out. Then, in NOTES, from removal of a tumor or the like to suturing can be performed only with a flexible endoscope provided in a digestive tract. Therefore, an operation can be performed without forming a scar on a body surface.

A shape of the clamp member 32 is not limited to the shape shown in FIG. 29. For example, a pair of separated members may be connected by a metal plate or the like to form a member having a thread-housing groove between the pair of members. When the above force is applied even in this case, the metal plate or the like is deformed, allowing inner faces of the thread-housing groove at the pair of members to come in contact with each other.

The structure of the protrusion 31p is not particularly limited. The protrusion 31p may have any strength as long as the fastening member 33 can be held so as not to come out from the tip of the tubular member 31, and further, the fastening member 33 can be discharged from the tip of the tubular member 31 by deformation or the like when a force is applied to some extent or more along the axial direction of the tubular member 31.

In the above example, the sections of the tubular member 31, the clamp member 32 and the fastening member 33, and the through hole 12h of the rear arm 12 are substantially circular. However, these shapes are not necessarily circular. The clamp member 32 and the fastening member 33 are simply required to have a structure in which, when the clamp member 32 is pressed into the fastening member 33, the clamp member 32 and the fastening member 33 function as the above to nip and hold the suture thread 22 in the thread-housing groove 32h of the clamp member 32. A substantially rectangular shape may be employed.

Further, the clamp member 32 does not necessarily have the cutting edge 32c. In such a case, the suture thread 22 may be cut by forceps or the like after the thread-fastening with the clamp member 32.

INDUSTRIAL APPLICABILITY

The suturing apparatus of the present invention is suitable for natural orifice transluminal endoscopic surgery such as surgery for forming a through hole in a digestive tract or surgery on abdominal cavity performed with an endoscope inserted into cavity of a digestive tract such as a mouth, an anus or a vagina.

REFERENCE SIGNS LIST 1 endoscope
2 shaft
3 suturing apparatus
11 front arm
11s branch portion
12 rear arm
12s branch portion
13 arm moving means
14 needle-like member
16 housing space
20 suturing instrument
21 engagement member
22 suture thread
30 thread-fastening member
31 tubular member
32 clamp member
32h thread-housing groove
32c cutting edge
33 fastening member
40 connection mechanism
41 front connection member
41h guide groove
41a guide face
42a reference side face
42b positioning side face
50 thread-fastening member
51 tubular member
52 linear member
52r loop portion
ST gastric wall

The invention claimed is:

1. A suturing apparatus attachable to an endoscope and insertable into a body for use, the apparatus comprising:
a front arm;
a rear arm configured to move closer to or away from the front arm;
arm moving means for causing the front arm and the rear arm to move closer to or away from each other; and
rocking means for relatively rocking the front arm and the rear arm around a rocker shaft in parallel with a direction in which the front arm and the rear arm are moved closer to or away from each other,
wherein the rear arm includes: a needle-like member attached to the rear arm so that a tip of the needle-like member faces to the front arm and a central axis thereof becomes parallel with the direction in which the front arm and the rear arm are moved closer to or away from each other,
the front arm includes: a pair of branch portions whose base ends are connected to each other, the pair of branch portions each being provided with a housing space capable of housing the tip of the needle-like member when the front arm and the rear arm are moved closer to each other,
each of the housing spaces houses each of a pair of engagement members capable of being engaged with the needle-like member, and
the pair of engagement members housed in the housing spaces are connected to each other by a suture thread.

2. The suturing apparatus according to claim 1, further comprising:
a connection mechanism including a front connection member and a rear connection member removably engageable with each other,
wherein the rear connection member is provided on the rear arm,
the front connection member is provided on the front arm, and
the connection mechanism is formed so that the front connection member and the rear connection member fix the front arm and the rear arm at a predetermined position, and, in a fixed state at the predetermined position, are engaged with each other, and are movable along the direction in which the front arm and the rear arm are moved closer to or away from each other, the predetermined position being a position where a central axis of each housing space corresponds to a central axis of the needle-like member.

3. The suturing apparatus according to claim 2, wherein the front connection member is provided with a guide groove engaged with the rear connection member and guiding a movement of the rear connection member along an axial direction of the rocker shaft.

4. The suturing apparatus according to claim 3,
wherein the front arm is provided with a pair of housing spaces, the guide groove formed in the front connection member includes: a pair of intersecting surfaces in parallel with the axial direction of the rocker shaft and intersecting each other, the rear connection member includes:
  a reference side face in parallel with the axial direction of the rocker shaft; and
  a pair of positioning side faces in parallel with the axial direction of the rocker shaft and intersecting with the reference side face, the rear connection member is provided so that, when the reference side face is engaged with the guide groove so as to come in surface contact with one intersecting surface, one positioning side face comes in contact with the other intersecting surface, and, when the reference side face is engaged with the guide groove so as to come in surface contact with the other intersecting surface, the other positioning side face comes in contact with the one intersecting surface, and the pair of housing spaces is formed so that, when the rear connection member is engaged with the guide groove so that the reference side face comes in surface contact with one intersecting surface, a central axis of one housing space corresponds to the central axis of the needle-like member, and, when the rear connection member is engaged with the guide groove so that the reference side face comes in surface contact with the other intersecting surface, a central axis of the other housing space corresponds to the central axis of the needle-like member.

5. The suturing apparatus according to claim 1, wherein the engagement member includes: a through hole through which the tip of the needle-like member is inserted, and
the tip of the needle-like member is provided with a falling-off prevention portion preventing the engagement member from coming out of the tip when the tip is inserted through the through hole of the engagement member.

6. The suturing apparatus according to claim 5, wherein the falling-off prevention portion is an expanded diameter portion formed on a side face of the needle-like member.

7. The suturing apparatus according to claim 6, wherein an engagement piece engaged with the expanded diameter portion is provided on an inner face of the through hole in the engagement member.

8. The suturing apparatus according to claim 5,
wherein the engagement member includes:
  an engagement portion with the through hole; and
  a connection piece for connection with the suture thread, wherein
an axial direction of the connection piece is in parallel with a central axis of the through hole.

9. The suturing apparatus according to claim 8, wherein a connection-piece housing groove is provided on a side face of the front arm along an axial direction of the housing space.

10. The suturing apparatus according to claim 1,
wherein the rear arm includes: a hollow needle provided on a surface on a side of the front arm so that an axial direction of the hollow needle becomes parallel with the direction in which the front arm and the rear arm are moved closer to or away from each other, and
the needle-like member is provided in the hollow needle.

11. The suturing apparatus according to claim 1, wherein the suturing apparatus is attached to an endoscope so that both of the front arm and the rear arm are located ahead of a tip face of the endoscope.

12. The suturing apparatus according to claim 1, further comprising:
a thread-fastening member including a hollow tubular member, and a linear member having a loop portion inserted through the tubular member and protruding from one end of the tubular member,
wherein the thread-fastening member is configured such that the tubular member is moveable along the linear member, and
the front arm and/or the rear arm is inserted through the loop portion.

13. The suturing apparatus according to claim 1,
wherein the rear arm is provided with a through hole extending through the rear arm along the direction in which the front arm and the rear arm are moved closer to or away from each other,
the needle-like member is attached to the rear arm so as to be located in the through hole, when the through hole is viewed from an axial direction thereof,
and wherein a thread-fastening member fasten the suture thread ahead of the tip of the needle-like member, while the pair of engagement members in the suturing instrument is engaged with the tip of the needle-like member,
the thread-fastening member includes: a clamp member having a thread-housing groove through which the suture thread passes, the clamp member capable of holding the suture thread provided in the thread-housing groove when a width of the thread-housing groove becomes narrower, and
the clamp member is formed into such a shape as to be able to pass the through hole of the rear arm along the direction in which the front arm and the rear arm are moved closer to or away from each other, and as to allow the needle-like member to pass through the thread-housing groove, when passing the through hole of the rear arm.

14. The suturing apparatus according to claim 13,
wherein the thread-fastening member includes: the tubular member formed into such a shape as to be able to pass the through hole of the rear arm along the direction in which the front arm and the rear arm are moved closer to or away from each other,
a section of the tubular member is formed into such a shape as to allow the needle-like member to be housed therein at the time of passing the through hole of the rear arm,
the tubular member houses the clamp member provided so that an axial direction of the thread-housing groove corresponds to an axial direction of the tubular member, and a ring-shaped fastening member provided between the clamp member and an inner face of the tubular member,
an outside diameter of the clamp member becomes narrower from a base end thereof toward a tip, and
an inside diameter of the fastening member is not less than an outside diameter of the tip of the clamp member and not more than an outside diameter of the base end of the clamp member.

15. The suturing apparatus according to claim 14,
wherein the tubular member includes: a holding mechanism holding the fastening member at a tip of the tubular member, the holding mechanism preventing the fastening member from moving toward the tip of the tubular member, when the clamp member relatively moves toward the tip of the tubular member, until a stress generated between the clamp member and the fastening member reaches a predetermined magnitude, and the fastening member is discharged from the tip of the tubular member when the stress generated between the clamp member and the fastening member reaches the predetermined magnitude or more.

16. The suturing apparatus according to claim 13, wherein the clamp member includes:
   a gripper provided on an inner face of the thread-housing groove for nipping and holding the suture thread; and
   a cutting edge provided on the inner face of the thread-housing groove and located on a side of a base end of the gripper, and
   the cutting edge being configured to cut the suture thread when a width of the thread-housing groove becomes narrower in a state of the gripper holding the suture thread.

17. A suturing apparatus attachable to an endoscope and insertable into a body for use comprising:
   a front arm;
   a rear arm configured to move closer to or away from the front arm; and
   arm moving means for causing the front arm and the rear arm to move closer to or away from each other,
   wherein the rear arm includes: a pair of branch portions whose base ends are connected to each other,
   the pair of branch portions includes: a pair of needle-like members provided so that tips of the needle-like members face to the front arm and central axes thereof become parallel with a direction in which the front arm and the rear arm are moved closer to or away from each other,
   the front arm includes: a pair of branch portions whose base ends are connected to each other, the pair of branch portions being provided with a pair of housing spaces capable of respectively housing the tips of the pair of needle-like members when the front arm and the rear arm are moved closer to each other,
   the pair of housing spaces are provided so that, when a central axis of one housing space becomes coaxial with a central axis of one needle-like member, a central axis of the other housing space becomes coaxial with a central axis of the other needle-like member,
   each of the housing spaces houses each of a pair of engagement members capable of being engaged with the needle-like member, and
   the pair of engagement members housed in the housing spaces are connected to each other by a suture thread.

18. The suturing apparatus according to claim 17, further comprising:
   a connection mechanism including a front connection member and a rear connection member removably engageable with each other,
   wherein the rear connection member is provided on the rear arm,
   the front connection member is provided on the front arm, and
   the connection mechanism is formed so that the front connection member and the rear connection member are engaged with each other and are movable along the direction in which the front arm and the rear arm are moved closer to or away from each other, and each central axis of the plurality of needle-like members is coaxial with each central axis of the plurality of housing spaces.

19. The suturing apparatus according to claim 18, wherein the front connection member is provided with a guide groove engaged with the rear connection member and guiding a movement of the engaged rear connection member along an axial direction of a rocker shaft.

20. A suturing apparatus attachable to an endoscope and insertable into a body for use comprising:
   a front arm;
   a rear arm configured to move closer to or away from the front arm; and
   arm moving means for causing the front arm and the rear arm to move closer to or away from each other,
   wherein the rear arm includes: a needle-like member attached to the rear arm so that a tip of the needle-like member faces to the front arm and a central axis thereof becomes parallel with a direction in which the front arm and the rear arm are moved closer to or away from each other,
   the front arm is provided with a housing space capable of housing the tip of the needle-like member when the front arm and the rear arm are moved closer to each other,
   the front arm houses a suturing instrument including a pair of engagement members connected by a suture thread and capable of being engaged with the needle-like member, and
   the front arm is provided with a supply mechanism in which, when one engagement member is engaged with the needle-like member, the other engagement member can be housed outside the housing space, and then, the other engagement member can be supplied to the housing space after the one engagement member is engaged with the needle-like member.

21. The suturing apparatus according to claim 20,
   wherein the engagement member includes: a through hole through which the tip of the needle-like member can be inserted,
   the supply mechanism includes: a suturing-instrument holding space formed in the front arm, communicating with the housing space and housing the suturing instrument, and
   the housing space houses the engagement member of the suturing instrument supplied from the suturing-instrument holding space, wherein an axial direction of the through hole of the engagement member is parallel with a direction of movement of the needle-like member.

* * * * *